(12) United States Patent
Caimi et al.

(10) Patent No.: US 9,169,506 B2
(45) Date of Patent: Oct. 27, 2015

(54) PROCESS FOR PRODUCING ALPHA-1,3-GLUCAN POLYMER WITH REDUCED MOLECULAR WEIGHT

(71) Applicant: E I DU PONT DE NEMOURS AND COMPANY, Wilmington, DE (US)

(72) Inventors: Perry G Caimi, Kenneth Square, PA (US); Susan Marie Hennessey, Avondale, PA (US); Kevin D Nagy, Wilmington, DE (US); Mark S Payne, Wilmington, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/476,790

(22) Filed: Sep. 4, 2014

(65) Prior Publication Data

US 2015/0064748 A1    Mar. 5, 2015

Related U.S. Application Data

(60) Provisional application No. 61/873,851, filed on Sep. 5, 2013.

(51) Int. Cl.
*C12P 19/18* (2006.01)
*C12P 19/04* (2006.01)
*C08B 37/00* (2006.01)

(52) U.S. Cl.
CPC ............. *C12P 19/18* (2013.01); *C08B 37/0009* (2013.01); *C12P 19/04* (2013.01)

(58) Field of Classification Search
CPC ....... C12P 19/04; C12P 19/18; C12N 9/1051; C12N 9/1048; C12Y 204/01005
See application file for complete search history.

(56) References Cited

U.S. PATENT DOCUMENTS 7,000,000 B1    2/2006    O'Brien
2006/0057704 A1    3/2006    Schlothauer et al.

FOREIGN PATENT DOCUMENTS

JP    2000175694 A    6/2000
KR    20010068479 A    7/2001

OTHER PUBLICATIONS

Branden et al., Introduction to Protein Structure, Garland Publishing Inc., New York, p. 247, 1991.*
Witkowski et al., Biochemistry 38:11643-11650, 1999.*
Seffernick et al., J. Bacteriol. 183(8):2405-2410, 2001.*
Ogawa et al., Crystal Structure of (1→3)-α-D-Glucan, Fiber Diffraction Methods, French et al., ACS Symposium Series; American Chemical Society (1980), pp. 353-362.
Simpson et al., Four Glucosyltransferases, GTFJ, GTFK, GTFL and GTFM, From Streptococcus Salivarius ATCC 25975, Microbiology, vol. 141 (1995), pp. 1451-1460.
Girard et al., Activity and Stability of Dextransucrase From Leuconostoc Mesenteroides NRRL B-512F in the Presence of Organic Solvents, Enzyme and Microbial Technology, vol. 24 (1999), pp. 425-432.
Aman et al., Influence of Temperature, Metal Ions and Organic Solvents on Extracellular Glucansucrase Activity of Leuconostoc Mesenteroides AA1, J. Chem. Soc., vol. 30, No. 6 (2008), pp. 849-853.
Castillo et al., Synthesis of Levan in Water-Miscible Organic Solvents, Journal of Biotechnology, vol. 114 (2004), pp. 209-217.
Chambert et al., Study of the Effect of Organic Solvents on the Synthesis of Levan and the Hydrolysis of Sucrose by Bacillus Subtilis Levansucrase, Carbohydrate Research, vol. 191 (1989), pp. 117-123.

* cited by examiner

*Primary Examiner* — Delia Ramirez

(57) ABSTRACT

A process for producing poly alpha-1,3-glucan with reduced molecular weight is disclosed. The process comprises contacting water, sucrose, a polar organic solvent, and a glucosyltransferase enzyme in a solution to produce poly alpha-1, 3-glucan. This contacting step results in the production of poly alpha-1,3-glucan having a reduced molecular weight compared to the molecular weight of a poly alpha-1,3-glucan made in the absence of the polar organic solvent.

14 Claims, No Drawings

SEQUENCE LISTING

```
<160> NUMBER OF SEQ ID NOS: 32

<210> SEQ ID NO 1
<211> LENGTH: 4434
<212> TYPE: DNA
<213> ORGANISM: Streptococcus salivarius

<400> SEQUENCE: 1
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga aacgaacgca gtcgagactg cgaccaccac taacacccag     180
gcgacggcgg aggccgccac gaccgcgacc accgcggacg tcgcggtggc tgcggtgccg     240
aacaaagaag cggtcgttac cacggatgct ccggcggtca cgaccgagaa agcggaagaa     300
cagccggcta ccgttaaagc agaagtcgtc aatacggaag tgaaagcgcc ggaagcggct     360
ctgaaagaca gcgaggttga ggcagcgctg agcctgaaga acatcaagaa cattgatggc     420
aagtattact atgttaatga ggatggcagc cacaaagaga atttcgctat taccgtgaat     480
ggccagctgc tgtactttgg taaagacggt gcgctgacgt cctctagcac gtattctttt     540 acccaggca ctaccaatat cgtggacggt tttagcatta caaccgcgc ttacgacagc      600 agcgaggcga gctttgagct gatcgacggt tacttgaccg cagacagctg gtatcgtccg     660
gctagcatca tcaaagatgg tgttacgtgg caagcgtcca ccgccgagga ttttcgtccg     720
ctgctgatgg catggtggcc gaatgtggat acgcaggtga actatttgaa ttacatgtcc     780
aaagtttcca acctggacgc gaaatactct agcaccgaca aacaggaaac cctgaaagtg     840
gcagcaaaag acattcaaat caagattgaa caaagattc aagcggagaa gagcacgcag      900
tggctgcgtg aaactatcag cgcctttgtg aaaacccagc cgcagtggaa caaagaaacc     960
gagaattaca gcaagggtgg tggtgaggac cacctgcaag gtggcgcact gctgtatgtt    1020
aacgacagcc gtaccccttg ggcgaatagc gattaccgtc gtctgaatcg caccgcaacc    1080
aatcagacgg gcacgatcga taagtctatt ctggacgagc agtctgaccc aaaccacatg    1140
ggcggtttcg acttttctgct ggcgaacgac gtcgacctga gcaatccggt cgtgcaggct    1200
gagcagctga atcaaatcca ctatctgatg aattgggtt ccattgtgat gggtgacaag    1260
gatgcgaact tgacggcat tcgtgtcgat gcagttgaca acgtggacgc ggacatgttg    1320
caactgtata ccaattactt ccgtgagtac tacggtgtga acaagagcga agctaacgca    1380
ctggctcaca tcagcgttct ggaggcgtgg agcctgaatg ataatcatta caatgacaag    1440
accgatggtg cggcactggc aatggagaat aagcaacgtc tggcgctgtt gttttcgttg    1500
```

-continued

```
gcgaaaccga tcaaagagcg tacccccggca gtgagcccgc tgtataacaa caccttcaat    1560
accacccagc gtgatgaaaa gaccgattgg attaacaaag acggtagcaa ggcttacaac    1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga gcgacaaaaa gtataccctg    1860
aataacattc cggcagcgta tgccgtgatg ttgcagaata tggaaacgat acccgcgtc    1920
tattacggtg atctgtatac ggacgacggt cactacatgg aaaccaaatc tccgtattac    1980
gataccatcg tgaatttgat gaagagccgt atcaagtatg tttcgggtgg ccaggcgcaa    2040
cgtagctatt ggctgccgac cgacggtaag atggacaata gcgacgttga gctgtaccgc    2100
acgaatgagg tttacacgag cgtgcgctat ggtaaggata tcatgaccgc taatgatacc    2160
gaaggctcta agtattcccg caccagcggc caagtcacct ggtcgcgaa caatccgaag    2220
ctgaatctgg accaaagcgc caagttgaat gtggagatgg caaaatcca tgcgaatcag    2280
aagtatcgcg cactgattgt cggcactgcg gacggcatta agaactttac ttccgacgcg    2340
gacgccattg cagcgggtta tgtgaaagaa accgatagca acggcgtgct gaccttcggt    2400
gctaacgaca ttaagggcta cgaaacgttt gatatgagcg gtttcgtggc ggtgtgggtt    2460
ccggtgggtg catctgacaa tcaggacatt cgtgttgcgc cgagcaccga ggcaaagaaa    2520
gaaggtgagc tgaccttgaa ggcgacggaa gcgtatgata ccagctgat ttacgaaggc    2580
tttagcaatt tccagacgat cccagatggc agcgatccgt ccgtgtatac gaaccgcaag    2640
attgcggaga acgtggatct gttcaaaagc tggggtgtca ccagctttga gatggcaccg    2700
caatttgtct cggcggatga tggcaccttt ctggatagcg ttattcagaa tggctacgcc    2760
ttcgccgacc gttatgacct ggccatgtcc aagaacaaca gtatggtag caaagaggac    2820
ctgcgtgatg cactgaaagc actgcataag gcgggtattc aagctatcgc agactgggtt    2880
ccagaccaga tctaccagct gccgggcaaa gaagttgtca ccgccacccg tacggatggt    2940
gctgccgta agatcgcaga gcgattatc gaccattctc tgtatgttgc aaacagcaaa    3000
agcagcggca agattatca agcaaagtac ggtggcgagt tcctggccga gctgaaagcc    3060
aaatacccgg aaatgttcaa agttaacatg attagcacgg gtaagccgat tgatgactcc    3120
gtgaaattga agcaatggaa agccgagtac ttcaatggca ccaacgtttt ggaacgtggt    3180
gtcggctatg ttctgagcga cgaggcgacc ggtaagtatt tcacggtgac aaagaaggc    3240
aatttcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
agcccgaatg caaggacgt ctaccgtttt ctgccgaacg tatcatgct gagcaatgcg    3480
ttttacattg atgcgaacgg taatacctac ctgtacaact ctaagggtca aatgtacaaa    3540
ggcggttaca cgaaattcga tgttttctgaa acggataagg acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
aagggcaaga cgtattactt cgacgcacac actggtaatg gtatcaaaga tacctggcgc    3780
aatatcaatg gtaaatggta ctatttcgac gcgaatggcg ttgctgcgac cggtgcgcag    3840
gtgattaacg gccagaaact gtacttcaac gaggatggct cccaagtcaa aggcggcgtg    3900
```

-continued

```
gttaagaacg cagacggcac ctatagcaaa tacaaagaag ttttggtga gctggttact      3960 aacgagtttt tcacgactga tggcaatgtt tggtactacg ccggtgcaaa tggtaaaacc      4020
gttaccggtg cacaagtgat caacggccaa catttgtact tcaatgcgga cggttcccag      4080
gtgaagggtg gcgttgtcaa gaacgcggat ggcacctaca gcaagtacaa tgctagcact      4140
ggtgaacgtc tgacgaacga gttctttacg accggtgata acaattggta ttacattggc      4200
gcaaacggta gagcgtgac gggtgaggtc aagattggtg atgatactta cttttttcgcg      4260 aaggatggca acaagttaa aggtcaaacc gtcagcgccg taatggtcg cattagctac      4320 tactacggtg acagcggcaa gcgtgcggtt agcacctgga ttgagattca gccgggtgtt      4380
tatgtgtatt tcgacaaaaa cggtttggcg taccctccgc gtgttctgaa ttaa           4434
```

<210> SEQ ID NO 2
<211> LENGTH: 1477
<212> TYPE: PRT
<213> ORGANISM: Streptococcus salivarius

<400> SEQUENCE: 2

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
                20                  25                  30

Arg Thr Asn Thr Lys Glu Ala Asp Val Leu Thr Pro Ala Lys Glu Thr
            35                  40                  45

Asn Ala Val Glu Thr Ala Thr Thr Thr Asn Thr Gln Ala Thr Ala Glu
        50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110

Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
    210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
            260                 265                 270

Asp Lys Gln Glu Thr Leu Lys Val Ala Ala Lys Asp Ile Gln Ile Lys
```

|         | 275     |         |         |         | 280     |         |         |         | 285     |         |         |
|---------|---------|---------|---------|---------|---------|---------|---------|---------|---------|---------|---------|
| Ile     | Glu     | Gln     | Lys     | Ile     | Gln     | Ala     | Glu     | Lys     | Ser     | Thr     | Gln     | Trp     | Leu     | Arg     | Glu     |
| 290     |         |         |         |         | 295     |         |         |         |         | 300     |         |         |         |         |         |

Ile Glu Gln Lys Ile Gln Ala Glu Lys Ser Thr Gln Trp Leu Arg Glu
        290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Glu Asp His Leu Gln Gly Gly Ala
                        325                 330                 335

Leu Leu Tyr Val Asn Asp Ser Arg Thr Pro Trp Ala Asn Ser Asp Tyr
                340                 345                 350

Arg Arg Leu Asn Arg Thr Ala Thr Asn Gln Thr Gly Thr Ile Asp Lys
        355                 360                 365

Ser Ile Leu Asp Glu Gln Ser Asp Pro Asn His Met Gly Gly Phe Asp
370                 375                 380

Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
                405                 410                 415

Met Gly Asp Lys Asp Ala Asn Phe Asp Gly Ile Arg Val Asp Ala Val
                420                 425                 430

Asp Asn Val Asp Ala Asp Met Leu Gln Leu Tyr Thr Asn Tyr Phe Arg
        435                 440                 445

Glu Tyr Tyr Gly Val Asn Lys Ser Glu Ala Asn Ala Leu Ala His Ile
450                 455                 460

Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
                485                 490                 495

Leu Phe Ser Leu Ala Lys Pro Ile Lys Glu Arg Thr Pro Ala Val Ser
                500                 505                 510

Pro Leu Tyr Asn Asn Thr Phe Asn Thr Thr Gln Arg Asp Glu Lys Thr
                515                 520                 525

Asp Trp Ile Asn Lys Asp Gly Ser Lys Ala Tyr Asn Glu Asp Gly Thr
        530                 535                 540

Val Lys Gln Ser Thr Ile Gly Lys Tyr Asn Glu Lys Tyr Gly Asp Ala
545                 550                 555                 560

Ser Gly Asn Tyr Val Phe Ile Arg Ala His Asp Asn Asn Val Gln Asp
                565                 570                 575

Ile Ile Ala Glu Ile Ile Lys Lys Glu Ile Asn Pro Lys Ser Asp Gly
                580                 585                 590

Phe Thr Ile Thr Asp Ala Glu Met Lys Gln Ala Phe Glu Ile Tyr Asn
                595                 600                 605

Lys Asp Met Leu Ser Ser Asp Lys Lys Tyr Thr Leu Asn Asn Ile Pro
        610                 615                 620

Ala Ala Tyr Ala Val Met Leu Gln Asn Met Glu Thr Ile Thr Arg Val
625                 630                 635                 640

Tyr Tyr Gly Asp Leu Tyr Thr Asp Asp Gly His Tyr Met Glu Thr Lys
                645                 650                 655

Ser Pro Tyr Tyr Asp Thr Ile Val Asn Leu Met Lys Ser Arg Ile Lys
                660                 665                 670

Tyr Val Ser Gly Gly Gln Ala Gln Arg Ser Tyr Trp Leu Pro Thr Asp
        675                 680                 685

Gly Lys Met Asp Asn Ser Asp Val Glu Leu Tyr Arg Thr Asn Glu Val
        690                 695                 700

```
Tyr Thr Ser Val Arg Tyr Gly Lys Asp Ile Met Thr Ala Asn Asp Thr
705                 710                 715                 720

Glu Gly Ser Lys Tyr Ser Arg Thr Ser Gly Gln Val Thr Leu Val Ala
            725                 730                 735

Asn Asn Pro Lys Leu Asn Leu Asp Gln Ser Ala Lys Leu Asn Val Glu
        740                 745                 750

Met Gly Lys Ile His Ala Asn Gln Lys Tyr Arg Ala Leu Ile Val Gly
                755                 760                 765

Thr Ala Asp Gly Ile Lys Asn Phe Thr Ser Ala Asp Ala Ile Ala
770                 775                 780

Ala Gly Tyr Val Lys Glu Thr Asp Ser Asn Gly Val Leu Thr Phe Gly
785                 790                 795                 800

Ala Asn Asp Ile Lys Gly Tyr Glu Thr Phe Asp Met Ser Gly Phe Val
                805                 810                 815

Ala Val Trp Val Pro Val Gly Ala Ser Asp Asn Gln Asp Ile Arg Val
            820                 825                 830

Ala Pro Ser Thr Glu Ala Lys Lys Glu Gly Glu Leu Thr Leu Lys Ala
        835                 840                 845

Thr Glu Ala Tyr Asp Ser Gln Leu Ile Tyr Gly Phe Ser Asn Phe
850                 855                 860

Gln Thr Ile Pro Asp Gly Ser Asp Pro Ser Val Tyr Thr Asn Arg Lys
865                 870                 875                 880

Ile Ala Glu Asn Val Asp Leu Phe Lys Ser Trp Gly Val Thr Ser Phe
                885                 890                 895

Glu Met Ala Pro Gln Phe Val Ser Ala Asp Asp Gly Thr Phe Leu Asp
            900                 905                 910

Ser Val Ile Gln Asn Gly Tyr Ala Phe Ala Asp Arg Tyr Asp Leu Ala
        915                 920                 925

Met Ser Lys Asn Asn Lys Tyr Gly Ser Lys Glu Asp Leu Arg Asp Ala
    930                 935                 940

Leu Lys Ala Leu His Lys Ala Gly Ile Gln Ala Ile Ala Asp Trp Val
945                 950                 955                 960

Pro Asp Gln Ile Tyr Gln Leu Pro Gly Lys Val Val Thr Ala Thr
                965                 970                 975

Arg Thr Asp Gly Ala Gly Arg Lys Ile Ala Asp Ala Ile Ile Asp His
            980                 985                 990

Ser Leu Tyr Val Ala Asn Ser Lys  Ser Ser Gly Lys Asp  Tyr Gln Ala
        995                 1000                1005

Lys Tyr  Gly Gly Glu Phe Leu  Ala Glu Leu Lys Ala  Lys Tyr Pro
    1010                 1015                 1020

Glu Met  Phe Lys Val Asn Met  Ile Ser Thr Gly Lys  Pro Ile Asp
    1025                 1030                 1035

Asp Ser  Val Lys Leu Lys Gln  Trp Lys Ala Glu Tyr  Phe Asn Gly
    1040                 1045                 1050

Thr Asn  Val Leu Glu Arg Gly  Val Gly Tyr Val Leu  Ser Asp Glu
    1055                 1060                 1065

Ala Thr  Gly Lys Tyr Phe Thr  Val Thr Lys Glu Gly  Asn Phe Ile
    1070                 1075                 1080

Pro Leu  Gln Leu Thr Gly Lys  Glu Lys Val Ile Thr  Gly Phe Ser
    1085                 1090                 1095

Ser Asp  Gly Lys Gly Ile Thr  Tyr Phe Gly Thr Ser  Gly Thr Gln
    1100                 1105                 1110
```

```
Ala Lys Ser Ala Phe Val Thr Phe Asn Gly Asn Thr Tyr Tyr Phe
    1115                1120                1125

Asp Ala Arg Gly His Met Val Thr Asn Ser Glu Tyr Ser Pro Asn
    1130                1135                1140

Gly Lys Asp Val Tyr Arg Phe Leu Pro Asn Gly Ile Met Leu Ser
    1145                1150                1155

Asn Ala Phe Tyr Ile Asp Ala Asn Gly Asn Thr Tyr Leu Tyr Asn
    1160                1165                1170

Ser Lys Gly Gln Met Tyr Lys Gly Gly Tyr Thr Lys Phe Asp Val
    1175                1180                1185

Ser Glu Thr Asp Lys Asp Gly Lys Glu Ser Lys Val Val Lys Phe
    1190                1195                1200

Arg Tyr Phe Thr Asn Glu Gly Val Met Ala Lys Gly Val Thr Val
    1205                1210                1215

Ile Asp Gly Phe Thr Gln Tyr Phe Gly Glu Asp Gly Phe Gln Ala
    1220                1225                1230

Lys Asp Lys Leu Val Thr Phe Lys Gly Lys Thr Tyr Tyr Phe Asp
    1235                1240                1245

Ala His Thr Gly Asn Gly Ile Lys Asp Thr Trp Arg Asn Ile Asn
    1250                1255                1260

Gly Lys Trp Tyr Tyr Phe Asp Ala Asn Gly Val Ala Ala Thr Gly
    1265                1270                1275

Ala Gln Val Ile Asn Gly Gln Lys Leu Tyr Phe Asn Glu Asp Gly
    1280                1285                1290

Ser Gln Val Lys Gly Gly Val Val Lys Asn Ala Asp Gly Thr Tyr
    1295                1300                1305

Ser Lys Tyr Lys Glu Gly Phe Gly Glu Leu Val Thr Asn Glu Phe
    1310                1315                1320

Phe Thr Thr Asp Gly Asn Val Trp Tyr Tyr Ala Gly Ala Asn Gly
    1325                1330                1335

Lys Thr Val Thr Gly Ala Gln Val Ile Asn Gly Gln His Leu Tyr
    1340                1345                1350

Phe Asn Ala Asp Gly Ser Gln Val Lys Gly Gly Val Val Lys Asn
    1355                1360                1365

Ala Asp Gly Thr Tyr Ser Lys Tyr Asn Ala Ser Thr Gly Glu Arg
    1370                1375                1380

Leu Thr Asn Glu Phe Phe Thr Thr Gly Asp Asn Asn Trp Tyr Tyr
    1385                1390                1395

Ile Gly Ala Asn Gly Lys Ser Val Thr Gly Glu Val Lys Ile Gly
    1400                1405                1410

Asp Asp Thr Tyr Phe Phe Ala Lys Asp Gly Lys Gln Val Lys Gly
    1415                1420                1425

Gln Thr Val Ser Ala Gly Asn Gly Arg Ile Ser Tyr Tyr Tyr Gly
    1430                1435                1440

Asp Ser Gly Lys Arg Ala Val Ser Thr Trp Ile Glu Ile Gln Pro
    1445                1450                1455

Gly Val Tyr Val Tyr Phe Asp Lys Asn Gly Leu Ala Tyr Pro Pro
    1460                1465                1470

Arg Val Leu Asn
    1475

<210> SEQ ID NO 3
<211> LENGTH: 4308
<212> TYPE: DNA
```

<213> ORGANISM: Streptococcus sobrinus

<400> SEQUENCE: 3

```
atggttgacg gcaaatacta ctattatgat caggacggta acgtaaagaa gaatttcgcg      60
gtgagcgttg gtgacaaaat ctactacttc gatgaaactg gtgcatataa ggataccagc     120
aaagtggacg ccgacaagag cagcagcgcg gttagccaaa acgcgaccat ctttgcggcg     180
aataaccgtg cgtacagcac ctctgcaaag aattttgaag cggtggataa ctacctgacc     240
gcagacagct ggtatcgtcc gaaatccatc ctgaaggacg caaaacctg gaccgagagc      300
ggtaaggatg atttccgtcc actgctgatg catggtggc ctgacaccga actaagcgc       360
aactacgtga actatatgaa taaagtggtc ggtattgaca agacgtacac tgcggaaacg     420
tcgcaagcgg atttgaccgc agcggcgag ctggttcaag cgcgtatcga gcagaagatt      480
accagcgaaa acaacaccaa atggctgcgc gaagcaatct ccgcgttcgt taagacgcag     540
cctcagtgga acggcgagtc cgaaaagccg tatgacgatc acttgcagaa cggtgcgctg     600
ctgtttgata ccaaaccga cctgacgcca gacacccaaa gcaattaccg tttgctgaac      660
cgtaccccga ccaatcagac tggtagcctg gatagccgtt ttacgtataa tccgaatgac     720
ccgttgggcg gctacgattt cttgctggcg aacgacgttg acaatagcaa tccggtcgtc     780
caggctgaac agttgaactg gctgcattat ctgctgaact ttggctctat ttacgctaac     840
gatgccgacg ccaattttga cagcattcgc gttgatgccg tcgataatgt cgatgctgat     900
ctgctgcaaa tcagcagcga ttacctgaaa gcagcgtatg gcatcgacaa gaataacaag     960
aatgcgaaca ccatgttag catcgtcgaa gcgtggagcg acaatgatac cccgtatttg     1020
cacgacgatg gcgataatct gatgaacatg gacaacaaat ttcgcctgtc catgctgtgg     1080
agcctggcaa agccgctgga caaacgtagc ggttttgaacc cgctgattca aatagcctg     1140
gtggaccgcg aggtggacga tcgtgaagtg gaaaccgtgc cgtcctacag ctttgctcgt     1200
gcacatgata gcgaggtgca ggacatcatc cgtgacatta tcaaggctga gattaaccca     1260
aatagctttg gttatagctt cactcaagaa gagatcgagc aagcctttaa gatttacaac     1320
gaggatttga gaaaaacgga caagaaatac acccactaca atgtgccgct gagctacacc     1380
ctgctgctga ccaacaaggg cagcatcccg cgtgtgtact atggtgatat gttcaccgat     1440
gatggccaat acatggcaaa caagaccgtc aactacgacg caatcgagag cctgctgaaa     1500
gcccgtatga aatatgtcag cggtggccaa gcaatgcaga actatcaaat tggtaatggc     1560
gagattttga ccagcgtgcg ctatggtaaa ggtgccctga gcagagcga taagggtgac     1620
gcgacgacgc gcactagcgg tgttggcgtg gttatgggta atcagccgaa cttctccctg     1680
gacggtaaag ttgtggccct gaatatgggt gcggcccatg cgaatcaaga ataccgtgca     1740
ctgatggtca gcactaaaga cggtgtggca acttacgcaa ccgatgctga cgcatccaaa     1800
gcgggcctgg tcaagcgtac cgacgagaac ggctacctgt acttcctgaa tgatgatctg     1860
aagggcgtcg cgaaccctca ggtttccggc ttcttgcaag tgtgggttcc agttggtgcc     1920
gccgatgacc aggacattcg cgtcgccgcc agcgacacgg cgagcacgga tggtaaaagc     1980
ctgcatcaag atgcggcgat ggacagccgc gtcatgtttg agggtttcag caattttcaa     2040
tccttcgcga ccaaagaaga agaatacacg aatgttgtta tcgcgaacaa tgtcgataag     2100
ttcgttagct ggggtatcac cgattttgaa atggctccgc agtatgttag cagcaccgac     2160
ggtcagttct tggacagcgt catccagaat ggctatgcgt ttactgatcg ctatgatctg     2220
ggtatgtcca aggcgaacaa gtatggcacg gcagaccaac tggttaaggc aatcaaagcc     2280
```

```
ctgcacgcta aaggcctgaa agttatggcg gactgggtcc cggatcaaat gtacaccttt    2340
ccaaaacagg aagttgtgac cgttacccgc accgacaaat tcggtaaacc gatcgccggc    2400
tctcaaatca atcacagctt gtatgtgacc gacaccaaat ccagcggcga cgactaccaa    2460
gcgaagtacg gcggtgcctt cctggatgaa ctgaaagaaa agtacccgga actgttcacg    2520
aaaaagcaaa ttagcacggg ccaagcgatt gatccgagcg tgaaaatcaa gcagtggagc    2580
gcaaaatact tcaatggttc gaatatcctg ggtcgcggtg cggactatgt gctgagcgac    2640
caggtcagca ataagtattt caacgtggcg agcgacacct tgttcctgcc gtccagcctg    2700
ctgggcaagt tcgtggagag cggcattcgt tacgacggca agggttacat ctacaacagc    2760
tccgcgaccg gcgatcaggt caaagcgtct tcattacgg aagccggtaa cctgtattac    2820
ttcggcaaag acggttacat ggttactggt gcccagacga ttaatggcgc caactacttc    2880
ttcctggaaa acggtacggc actgcgtaat acgatttaca ccgatgctca aggtaatagc    2940
cactattacg cgaatgatgg caaacgctat gaaaatggct atcaacagtt cggtaacgat    3000
tggcgctact ttaaagatgg taacatggca gtcggcctga ccacggttga tggcaacgtg    3060
caatactttg acaaagacgg cgtccaggca aaggataaga ttatcgtcac ccgtgatggc    3120
aaggtccgtt acttcgatca gcacaacggt aacgcggcga ccaacacgtt cattgctgat    3180
aaaactggcc attggtatta cctgggtaaa gatggcgtcg cggtgactgg cgcccagacc    3240
gtcggcaaac aaaaaactgta cttcgaggcc aacggtcaac aagttaaagg tgactttgtt    3300
acgtccgatg agggcaaact gtatttctat gacgttgatt ctggtgacat gtggacggac    3360
accttcatcg aggataaggc gggcaactgg ttctatttgg gcaaggatgg tgcggcagtt    3420
acgggtgccc aaacgattcg cggtcagaag ctgtacttca aggccaatgg tcaacaggtc    3480
aagggtgaca ttgttaaggg caccgacggt aaaatccgct actatgatgc aaaatccggt    3540
gaacaggtgt tcaacaaaac ggtgaaagct gcggatggca aaacgtatgt tatcggtaat    3600
gatggtgtcg cggtggaccc tagcgtggtt aaaggtcaaa cctttaagga cgcttcgggc    3660
gctctgcgtt tctacaactt gaagggtcaa ctggtcactg gcagcggctg gtatgaaacc    3720
gcgaaccatg actgggttta cattcagtcc ggcaaggcac tgaccggcga acagaccatt    3780
aacggtcaac acctgtattt caaagaagat ggtcaccaag tcaagggtca gttggtcacg    3840
ggcaccgatg gtaaagtgcg ttactatgac gccaacagcg gtgaccaagc attcaacaag    3900
agcgtcactg tgaatggtaa aacctattac tttggcaacg atggtacggc gcagactgct    3960
ggcaacccga agggtcagac gttcaaggat ggctccgaca tccgtttta ctctatggaa    4020 ggccaactgg tgaccggctc gggttggtac gagaacgcgc aaggccagtg gctgtatgtg    4080
aaaaacggta aggtgctgac tggtctgcaa accgttggca gccagcgtgt ttacttcgac    4140
gagaatggta ttcaggccaa gggcaaagca gtgcgtacca gcgatggcaa aattcgttat    4200
ttcgacgaaa acagcggcag catgatcacg aatcaatgga agttcgtcta tggtcagtat    4260
tactactttg gtaacgacgg tgcacgtatt taccgtggtt ggaactaa                 4308
```

<210> SEQ ID NO 4
<211> LENGTH: 1435
<212> TYPE: PRT
<213> ORGANISM: Streptococcus sobrinus

<400> SEQUENCE: 4

```
Met Val Asp Gly Lys Tyr Tyr Tyr Tyr Asp Gln Asp Gly Asn Val Lys
1               5                   10                  15
```

```
Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
        195                 200                 205

Thr Pro Asp Thr Gln Ser Asn Tyr Arg Leu Leu Asn Arg Thr Pro Thr
            210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270

Asn Phe Gly Ser Ile Tyr Ala Asn Asp Ala Asp Ala Asn Phe Asp Ser
        275                 280                 285

Ile Arg Val Asp Ala Val Asp Asn Val Asp Ala Asp Leu Leu Gln Ile
            290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
        355                 360                 365

Arg Ser Gly Leu Asn Pro Leu Ile His Asn Ser Leu Val Asp Arg Glu
            370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430
```

```
Glu Gln Ala Phe Lys Ile Tyr Asn Glu Asp Leu Lys Lys Thr Asp Lys
            435                 440                 445
Lys Tyr Thr His Tyr Asn Val Pro Leu Ser Tyr Thr Leu Leu Leu Thr
450                 455                 460
Asn Lys Gly Ser Ile Pro Arg Val Tyr Gly Asp Met Phe Thr Asp
465                 470                 475                 480
Asp Gly Gln Tyr Met Ala Asn Lys Thr Val Asn Tyr Asp Ala Ile Glu
                    485                 490                 495
Ser Leu Leu Lys Ala Arg Met Lys Tyr Val Ser Gly Gln Ala Met
                500                 505                 510
Gln Asn Tyr Gln Ile Gly Asn Gly Glu Ile Leu Thr Ser Val Arg Tyr
            515                 520                 525
Gly Lys Gly Ala Leu Lys Gln Ser Asp Lys Gly Asp Ala Thr Thr Arg
        530                 535                 540
Thr Ser Gly Val Gly Val Val Met Gly Asn Gln Pro Asn Phe Ser Leu
545                 550                 555                 560
Asp Gly Lys Val Val Ala Leu Asn Met Gly Ala Ala His Ala Asn Gln
                565                 570                 575
Glu Tyr Arg Ala Leu Met Val Ser Thr Lys Asp Gly Val Ala Thr Tyr
                580                 585                 590
Ala Thr Asp Ala Asp Ala Ser Lys Ala Gly Leu Val Lys Arg Thr Asp
                595                 600                 605
Glu Asn Gly Tyr Leu Tyr Phe Leu Asn Asp Asp Leu Lys Gly Val Ala
            610                 615                 620
Asn Pro Gln Val Ser Gly Phe Leu Gln Val Trp Val Pro Val Gly Ala
625                 630                 635                 640
Ala Asp Asp Gln Asp Ile Arg Val Ala Ala Ser Asp Thr Ala Ser Thr
                    645                 650                 655
Asp Gly Lys Ser Leu His Gln Asp Ala Ala Met Asp Ser Arg Val Met
                660                 665                 670
Phe Glu Gly Phe Ser Asn Phe Gln Ser Phe Ala Thr Lys Glu Glu
            675                 680                 685
Tyr Thr Asn Val Val Ile Ala Asn Asn Val Asp Lys Phe Val Ser Trp
690                 695                 700
Gly Ile Thr Asp Phe Glu Met Ala Pro Gln Tyr Val Ser Ser Thr Asp
705                 710                 715                 720
Gly Gln Phe Leu Asp Ser Val Ile Gln Asn Gly Tyr Ala Phe Thr Asp
                725                 730                 735
Arg Tyr Asp Leu Gly Met Ser Lys Ala Asn Lys Tyr Gly Thr Ala Asp
                740                 745                 750
Gln Leu Val Lys Ala Ile Lys Ala Leu His Ala Lys Gly Leu Lys Val
            755                 760                 765
Met Ala Asp Trp Val Pro Asp Gln Met Tyr Thr Phe Pro Lys Gln Glu
        770                 775                 780
Val Val Thr Val Thr Arg Thr Asp Lys Phe Gly Lys Pro Ile Ala Gly
785                 790                 795                 800
Ser Gln Ile Asn His Ser Leu Tyr Val Thr Asp Thr Lys Ser Ser Gly
                805                 810                 815
Asp Asp Tyr Gln Ala Lys Tyr Gly Gly Ala Phe Leu Asp Glu Leu Lys
                820                 825                 830
Glu Lys Tyr Pro Glu Leu Phe Thr Lys Lys Gln Ile Ser Thr Gly Gln
            835                 840                 845
Ala Ile Asp Pro Ser Val Lys Ile Lys Gln Trp Ser Ala Lys Tyr Phe
```

-continued

```
            850                 855                 860
Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
                    885                 890                 895

Pro Ser Ser Leu Leu Gly Lys Val Val Glu Ser Gly Ile Arg Tyr Asp
                900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
        930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
                    965                 970                 975

Gln Gly Asn Ser His Tyr Tyr Ala Asn Asp Gly Lys Arg Tyr Glu Asn
                980                 985                 990

Gly Tyr Gln Gln Phe Gly Asn Asp Trp Arg Tyr Phe Lys Asp Gly Asn
            995                 1000                1005

Met Ala Val Gly Leu Thr Thr Val Asp Gly Asn Val Gln Tyr Phe
        1010                1015                1020

Asp Lys Asp Gly Val Gln Ala Lys Asp Lys Ile Ile Val Thr Arg
        1025                1030                1035

Asp Gly Lys Val Arg Tyr Phe Asp Gln His Asn Gly Asn Ala Ala
        1040                1045                1050

Thr Asn Thr Phe Ile Ala Asp Lys Thr Gly His Trp Tyr Tyr Leu
        1055                1060                1065

Gly Lys Asp Gly Val Ala Val Thr Gly Ala Gln Thr Val Gly Lys
        1070                1075                1080

Gln Lys Leu Tyr Phe Glu Ala Asn Gly Gln Gln Val Lys Gly Asp
        1085                1090                1095

Phe Val Thr Ser Asp Glu Gly Lys Leu Tyr Phe Tyr Asp Val Asp
        1100                1105                1110

Ser Gly Asp Met Trp Thr Asp Thr Phe Ile Glu Asp Lys Ala Gly
        1115                1120                1125

Asn Trp Phe Tyr Leu Gly Lys Asp Gly Ala Ala Val Thr Gly Ala
        1130                1135                1140

Gln Thr Ile Arg Gly Gln Lys Leu Tyr Phe Lys Ala Asn Gly Gln
        1145                1150                1155

Gln Val Lys Gly Asp Ile Val Lys Gly Thr Asp Gly Lys Ile Arg
        1160                1165                1170

Tyr Tyr Asp Ala Lys Ser Gly Glu Gln Val Phe Asn Lys Thr Val
        1175                1180                1185

Lys Ala Ala Asp Gly Lys Thr Tyr Val Ile Gly Asn Asp Gly Val
        1190                1195                1200

Ala Val Asp Pro Ser Val Val Lys Gly Gln Thr Phe Lys Asp Ala
        1205                1210                1215

Ser Gly Ala Leu Arg Phe Tyr Asn Leu Lys Gly Gln Leu Val Thr
        1220                1225                1230

Gly Ser Gly Trp Tyr Glu Thr Ala Asn His Asp Trp Val Tyr Ile
        1235                1240                1245

Gln Ser Gly Lys Ala Leu Thr Gly Glu Gln Thr Ile Asn Gly Gln
        1250                1255                1260
```

| | | | | | | | | | | |
|---|---|---|---|---|---|---|---|---|---|---|
| His | Leu | Tyr | Phe | Lys | Glu | Asp | Gly | His | Gln | Val | Lys | Gly | Gln | Leu |
| 1265 | | | | 1270 | | | | | 1275 | |

Val Thr Gly Thr Asp Gly Lys Val Arg Tyr Tyr Asp Ala Asn Ser
1280                    1285                    1290

Gly Asp Gln Ala Phe Asn Lys Ser Val Thr Val Asn Gly Lys Thr
1295                    1300                    1305

Tyr Tyr Phe Gly Asn Asp Gly Thr Ala Gln Thr Ala Gly Asn Pro
1310                    1315                    1320

Lys Gly Gln Thr Phe Lys Asp Gly Ser Asp Ile Arg Phe Tyr Ser
1325                    1330                    1335

Met Glu Gly Gln Leu Val Thr Gly Ser Gly Trp Tyr Glu Asn Ala
1340                    1345                    1350

Gln Gly Gln Trp Leu Tyr Val Lys Asn Gly Lys Val Leu Thr Gly
1355                    1360                    1365

Leu Gln Thr Val Gly Ser Gln Arg Val Tyr Phe Asp Glu Asn Gly
1370                    1375                    1380

Ile Gln Ala Lys Gly Lys Ala Val Arg Thr Ser Asp Gly Lys Ile
1385                    1390                    1395

Arg Tyr Phe Asp Glu Asn Ser Gly Ser Met Ile Thr Asn Gln Trp
1400                    1405                    1410

Lys Phe Val Tyr Gly Gln Tyr Tyr Phe Gly Asn Asp Gly Ala
1415                    1420                    1425

Arg Ile Tyr Arg Gly Trp Asn
1430                    1435

<210> SEQ ID NO 5
<211> LENGTH: 4026
<212> TYPE: DNA
<213> ORGANISM: Streptococcus salivarius K12

<400> SEQUENCE: 5

```
atgacggacg taaatactac ttatgtaaat gaggacggca gccacaaaga gaatttcgca    60
attacggtaa acggtcaact gttgtacttt ggcaaggacg cgctctgac gagcagcagc   120
acgcacagct tcacgccggg tactacgaat attgtggacg ttctcgat caacaaccgt   180
gcgtacgata gcagcgaagc gagctttgag ctgatcaacg ttacctgac ggcggattcc   240
tggtatcgcc cggtttctat catcaaggat ggcgtcacgt ggcaggcaag cactgccgag   300
gattttcgtc cgctgttgat ggcctggtgg ccgaacgttg atacccaggt gaactatctg   360
aactatatgt ccaaggtctt taacctggaa gccagtaca ccagcaccga taaacaggct   420
gatctgaacc gtgctgcaaa ggatatccag gtcaagatcg aacagaagat ccaggcggaa   480
aagagcacgc agtggctgcg tgagactatc tccgcgtttg ttaaaaccca gccgcaatgg   540
aacaaagaga ctgagaatta ctccaagggt ggtggcgaag atcatctgca aggcggtgcg   600
ctgttgtacg tgaacgacag ccgtaccccg tgggcgaata gcaattaccg cctgctgaat   660
cgcacggcaa cgaaccagac cggtaccatt aacaagtcgg tgttggacga gcaatccgat   720
ccaaatcaca tgggtggctt cgacttcctg ctggcaaacg atgtggatct gagcaatcct   780
gttgtgcagg ccgagcagct gaatcaaatc cattatctga tgaactgggg cagcattgtt   840
atgggtgaca agacgcgaa ttttgatggt atccgtgtgg acgccgttga caacgtgaac   900
gctgacatgt tgcagctgta cacgaactac tttcgtgagt attacggcgt caacaaaagc   960
gaagcgcaag cgctggcgca cattagcgtt ctggaagcgt ggagcttgaa cgataaccac  1020
```

-continued

```
tataacgaca aaaccgatgg tgcggcactg gcgatggaga ataagcaacg tctggccttg      1080
ctgttctctc tggccaagcc gatcaaagat cgtactccgg cagtgagccc actgtataac      1140
aatactttca ataccaccca acgtgacttc aagacggatt ggattaacaa ggacggtagc      1200
accgcctaca atgaggatgg caccgcgaaa caatctacca tcggtaagta caatgagaaa      1260
tatggtgatg caagcggtaa ctatgtgttt attcgtgccc atgacaataa cgtccaagac      1320
attattgcgg agatcattaa gaaagaaatc aataagaaga gcgatggttt taccatcagc      1380
gatagcgaaa tgaaacaggc gttcgaaatc tacaacaaag atatgctgag cagcaataag      1440
aaatacactc tgaataacat tccggcagcg tacgccgtga tgctgcaaaa catggagact      1500
atcacccgtg tgtattatgg tgacctgtac accgacgacg gtcactatat ggaaaccaag      1560
agcccgtatc atgacaccat tgtgaacctg atgaaaaacc gtatcaagta cgtttctggt      1620
ggccaggccc aacgctccta ttggctgccg accgacggta aaatggacaa tagcgatgtc      1680
gaactgtacc gtactagcga ggtctatacc agcgttcgct acggtaagga cattatgacg      1740
gcggatgaca ccgagggtag caagtactcc cgcacgagcg gtcaggttac cctggttgtt      1800
aacaacccga agctgactct gcatgaaagc gccaaactga acgtcgagat gggtaagatc      1860
cacgcaaacc agaaataccg tgcgctgatt gtgggtaccg ccgatggcat caaaaacttt      1920
acgtctgatg ccgaagcgat cgcggcaggc tacgtaaaag aaacggacag caatggtgtt      1980
ctgaccttcg gcgcaaatga tatcaaaggt tacgagactt tcgatatgag cggtttcgtc      2040
gcagtttggg tgccggtggg tgcgagcgat gatcaggaca tccgcgtggc gccgtcgacg      2100
gaagcgaaga agaaggtgaa actgacgctg aaagccacgg aagcgtatga tagccagttg      2160
atttatgaag gcttctccaa tttccagacc attccggatg gcagcgaccc gagcgtttat      2220
accaaccgca aaattgctga gaatgttgat ctgtttaagt cctggggtgt cactagcttc      2280
gaaatggctc cgcagtttgt ttcggcggac gacggcacct tcctggatag cgttatccag      2340
aacggttacg cctttgcgga ccgttatgat ttggccatga gcaagaacaa caagtacggt      2400
tctaaagagg atctgcgcga cgcactgaaa gcgctgcaca agctggcat tcaggcaatc      2460 gcggactggg tcccagacca aatctaccaa ctgccaggca agaagtggt tacggcgacg      2520 cgcacggacg gtgcgggtcg caagatcgcg gacgccatca ttgatcatag cctgtatgtt      2580
gctaactcca agagctccgg tcgcgattac caagcgcagt atggtggcga gtttctggca      2640
gagctgaaag cgaagtaccc gaaaatgttc acggaaaaca tgattagcac gggtaagccg      2700
atcgatgaca gcgtcaaact gaagcaatgg aaagccaagt atttcaatgg tacgaatgtg      2760
ctggaccgtg gtgtcggtta cgtcctgtcc gacgaggcga ccggcaaata cttcaccgtt      2820
accaaagagg gtaacttcat tccgctgcaa ctgaccggca tgaaaaagc ggtgaccggt      2880 ttcagcaacg acggcaaggg tatcacctac tttggtacga gcggtaatca ggccaagagc      2940
gcgttcgtca cctttaacgg caatacgtac tatttcgacg cgcgtggcca catggtcacg      3000
aacggcgagt atagcccgaa cggcaaagat gtctaccgtt ttctgccaaa tggtattatg      3060
ttgtcgaacg cgttttatgt cgacgcaaac ggtaatacgt acttgtacaa ctacaagggc      3120
cagatgtaca aggtggtta tacgaaattt gatgtcaccg aaactgataa agatggtaat      3180
gagagcaagg tggtcaagtt tcgttatttc accaatgagg gcgtcatggc taagggtctg      3240
accgtcattg acggtagcac ccagtacttt ggtgaggatg ttttcaaac gaaggacaag      3300 ctggcgacct ataaaggtaa gacttattac ttcgaggcac acacgggcaa tgcgatcaaa      3360
aacacctggc gtaacatcga cggtaagtgg tatcacttcg atgagaatgg cgttgccgcg      3420
```

-continued

```
accggtgcac aagtgattaa cggtcaaaaa ctgtatttca acgaggatgg ctcgcaagtg    3480
aagggcggtg ttgttaagaa cgccgacggt acctacagca aatacaaaga gggcagcggt    3540
gagctggtta ccaacgagtt tttcacgacc gacggtaatg tgtggtacta tgctggtgcg    3600
gatggcaaga ctgtgaccgg tgctcaggtc attaatggtc agcacctgta ctttaaagaa    3660
gatggcagcc aggtgaaagg tggtgtggtg aaaaacgcgg acggtacgta cagcaagtat    3720
gacgccgcca ccggtgaacg cttgaccaat gagttcttta ccacgggcga taacaattgg    3780
tactatattg gttctaatgg taagaccgta accggtgaag tcaaaatcgg tgcggacacc    3840
tattactttg ccaaagatgg caaacaggtc aagggccaaa ccgtcaccgc aggcaatggc    3900
cgcatctcct attactacgg cgattctggt aagaaagcaa tcagcacgtg gatcgaaatt    3960
caaccgggta tctatgtcta ttttgataag acgggcatcg cgtacccacc gcgtgtgctg    4020
aattaa                                                              4026
```

<210> SEQ ID NO 6
<211> LENGTH: 1341
<212> TYPE: PRT
<213> ORGANISM: Streptococcus salivarius K12

<400> SEQUENCE: 6

```
Met Thr Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr His Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asn Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Glu Ala Lys Tyr Thr Ser Thr Asp Lys Gln Ala Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn Arg Thr Ala Thr
    210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255
```

-continued

```
Leu Ser Asn Pro Val Val Gln Ala Glu Gln Leu Asn Gln Ile His Tyr
            260                 265                 270
Leu Met Asn Trp Gly Ser Ile Val Met Gly Asp Lys Asp Ala Asn Phe
        275                 280                 285
Asp Gly Ile Arg Val Asp Ala Val Asp Asn Val Asn Ala Asp Met Leu
    290                 295                 300
Gln Leu Tyr Thr Asn Tyr Phe Arg Glu Tyr Tyr Gly Val Asn Lys Ser
305                 310                 315                 320
Glu Ala Gln Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
            340                 345                 350
Glu Asn Lys Gln Arg Leu Ala Leu Leu Phe Ser Leu Ala Lys Pro Ile
        355                 360                 365
Lys Asp Arg Thr Pro Ala Val Ser Pro Leu Tyr Asn Asn Thr Phe Asn
    370                 375                 380
Thr Thr Gln Arg Asp Phe Lys Thr Asp Trp Ile Asn Lys Asp Gly Ser
385                 390                 395                 400
Thr Ala Tyr Asn Glu Asp Gly Thr Ala Lys Gln Ser Thr Ile Gly Lys
                405                 410                 415
Tyr Asn Glu Lys Tyr Gly Asp Ala Ser Gly Asn Tyr Val Phe Ile Arg
            420                 425                 430
Ala His Asp Asn Asn Val Gln Asp Ile Ile Ala Glu Ile Ile Lys Lys
        435                 440                 445
Glu Ile Asn Lys Lys Ser Asp Gly Phe Thr Ile Ser Asp Ser Glu Met
    450                 455                 460
Lys Gln Ala Phe Glu Ile Tyr Asn Lys Asp Met Leu Ser Ser Asn Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
            500                 505                 510
Asp Gly His Tyr Met Glu Thr Lys Ser Pro Tyr His Asp Thr Ile Val
        515                 520                 525
Asn Leu Met Lys Asn Arg Ile Lys Tyr Val Ser Gly Gly Gln Ala Gln
    530                 535                 540
Arg Ser Tyr Trp Leu Pro Thr Asp Gly Lys Met Asp Asn Ser Asp Val
545                 550                 555                 560
Glu Leu Tyr Arg Thr Ser Glu Val Tyr Thr Ser Val Arg Tyr Gly Lys
                565                 570                 575
Asp Ile Met Thr Ala Asp Asp Thr Glu Gly Ser Lys Tyr Ser Arg Thr
            580                 585                 590
Ser Gly Gln Val Thr Leu Val Val Asn Asn Pro Lys Leu Thr Leu His
        595                 600                 605
Glu Ser Ala Lys Leu Asn Val Glu Met Gly Lys Ile His Ala Asn Gln
    610                 615                 620
Lys Tyr Arg Ala Leu Ile Val Gly Thr Ala Asp Gly Ile Lys Asn Phe
625                 630                 635                 640
Thr Ser Asp Ala Glu Ala Ile Ala Ala Gly Tyr Val Lys Glu Thr Asp
                645                 650                 655
Ser Asn Gly Val Leu Thr Phe Gly Ala Asn Asp Ile Lys Gly Tyr Glu
            660                 665                 670
Thr Phe Asp Met Ser Gly Phe Val Ala Val Trp Val Pro Val Gly Ala
```

```
            675                 680                 685
Ser Asp Asp Gln Asp Ile Arg Val Ala Pro Ser Thr Glu Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Asp His Ser Leu Tyr Val Ala Asn Ser Lys
850                 855                 860

Ser Ser Gly Arg Asp Tyr Gln Ala Gln Tyr Gly Gly Glu Phe Leu Ala
865                 870                 875                 880

Glu Leu Lys Ala Lys Tyr Pro Lys Met Phe Thr Glu Asn Met Ile Ser
                885                 890                 895

Thr Gly Lys Pro Ile Asp Asp Ser Val Lys Leu Lys Gln Trp Lys Ala
            900                 905                 910

Lys Tyr Phe Asn Gly Thr Asn Val Leu Asp Arg Gly Val Gly Tyr Val
        915                 920                 925

Leu Ser Asp Glu Ala Thr Gly Lys Tyr Phe Val Thr Lys Glu Gly
930                 935                 940

Asn Phe Ile Pro Leu Gln Leu Thr Gly Asn Glu Lys Ala Val Thr Gly
945                 950                 955                 960

Phe Ser Asn Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
            1010                1015                1020

Ala Phe Tyr Val Asp Ala Asn Gly Asn Thr Tyr Leu Tyr Asn Tyr
            1025                1030                1035

Lys Gly Gln Met Tyr Lys Gly Gly Tyr Thr Lys Phe Asp Val Thr
            1040                1045                1050

Glu Thr Asp Lys Asp Gly Asn Glu Ser Val Val Lys Phe Arg
            1055                1060                1065

Tyr Phe Thr Asn Glu Gly Val Met Ala Lys Gly Leu Thr Val Ile
            1070                1075                1080

Asp Gly Ser Thr Gln Tyr Phe Gly Glu Asp Gly Phe Gln Thr Lys
            1085                1090                1095
```

| Asp | Lys | Leu | Ala | Thr | Tyr | Lys | Gly | Lys | Thr | Tyr | Tyr | Phe | Glu | Ala |
| | 1100 | | | | 1105 | | | | | 1110 | | | | |

| His | Thr | Gly | Asn | Ala | Ile | Lys | Asn | Thr | Trp | Arg | Asn | Ile | Asp | Gly |
| | 1115 | | | | 1120 | | | | | 1125 | | | | |

| Lys | Trp | Tyr | His | Phe | Asp | Glu | Asn | Gly | Val | Ala | Ala | Thr | Gly | Ala |
| | 1130 | | | | 1135 | | | | | 1140 | | | | |

| Gln | Val | Ile | Asn | Gly | Gln | Lys | Leu | Tyr | Phe | Asn | Glu | Asp | Gly | Ser |
| | 1145 | | | | 1150 | | | | | 1155 | | | | |

| Gln | Val | Lys | Gly | Gly | Val | Val | Lys | Asn | Ala | Asp | Gly | Thr | Tyr | Ser |
| | 1160 | | | | 1165 | | | | | 1170 | | | | |

| Lys | Tyr | Lys | Glu | Gly | Ser | Gly | Glu | Leu | Val | Thr | Asn | Glu | Phe | Phe |
| | 1175 | | | | 1180 | | | | | 1185 | | | | |

| Thr | Thr | Asp | Gly | Asn | Val | Trp | Tyr | Tyr | Ala | Gly | Ala | Asp | Gly | Lys |
| | 1190 | | | | 1195 | | | | | 1200 | | | | |

| Thr | Val | Thr | Gly | Ala | Gln | Val | Ile | Asn | Gly | Gln | His | Leu | Tyr | Phe |
| | 1205 | | | | 1210 | | | | | 1215 | | | | |

| Lys | Glu | Asp | Gly | Ser | Gln | Val | Lys | Gly | Gly | Val | Val | Lys | Asn | Ala |
| | 1220 | | | | 1225 | | | | | 1230 | | | | |

| Asp | Gly | Thr | Tyr | Ser | Lys | Tyr | Asp | Ala | Ala | Thr | Gly | Glu | Arg | Leu |
| | 1235 | | | | 1240 | | | | | 1245 | | | | |

| Thr | Asn | Glu | Phe | Phe | Thr | Thr | Gly | Asp | Asn | Asn | Trp | Tyr | Tyr | Ile |
| | 1250 | | | | 1255 | | | | | 1260 | | | | |

| Gly | Ser | Asn | Gly | Lys | Thr | Val | Thr | Gly | Glu | Val | Lys | Ile | Gly | Ala |
| | 1265 | | | | 1270 | | | | | 1275 | | | | |

| Asp | Thr | Tyr | Tyr | Phe | Ala | Lys | Asp | Gly | Lys | Gln | Val | Lys | Gly | Gln |
| | 1280 | | | | 1285 | | | | | 1290 | | | | |

| Thr | Val | Thr | Ala | Gly | Asn | Gly | Arg | Ile | Ser | Tyr | Tyr | Tyr | Gly | Asp |
| | 1295 | | | | 1300 | | | | | 1305 | | | | |

| Ser | Gly | Lys | Lys | Ala | Ile | Ser | Thr | Trp | Ile | Glu | Ile | Gln | Pro | Gly |
| | 1310 | | | | 1315 | | | | | 1320 | | | | |

| Ile | Tyr | Val | Tyr | Phe | Asp | Lys | Thr | Gly | Ile | Ala | Tyr | Pro | Pro | Arg |
| | 1325 | | | | 1330 | | | | | 1335 | | | | |

| Val | Leu | Asn |
| | 1340 | |

```
<210> SEQ ID NO 7
<211> LENGTH: 4023
<212> TYPE: DNA
<213> ORGANISM: Streptococcus salivarius PS4

<400> SEQUENCE: 7
atgattgacg gcaaatacta ctacgtaaac aaagatggct cgcacaaaga gaatttcgca      60
attaccgtga atggtcagtt gttgtatttc ggtaaggacg gtgcattgac gtctagcagc     120
acctacagct ttacgcaggg caccaccaac atcgttgatg gctttagcaa aaacaaccgt     180
gcgtacgatt ccagcgaggc gagctttgaa ctgatcgacg ttatctgac cgcggactcc     240 tggtatcgtc cggtgagcat tatcaaggac ggcgttacgt ggcaagccag caccaaagag     300
gactttcgcc gctgctgat ggcctggtgg ccgaatgttg acacccaggt caactacctg     360
aattacatgt cgaaggtgtt taacctggac gcgaagtata cgagcaccga caaacaggtt     420
gacctgaatc gcgcagccaa ggacattcag gttaagattg agcaaaagat tcaggccgag     480
aagagcactc aatggctgcg tgaagcgatt tcggccttcg tcaaaaccca gccgcagtgg     540
aataaagaaa cggagaactt ctccaagggt ggtggtgagg atcatctgca aggtggtgca     600
```

```
ctgctgtacg ttaacgaccc gcgtaccccg tgggctaact ccaactaccg cctgctgaat     660
cgtactgcga ccaaccagac cggcacgatc gacaagagcg ttctggacga acagagcgat     720
cctaaccaca tgggcggctt cgattttctg ctggcgaatg acgtcgatac cagcaatccg     780
gtggtgcagg cggaacaact gaatcagatc cactacctga tgaattgggg ttccattgtt     840
atgggcgaca agatgcaaa  cttcgatggt atccgcgtgg acgcggtcga taacgttgac     900
gcagatatgc tgcaactgta caccaactac tttcgtgagt attatggcgt gaacaaaagc     960
gaggcaaacg ctttggcgca catctcggtg ctggaagcgt ggagcttgaa tgataatcac    1020
tataatgaca agactgacgg tgcggccctg gcgatggaga caaacagcg  tttggccctg    1080
ctgtttagct tggcgaaacc gatcaaagaa cgtacccctg cggtgagccc gctgtacaac    1140
aacactttca cacgacgca  gcgtgacgaa agaccgatt  ggattaacaa agacggtagc    1200
aaagcctata atgaggacgg caccgtcaag cagtccacca tcggcaagta caacgagaaa    1260
tacgcgacgc cgtccggcaa ttatgtgttc attcgcgccc acgataacaa cgtccaagac    1320
attattgcag agatcattaa gaaagaaatc aatccgaaaa gcgacggttt caccattacc    1380
gacgccgaaa tgaaaaaggc attcgaaatc tacaacaaag atatgctgtc ctctgataag    1440
aaatacaccc tgaacaacat cccagcggcc tacgcggtga tgctgcaaaa catggaaacc    1500
attactcgtg tgtattacgg cgatctgtat accgacgatg ccattacat  ggaaaccaag    1560
agcccgtact acgacaccat tgtgaacctg atgaagaacc gtatcaaata cgtgtccggt    1620
ggtcaagcgc aacgttccta ttggctgccg accgacggta agtggataa  agcgatgtc     1680
gaactgtatc gcaccaacga ggtgtacacc agcgtccgtt acggtaagga catcatgact    1740
gccgatgaca cccaaggtag caagtacagc cgtaccagcg gtcaggtgac cctggtggtg    1800
aacaacccga gctgtctttt ggataagagc gcgaagctgg acgtcgaaat gggcaagatc    1860
catgcaaacc agaaataccg tgctctgatc gtgggtacgc cgaacggcat caaaaacttc    1920
acgagcgacg ccgaggcaat cgcggctggc tacgtgaaag aaaccgacgg caatggtgtg    1980
ctgaccttcg gtgcaaatga catcaaaggt tacgaaacgt ttgacatgag cggtttcgtt    2040
gcagtttggg ttccggtagg tgcaagcgat gatcaagaca tccgtgtcgc cgcaagcacc    2100
gcggcaaaga aagaaggtga gctgactttg aaggcaactg aggcgtatga ctctcagctg    2160
atttacgaag gttttttcgaa ttttcagacc attccggatg gtagcgatcc gagcgtttac    2220
accaatcgta agatcgcgga aaatgttgat ttgttcaaga gctggggtgt gacctctttc    2280
gaaatggcgc cacagtttgt gagcgcagac gacggtacgt ttctggacag cgttatccag    2340
aacggctatg cgtttgcgga ccgttatgat ctggcgatgt ccaaaaacaa taagtacggt    2400
tcgaaagaag atctgcgtaa cgcgttgaag ctttgcaca  aggccggcat ccaagccatt    2460
gcggactggg ttccggatca gatctaccaa ctgccgggca agaagtagt  gaccgccact    2520
cgtaccgatg tgccggtcg  taagattagc gatgcaatta tcgatcacag cctgtacgtc    2580
gcaaacagca agtcgtctgg caaagactat caagctaaat acggtggtga gttcctggcc    2640
gagctgaaag caaagtaccc ggaaatgttt aaagtcaaca tgattagcac gggtaaaccg    2700
atcgacgact ctgtcaaact gaagcaatgg aaggcggagt actttaacgg tacgaatgtt    2760
ctggaccgtg gtgttggtta cgtcctgagc gatgaggcga cggcaagta  ctttaccgtt    2820
acgaaagagg gtaactttat cccactgcaa ttgaaaggta acgagaaagt tatcacgggc    2880
ttcagctctg acggcaaggg cattacctat ttcggcacct cgggtaatca agcgaaaagc    2940
```

-continued

```
gcttttgtca cgttcaatgg taatacctac tattttgacg cgcgtggcca catggttacc    3000
aacggcgaat atagccctaa tggtaaggat gtgtatcgtt tcctgccgaa tggtattatg    3060
ttgagcaatg cattctacgt tgacggtaac ggcaatacct acctgtacaa ctccaagggc    3120
caaatgtaca aggtggttta tagcaaattc gacgttacgg aaaccaaaga tggtaaagag    3180
agcaaagtgg tgaaatttcg ctactttacc aatgaaggtg tgatggcaaa aggtgttacc    3240
gtggtggacg gcttcactca atacttcaac gaagatggca ttcagagcaa ggacgaactg    3300
gtgacctaca atggtaaaac ctattacttc gaagcgcata ccggtaatgc gatcaaaaac    3360
acgtggcgca atatcaaggg taagtggtat cactttgatg cgaatggcgt ggcggcaacg    3420
ggtgcacagg ttatcaatgg tcagcacctg tactttaatg aggatggttc ccaggtgaag    3480
ggtggcgtcg tgaagaatgc ggatggtacc ttcagcaagt ataaagatgg ttccggtgac    3540
ctggtggtca atgagttctt cactactggt gataacgtgt ggtactacgc tggtgccaac    3600
ggcaaaactg tgacgggtgc ccaggtcatc aatggccaac acctgttttt caaagaggac    3660
ggtagccagg ttaagggtga tttcgttaag aacagcgacg gcacctactc taagtatgat    3720
gcggccagcg gcgaacgcct gacgaatgag ttttttcacga ccggtgacaa ccactggtac    3780
tatattggtg ccaatggcaa aaccgttacc ggcgaagtca gatcggtga tgatacgtac    3840
ttcttcgcaa agatggcaa gcagctgaag ggccagatcg tgacgacccg cagcggtcgt    3900
atcagctact acttcggcga ctctggtaag aaggcgatta gcacctgggt ggagattcag    3960
ccgggtgttt tcgtgttttt cgacaaaaat ggcctggcat atccgccgga aacatgaat    4020
taa                                                                    4023
```

<210> SEQ ID NO 8
<211> LENGTH: 1340
<212> TYPE: PRT
<213> ORGANISM: Streptococcus salivarius PS4

<400> SEQUENCE: 8

```
Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Lys Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Lys Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Val Asp Leu Asn Arg
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Ala Ile Ser Ala Phe Val Lys Thr
                165                 170                 175
```

```
Gln Pro Gln Trp Asn Lys Glu Thr Glu Asn Phe Ser Lys Gly Gly
                180                 185                 190

Glu Asp His Leu Gln Gly Gly Ala Leu Leu Tyr Val Asn Asp Pro Arg
            195                 200                 205

Thr Pro Trp Ala Asn Ser Asn Tyr Arg Leu Leu Asn Arg Thr Ala Thr
        210                 215                 220

Asn Gln Thr Gly Thr Ile Asp Lys Ser Val Leu Asp Glu Gln Ser Asp
225                 230                 235                 240

Pro Asn His Met Gly Gly Phe Asp Phe Leu Ala Asn Asp Val Asp
                245                 250                 255

Thr Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
        290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
            325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
            405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
            515                 520                 525

Asn Leu Met Lys Asn Arg Ile Lys Tyr Val Ser Gly Gly Gln Ala Gln
            530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
            565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Ser Leu Asp
```

```
                 595                 600                 605
Lys Ser Ala Lys Leu Asp Val Glu Met Gly Lys Ile His Ala Asn Gln
610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
            675                 680                 685

Ser Asp Asp Gln Asp Ile Arg Val Ala Ala Ser Thr Ala Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
                820                 825                 830

Gly Lys Glu Val Val Thr Ala Thr Arg Thr Asp Gly Ala Gly Arg Lys
            835                 840                 845

Ile Ser Asp Ala Ile Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Asp Arg Gly Val Gly Tyr Val
            915                 920                 925

Leu Ser Asp Glu Ala Thr Gly Lys Tyr Phe Thr Val Thr Lys Glu Gly
930                 935                 940

Asn Phe Ile Pro Leu Gln Leu Lys Gly Asn Glu Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                 1000                 1005

Lys Asp Val Tyr Arg Phe Leu Pro Asn Gly Ile Met Leu Ser Asn
    1010                 1015                 1020
```

Ala Phe Tyr Val Asp Gly Asn Gly Asn Thr Tyr Leu Tyr Asn Ser
1025                1030                1035

Lys Gly Gln Met Tyr Lys Gly Gly Tyr Ser Lys Phe Asp Val Thr
1040                1045                1050

Glu Thr Lys Asp Gly Lys Glu Ser Lys Val Val Lys Phe Arg Tyr
1055                1060                1065

Phe Thr Asn Glu Gly Val Met Ala Lys Gly Val Thr Val Val Asp
1070                1075                1080

Gly Phe Thr Gln Tyr Phe Asn Glu Asp Gly Ile Gln Ser Lys Asp
1085                1090                1095

Glu Leu Val Thr Tyr Asn Gly Lys Thr Tyr Tyr Phe Glu Ala His
1100                1105                1110

Thr Gly Asn Ala Ile Lys Asn Thr Trp Arg Asn Ile Lys Gly Lys
1115                1120                1125

Trp Tyr His Phe Asp Ala Asn Gly Val Ala Ala Thr Gly Ala Gln
1130                1135                1140

Val Ile Asn Gly Gln His Leu Tyr Phe Asn Glu Asp Gly Ser Gln
1145                1150                1155

Val Lys Gly Gly Val Val Lys Asn Ala Asp Gly Thr Phe Ser Lys
1160                1165                1170

Tyr Lys Asp Gly Ser Gly Asp Leu Val Val Asn Glu Phe Phe Thr
1175                1180                1185

Thr Gly Asp Asn Val Trp Tyr Tyr Ala Gly Ala Asn Gly Lys Thr
1190                1195                1200

Val Thr Gly Ala Gln Val Ile Asn Gly Gln His Leu Phe Phe Lys
1205                1210                1215

Glu Asp Gly Ser Gln Val Lys Gly Asp Phe Val Lys Asn Ser Asp
1220                1225                1230

Gly Thr Tyr Ser Lys Tyr Asp Ala Ala Ser Gly Glu Arg Leu Thr
1235                1240                1245

Asn Glu Phe Phe Thr Thr Gly Asp Asn His Trp Tyr Tyr Ile Gly
1250                1255                1260

Ala Asn Gly Lys Thr Val Thr Gly Glu Val Lys Ile Gly Asp Asp
1265                1270                1275

Thr Tyr Phe Phe Ala Lys Asp Gly Lys Gln Leu Lys Gly Gln Ile
1280                1285                1290

Val Thr Thr Arg Ser Gly Arg Ile Ser Tyr Tyr Phe Gly Asp Ser
1295                1300                1305

Gly Lys Lys Ala Ile Ser Thr Trp Val Glu Ile Gln Pro Gly Val
1310                1315                1320

Phe Val Phe Asp Lys Asn Gly Leu Ala Tyr Pro Pro Glu Asn
1325                1330                1335

Met Asn
1340

<210> SEQ ID NO 9
<211> LENGTH: 3972
<212> TYPE: DNA
<213> ORGANISM: Streptococcus dentirousetti

<400> SEQUENCE: 9
atggttgacg gcaaatacta ctactacgat gcagacggca acgtaaagaa aaacttcgcg      60
gttagcgttg gcgatgccat tttctatttt gatgaaacgg gtgcctacaa agataccagc     120

```
aaagttgatg cggataagac cagctctagc gtcaatcaga ccacggaaac gttcgcagcg    180
aataaccgtg cgtatagcac cgcagccgag aactttgaag cgattgataa ctacctgact    240
gcggatagct ggtatcgtcc gaagtctatc ttgaaagatg gtacgacgtg gaccgaaagc    300
accaaggatg attttcgccc gctgctgatg gcgtggtggc cggataccga aaccaaacgt    360
aactacgtga actatatgaa caaggtggtc ggtatcgaca aaacgtacac cgcggaaacg    420
tcccaagctg acctgacggc ggcagccgaa ctggtgcagg cgcgtatcga gcagaaaatc    480
actagcgaaa agaatacgaa gtggctgcgt gaggcgattt ccgcgttcgt taagactcaa    540
ccgcagtgga atggcgagag cgagaaacct tatgatgacc acctgcaaaa tggtgcgctg    600
aagttcgaca atgaaaccag cctgaccccg gatacgcaga gcggctatcg catcctgaac    660
cgtaccccga cgaatcaaac cggtagcctg acccgcgct tcacctttaa tcagaatgac    720
ccgctgggtg gttatgagta tttgctggct aatgatgtcg ataacagcaa cccggtcgtt    780
caggccgaga gcctgaactg gctgcattac ctgctgaatt ttggtagcat ttacgcgaat    840
gatccggagg ccaatttcga cagcatccgt gtggacgcgg tggacaatgt tgacgcagac    900
ctgctgcaaa ttagctcgga ttacctgaaa tcggcgtaca aaattgacaa gaacaacaaa    960
aatgcgaacg accacgttag catcgtcgag gcgtggagcg acaatgatac cccgtacctg   1020
aatgatgatg cgacaatct gatgaacatg gataacaagt ttcgtctgag catgctgtgg   1080
agcctggcga agccaaccaa tgtccgtagc ggcttgaatc cgctgatcca acacagcgtg   1140
gttgaccgtg aggtggacga ccgtgaagtt gaggctaccc cgaattacag ctttgcacgc   1200
gcacacgaca gcgaagttca agatttgatt cgcgacatca tcaaagctga gatcaaccca   1260
aacagcttcg gttatagctt tacccaagag gaaatcgacc aggccttcaa gatctacaat   1320
gaggatttga gaaaaccaa taagaagtat acccactaca acgtcccgct gagctacacc   1380
ctgctgctga cgaacaaggg cagcattcca cgcatttact acggtgacat gtttacggat   1440
gacggtcagt atatggccaa caaaaccgtt aactatgacg ccattgagag cctgctgaaa   1500
gcacgtatga agtatgttag cggtggccaa gcgatgcaga attacaacat cggcaacggc   1560
gagattctga ccagcgtccg ttacggtaag ggtgccctga acagagcga caaaggcgat   1620 aagactactc gtaccagcgg tattggcgtt gtgatgggta accagagcaa tttcagcctg   1680
gagggcaagg tggtggccct gaatatgggt gcaacgcata ccaaacagaa gtatcgtgca   1740
ttgatggtgt ctacggaaac cggcgtggcg atttacaata gcgatgaaga agcagaggca   1800
gcaggcctga tcaaaacgac cgatgagaat ggttatttgt actttctgaa tgacgatctg   1860
aagggcgtgg ctaacccgca ggtcagcggc ttcctgcaag tgtgggttcc ggttggtgca   1920
ccggctgacc aggacattcg tgtggcggcg accgatgcgg cttctaccga cggtaagagc   1980
ctgcatcagg acgcagctct ggattctcgc gtcatgtttg aaggtttcag caacttccag   2040
agcttcgcaa ccaaggaaga ggaatacacc aacgttgtta ttgcaaagaa cgtggataag   2100
ttcgtgagct ggggtatcac cgacttcgag atggcaccgc agtacgttag ctctaccgat   2160
ggcacctttc tggatagcgt gattcaaaat ggctatgcct ttacggaccg ttacgacctg   2220
ggtatgagca aagcaaacaa gtatggtact gctgaccaac tggtggccgc gattaaagcg   2280
ctgcatgcga agggtctgcg tgtgatggcg gattgggtcc cagatcaaat gtacactttc   2340
cctaagaagg aagtggttac cgttacccgt acggacaaat ttggcaatcc agtggcaggc   2400
agccaaatca ccacaccttt gtacgtcact gatactaagg gtagcggtga cgactaccag   2460
gcgaagtacg gtggcgcatt cctggatgaa ctgaaagaaa agtacccgga gctgtttacc   2520
```

```
aagaagcaaa tcagcaccgg tcaggcaatc gacccgagcg tgaaaatcaa gcagtggagc    2580
gcgaagtact tcaacggtag caatatcttg ggtcgcggtg cgaactacgt gctgtccgac    2640
caggcgtcta acaagtactt taacgtggcc gaaggtaaag tctttctgcc agcggcgatg    2700
ctgggtaagg tcgtcgagag cggtatccgt ttcgacggta aaggttatat ctataacagc    2760
agcaccactg gcgaacaagt gaaggacagc ttcattaccg aagcgggtaa cttgtactat    2820
tttggcaaag atggttatat ggtcatgggt gcacagaata tccagggtgc taactactac    2880
ttcttggcga atggtgcggc cctgcgcaat agcatcctga cggatcagga tggcaaaagc    2940
cactattatg caaatgacgg caagcgttat gagaacggct actatcaatt cggtaacgac    3000
tcctggcgct attttgaaaa cggcgttatg ccgttggtt tgacgcgcgt tgcgggccac    3060
gaccaatact ttgataagga tggtatccaa gcgaagaata agatcattgt tacgcgtgac    3120
ggtaaggtcc gctacttcga cgaacacaac ggcaatgctg ccacgaatac gtttatcagc    3180
gatcaagccg ccattggta ctacctgggt aaagatggtg tcgccgtgac gggtgcgcag    3240
accgttggca agcaacacct gtacttcgag gctaacggcc aacaagtaaa aggcgatttt    3300
gttaccgcca aggacggtaa gttgtatttt ctggacggtg actctggcga catgtggacc    3360
gataccttcg tccaggataa ggctggtcat tggttctatc tgggcaaaga cggtgcggcg    3420
gtaaccggtg cccagaccgt ccgtggtcag aagctgtact tcaaagcgaa tggccagcag    3480
gttaagggtg acattgtgaa aggcgcggat ggtaaaatcc gttactatga tgcaaattcc    3540
ggtgaccagg tttacaatcg cacggtgaaa ggctccgacg gcaagaccta tatcattggt    3600
aatgacggcg tcgcaatcac gcaaaccatc gccaaaggcc agaccatcaa ggatggcagc    3660
gttctgcgct tctatagcat ggagggtcag ctggtgaccg gcagcggctg gtattccaac    3720
gcgaaaggtc aatggttgta tgtcaagaac ggtcaagtcc tgacgggttt gcagacggtg    3780
ggcagccagc gtgtgtactt tgacgcaaat ggtattcaag cgaaaggtaa agcagtgcgt    3840
acctccgatg gcaaactgcg ttacttcgat gcgaacagcg gcagcatgat caccaatcag    3900
tggaaagaag ttaatggtca gtactactat ttcgacaaca acggtgttgc gatctatcgc    3960
ggttggaact aa                                                        3972
```

<210> SEQ ID NO 10
<211> LENGTH: 1323
<212> TYPE: PRT
<213> ORGANISM: Streptococcus dentirousetti

<400> SEQUENCE: 10

```
Met Val Asp Gly Lys Tyr Tyr Tyr Asp Ala Asp Gly Asn Val Lys
1               5                   10                  15

Lys Asn Phe Ala Val Ser Val Gly Asp Ala Ile Phe Tyr Phe Asp Glu
                20                  25                  30

Thr Gly Ala Tyr Lys Asp Thr Ser Lys Val Asp Ala Asp Lys Thr Ser
            35                  40                  45

Ser Ser Val Asn Gln Thr Thr Glu Thr Phe Ala Ala Asn Asn Arg Ala
        50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110
```

```
Trp Pro Asp Thr Glu Thr Lys Arg Asn Tyr Val Asn Tyr Met Asn Lys
            115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Lys Pro Tyr Asp
        180                 185                 190

Asp His Leu Gln Asn Gly Ala Leu Lys Phe Asp Asn Glu Thr Ser Leu
            195                 200                 205

Thr Pro Asp Thr Gln Ser Gly Tyr Arg Ile Leu Asn Arg Thr Pro Thr
        210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
        290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu Asn Asp Asp Gly Asp Asn Leu Met Asn Met Asp Asn
            340                 345                 350

Lys Phe Arg Leu Ser Met Leu Trp Ser Leu Ala Lys Pro Thr Asn Val
        355                 360                 365

Arg Ser Gly Leu Asn Pro Leu Ile His Asn Ser Val Val Asp Arg Glu
        370                 375                 380

Val Asp Asp Arg Glu Val Glu Ala Thr Pro Asn Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asn Lys
        435                 440                 445

Lys Tyr Thr His Tyr Asn Val Pro Leu Ser Tyr Thr Leu Leu Leu Thr
        450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gln Ala Met
            500                 505                 510

Gln Asn Tyr Asn Ile Gly Asn Gly Glu Ile Leu Thr Ser Val Arg Tyr
            515                 520                 525
```

```
Gly Lys Gly Ala Leu Lys Gln Ser Asp Lys Gly Asp Lys Thr Thr Arg
530                 535                 540
Thr Ser Gly Ile Gly Val Val Met Gly Asn Gln Ser Asn Phe Ser Leu
545                 550                 555                 560
Glu Gly Lys Val Val Ala Leu Asn Met Gly Ala Thr His Thr Lys Gln
                565                 570                 575
Lys Tyr Arg Ala Leu Met Val Ser Thr Glu Thr Gly Val Ala Ile Tyr
            580                 585                 590
Asn Ser Asp Glu Ala Glu Ala Gly Leu Ile Lys Thr Thr Asp
        595                 600                 605
Glu Asn Gly Tyr Leu Tyr Phe Leu Asn Asp Leu Lys Gly Val Ala
    610                 615                 620
Asn Pro Gln Val Ser Gly Phe Leu Gln Val Trp Val Pro Val Gly Ala
625                 630                 635                 640
Pro Ala Asp Gln Asp Ile Arg Val Ala Ala Thr Asp Ala Ala Ser Thr
                645                 650                 655
Asp Gly Lys Ser Leu His Gln Asp Ala Ala Leu Asp Ser Arg Val Met
            660                 665                 670
Phe Glu Gly Phe Ser Asn Phe Gln Ser Phe Ala Thr Lys Glu Glu Glu
            675                 680                 685
Tyr Thr Asn Val Val Ile Ala Lys Asn Val Asp Lys Phe Val Ser Trp
690                 695                 700
Gly Ile Thr Asp Phe Glu Met Ala Pro Gln Tyr Val Ser Ser Thr Asp
705                 710                 715                 720
Gly Thr Phe Leu Asp Ser Val Ile Gln Asn Gly Tyr Ala Phe Thr Asp
                725                 730                 735
Arg Tyr Asp Leu Gly Met Ser Lys Ala Asn Lys Tyr Gly Thr Ala Asp
            740                 745                 750
Gln Leu Val Ala Ala Ile Lys Ala Leu His Ala Lys Gly Leu Arg Val
        755                 760                 765
Met Ala Asp Trp Val Pro Asp Gln Met Tyr Thr Phe Pro Lys Lys Glu
    770                 775                 780
Val Val Thr Val Thr Arg Thr Asp Lys Phe Gly Asn Pro Val Ala Gly
785                 790                 795                 800
Ser Gln Ile Asn His Thr Leu Tyr Val Thr Asp Thr Lys Gly Ser Gly
                805                 810                 815
Asp Asp Tyr Gln Ala Lys Tyr Gly Gly Ala Phe Leu Asp Glu Leu Lys
            820                 825                 830
Glu Lys Tyr Pro Glu Leu Phe Thr Lys Lys Gln Ile Ser Thr Gly Gln
        835                 840                 845
Ala Ile Asp Pro Ser Val Lys Ile Lys Gln Trp Ser Ala Lys Tyr Phe
    850                 855                 860
Asn Gly Ser Asn Ile Leu Gly Arg Gly Ala Asn Tyr Val Leu Ser Asp
865                 870                 875                 880
Gln Ala Ser Asn Lys Tyr Phe Asn Val Ala Glu Gly Lys Val Phe Leu
                885                 890                 895
Pro Ala Ala Met Leu Gly Lys Val Val Glu Ser Gly Ile Arg Phe Asp
            900                 905                 910
Gly Lys Gly Tyr Ile Tyr Asn Ser Ser Thr Thr Gly Glu Gln Val Lys
        915                 920                 925
Asp Ser Phe Ile Thr Glu Ala Gly Asn Leu Tyr Tyr Phe Gly Lys Asp
    930                 935                 940
Gly Tyr Met Val Met Gly Ala Gln Asn Ile Gln Gly Ala Asn Tyr Tyr
```

```
945                 950                 955                 960
Phe Leu Ala Asn Gly Ala Ala Leu Arg Asn Ser Ile Leu Thr Asp Gln
                965                 970                 975
Asp Gly Lys Ser His Tyr Tyr Ala Asn Asp Gly Lys Arg Tyr Glu Asn
                    980                 985                 990
Gly Tyr Tyr Gln Phe Gly Asn Asp Ser Trp Arg Tyr Phe Glu Asn Gly
            995                 1000                1005
Val Met Ala Val Gly Leu Thr Arg Val Ala Gly His Asp Gln Tyr
    1010                1015                1020
Phe Asp Lys Asp Gly Ile Gln Ala Lys Asn Lys Ile Ile Val Thr
    1025                1030                1035
Arg Asp Gly Lys Val Arg Tyr Phe Asp Glu His Asn Gly Asn Ala
    1040                1045                1050
Ala Thr Asn Thr Phe Ile Ser Asp Gln Ala Gly His Trp Tyr Tyr
    1055                1060                1065
Leu Gly Lys Asp Gly Val Ala Val Thr Gly Ala Gln Thr Val Gly
    1070                1075                1080
Lys Gln His Leu Tyr Phe Glu Ala Asn Gly Gln Gln Val Lys Gly
    1085                1090                1095
Asp Phe Val Thr Ala Lys Asp Gly Lys Leu Tyr Phe Leu Asp Gly
    1100                1105                1110
Asp Ser Gly Asp Met Trp Thr Asp Thr Phe Val Gln Asp Lys Ala
    1115                1120                1125
Gly His Trp Phe Tyr Leu Gly Lys Asp Gly Ala Ala Val Thr Gly
    1130                1135                1140
Ala Gln Thr Val Arg Gly Gln Lys Leu Tyr Phe Lys Ala Asn Gly
    1145                1150                1155
Gln Gln Val Lys Gly Asp Ile Val Lys Gly Ala Asp Gly Lys Ile
    1160                1165                1170
Arg Tyr Tyr Asp Ala Asn Ser Gly Asp Gln Val Tyr Asn Arg Thr
    1175                1180                1185
Val Lys Gly Ser Asp Gly Lys Thr Tyr Ile Ile Gly Asn Asp Gly
    1190                1195                1200
Val Ala Ile Thr Gln Thr Ile Ala Lys Gly Gln Thr Ile Lys Asp
    1205                1210                1215
Gly Ser Val Leu Arg Phe Tyr Ser Met Glu Gly Gln Leu Val Thr
    1220                1225                1230
Gly Ser Gly Trp Tyr Ser Asn Ala Lys Gly Gln Trp Leu Tyr Val
    1235                1240                1245
Lys Asn Gly Gln Val Leu Thr Gly Leu Gln Thr Val Gly Ser Gln
    1250                1255                1260
Arg Val Tyr Phe Asp Ala Asn Gly Ile Gln Ala Lys Gly Lys Ala
    1265                1270                1275
Val Arg Thr Ser Asp Gly Lys Leu Arg Tyr Phe Asp Ala Asn Ser
    1280                1285                1290
Gly Ser Met Ile Thr Asn Gln Trp Lys Glu Val Asn Gly Gln Tyr
    1295                1300                1305
Tyr Tyr Phe Asp Asn Asn Gly Val Ala Ile Tyr Arg Gly Trp Asn
    1310                1315                1320

<210> SEQ ID NO 11
<211> LENGTH: 4026
<212> TYPE: DNA
<213> ORGANISM: Streptococcus salivarius SK126
```

<400> SEQUENCE: 11

```
atgatcgacg gcaaatacta ttatgttaat gaggacggta gccacaaaga aaactttgcg      60
attacggtta atggtcaact gctgtatttc ggtaaggacg gcgcactgac ctctagcagc     120
acttacagct ttaccccagg tacgacgaac atcgtggatg gcttttctat caacaaccgc     180
gcgtatgact ccagcgaagc gtcctttgaa ctgattgatg gctacttgac tgccgactcc     240
tggtatcgtc cggcttccat catcaaggac ggtgtcacgt ggcaggccag caccgcagag     300
gactttcgcc cgctgctgat ggcgtggtgg ccaaacgtgg atacccaggt gaactatctg     360
aactacatgt ctaaagtgtt taacctggac gcaaagtata gcagcaccga taaacaagag     420
actctgaagg ttgcagctaa ggatattcag attaagatcg agcagaaaat tcaggcggag     480
aaaagcaccc aatggctgcg cgaaacgatc agcgcttttg tgaaaaccca accacagtgg     540
aacaaagaga ctgagaatta ctcgaaaggt ggtggtgagg atcatctgca aggcggtgca     600
ctgctgtacg tgaatgatag ccgtaccccg tgggcaaata gcgattatcg ccgcctgaac     660
cgcaccgcta ccaatcaaac gggtacgatt gacaagtcca ttctggacga gcagagcgac     720
ccaaatcaca tgggcggttt cgacttcctg ctggcgaatg atgttgacct gtccaacccg     780
gttgtgcagg cagagcagct gaaccagatt cactacttga tgaattgggg ctctatcgtg     840
atgggtgaca agacgcaaa cttttgatggt atccgtgtcg atgcagttga caacgtcgat     900
gccgacatgc tgcaactgta taccaactac ttccgtgaat actacggtgt taacaaaagc     960
gaagcgaacg cactggcgca cattagcgtt ttggaagcgt ggagcttgaa tgataatcac    1020
tacaacgaca aaaccgatgg tgcagcattg gcgatggaga ataagcagcg tctggcgctg    1080
ctgtttagcc tggctaaacc gattaaagag cgcaccccgg cagtgagccc gctgtataac    1140
aacaccttca atacgaccca acgcgatgag aaaaccgact ggatcaataa agacggttct    1200
aaggcctata cgaggatgg tactgtgaag cagagccaca ttggtaagta caatgaaaaa    1260
tatggtgatg catcgggcaa ttatgtgttc atccgtgccc atgataacaa tgtccaagac    1320
atcattgcgg agatcattaa gaaagaaatc aacccgaaaa gcgatggttt caccatcact    1380
gacgccgaaa tgaaacaagc gttcgagatt tacaataagg acatgctgag cagcgacaag    1440
aagtacaccc tgaataacat cccggcagct tatgccgtga tgttgcagaa catggaaacg    1500
attacccgtg tctattatgg tgacctgtac accgacgacg gccactacat ggaaccaag    1560
tccccgtatt acgacaccat cgttaacctg atgaaaagcc gtatcaagta cgtcagcggt    1620
ggccaggccc aacgtagcta ctggctgccg accgacggca gatggacaa tagcgacgtt    1680
gagctgtatc gcaccaacga agtgtatacc agcgtccgtt acggtaaaga cattatgacc    1740
gcgaacgata ccgagggtag caagtacagc cgcaccagcg gccaggtcac cctggttgca    1800
aacaacccga gctgaccct ggaccagagc gcgaagctga atgtggaaat gggtaagatt    1860
cacgcgaatc agaaatacccg tgccctgatt gtgggcacgg ctgacggtat caagaatttc    1920
accagcgacg cagatgctat cgcggcaggc tacgtgaaag aaaccgactc caatggcgtt    1980
ctgacttttg gcgctaatga catcaaaggt tatgaaacct cgacatgtc cggctttgtt    2040
gctgtttggg tgccggtcgg cgcgagcgat gatcaggaca ttcgtgtcgc tcctagcact    2100
gaggccaaga agagggtga attgaccctg aaagcgaccg aagcatacga ttcccagctg    2160
atctatgaag gttttagcaa ttttcaaacc atcccggatg gtagcgaccc gagcgtgtac    2220
accaatcgca agatcgcaga gaacgtggac ctgttcaagt cctggggtgt tacctcgttt    2280
```

```
gaaatggcac cgcagttcgt ttccgcagat gatggcactt ttctggactc tgtgatccaa    2340
aacggctatg cgtttgccga tcgttacgat ttggcgatga gcaagaacaa caaatacggc    2400
agcaaagagg acttgcgtga cgcgctgaaa gccctgcata aagcaggcat ccaggcgatt    2460
gcagactggg tcccggacca gatttatcag ttgccgggca agaagtggt cacggcgact     2520 cgcaccgacg gcgcaggccg taaaatcgcg gacgcgatca ttgatcatag cctgtacgtt    2580
gcgaacacta agagcagcgg caaagattac caggcgaagt acggtggtga gttcttggcg    2640
gagctgaagg ccaagtaccc ggagatgttc aaagtgaaca tgatttctac cggcaaaccg    2700
attgatgaca cgtcaaaact gaaacagtgg aaagcagaat actttaacgg caccaacgtc    2760
ttggagcgcg gtgtgggtta tgtcctgagc gatgaagcca cgggtaaata ctttaccgtc    2820
acgaaggatg caacttcat tccgttgcag ctgacgggta tgagaaagt cgtgaccggc      2880 tttagcaatg atggcaaagg tatcacctac ttcggtacga gcggcactca agcgaaatct    2940
gcgttcgtta cgttcaatgg taatacttac tattttgacg ctcgtggtca catggttacg    3000
aacggcgagt attcgccgaa cggtaaggat gtttaccgtt tcctgccgaa tggtattatg    3060
ctgtctaacg cttttttacgt tgatgcaaat ggtaacacgt acctgtacaa cagcaagggc    3120
caaatgtaca aaggcggtta caccaaattt gacgttaccg aaacggacaa agatggtaag   3180
gaaagcaagg tggtgaagtt tcgttacttt acgaacgaag gtgtcatggc aaaaggcgtt    3240
accgtgattg acggcttcac gcaatacttt ggtgaagatg gtttccaagc gaaagacaag    3300
ctggtcacgt tcaagggcaa gacgtactac ttcgatgcac acaccggcaa tgcgatcaag    3360
gacacctggc gtaatatcaa tggcaagtgg tatcatttcg acgcgaacgg cgttgcagcg    3420
accggcgctc aggtcatcaa tggccaaaaa ctgtatttca cgaggacgg cagccaagtg    3480 aaaggcggtg ttgtcaaaaa cgcggacggt acgtattcta aatacaaaga gggttctggt    3540
gaactggtta ccaacgagtt cttcacgacg gatggcaatg tttggtacta cgcaggcgcg    3600
aatggcaaga ccgttacggg tgcccaggtg attaacggcc aacacctgta cttcaatgcg    3660
gacggttcgc aagtgaaggg cggtgtggtc aagaacgcgg atggcaccta tagcaaatat    3720
gatgcgtcta ccggcgaacg cctgaccaat gagttttca ccacggtga taacaactgg      3780 tactacattg gcgcaaacgg caagagcgtg acgggcgagg tcaagatcgg tgacgatacc    3840
tatttctttg ccaaagatgg caagcaagtt aagggtcaaa ctgtcagcgc gggtaacggt    3900
cgtattagct actactatgg tgatagcggt aagcgtgcgg tgagcacttg gatcgaaatc    3960
caaccgggtg tttatgtcta cttcgacaag aacggcattg cctatccgcc tcgtgtgctg    4020
aattaa                                                               4026
```

<210> SEQ ID NO 12
<211> LENGTH: 1341
<212> TYPE: PRT
<213> ORGANISM: Streptococcus salivarius SK126

<400> SEQUENCE: 12

```
Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60
```

```
Ser Glu Ala Ser Phe Glu Leu Ile Asp Gly Tyr Leu Thr Ala Asp Ser
 65                  70                  75                  80

Trp Tyr Arg Pro Ala Ser Ile Ile Lys Asp Gly Val Thr Trp Gln Ala
                 85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asp Tyr Arg Arg Leu Asn Arg Thr Ala Thr
    210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Pro Lys Ser Asp Gly Phe Thr Ile Thr Asp Ala Glu Met
    450                 455                 460

Lys Gln Ala Phe Glu Ile Tyr Asn Lys Asp Met Leu Ser Ser Asp Lys
465                 470                 475                 480
```

```
Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
    850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
```

-continued

```
            900             905             910
Glu Tyr Phe Asn Gly Thr Asn Val Leu Glu Arg Gly Val Gly Tyr Val
        915             920             925
Leu Ser Asp Glu Ala Thr Gly Lys Tyr Phe Thr Val Thr Lys Asp Gly
        930             935             940
Asn Phe Ile Pro Leu Gln Leu Thr Gly Asn Glu Lys Val Val Thr Gly
945             950             955             960
Phe Ser Asn Asp Gly Lys Gly Ile Thr Tyr Phe Gly Thr Ser Gly Thr
            965             970             975
Gln Ala Lys Ser Ala Phe Val Thr Phe Asn Gly Asn Thr Tyr Tyr Phe
        980             985             990
Asp Ala Arg Gly His Met Val Thr Asn Gly Glu Tyr Ser Pro Asn Gly
        995             1000            1005
Lys Asp Val Tyr Arg Phe Leu Pro Asn Gly Ile Met Leu Ser Asn
        1010            1015            1020
Ala Phe Tyr Val Asp Ala Asn Gly Asn Thr Tyr Leu Tyr Asn Ser
        1025            1030            1035
Lys Gly Gln Met Tyr Lys Gly Gly Tyr Thr Lys Phe Asp Val Thr
        1040            1045            1050
Glu Thr Asp Lys Asp Gly Lys Glu Ser Lys Val Val Lys Phe Arg
        1055            1060            1065
Tyr Phe Thr Asn Glu Gly Val Met Ala Lys Gly Val Thr Val Ile
        1070            1075            1080
Asp Gly Phe Thr Gln Tyr Phe Gly Glu Asp Gly Phe Gln Ala Lys
        1085            1090            1095
Asp Lys Leu Val Thr Phe Lys Gly Lys Thr Tyr Tyr Phe Asp Ala
        1100            1105            1110
His Thr Gly Asn Ala Ile Lys Asp Thr Trp Arg Asn Ile Asn Gly
        1115            1120            1125
Lys Trp Tyr His Phe Asp Ala Asn Gly Val Ala Ala Thr Gly Ala
        1130            1135            1140
Gln Val Ile Asn Gly Gln Lys Leu Tyr Phe Asn Glu Asp Gly Ser
        1145            1150            1155
Gln Val Lys Gly Gly Val Val Lys Asn Ala Asp Gly Thr Tyr Ser
        1160            1165            1170
Lys Tyr Lys Glu Gly Ser Gly Glu Leu Val Thr Asn Glu Phe Phe
        1175            1180            1185
Thr Thr Asp Gly Asn Val Trp Tyr Tyr Ala Gly Ala Asn Gly Lys
        1190            1195            1200
Thr Val Thr Gly Ala Gln Val Ile Asn Gly Gln His Leu Tyr Phe
        1205            1210            1215
Asn Ala Asp Gly Ser Gln Val Lys Gly Gly Val Val Lys Asn Ala
        1220            1225            1230
Asp Gly Thr Tyr Ser Lys Tyr Asp Ala Ser Thr Gly Glu Arg Leu
        1235            1240            1245
Thr Asn Glu Phe Phe Thr Thr Gly Asp Asn Asn Trp Tyr Tyr Ile
        1250            1255            1260
Gly Ala Asn Gly Lys Ser Val Thr Gly Glu Val Lys Ile Gly Asp
        1265            1270            1275
Asp Thr Tyr Phe Phe Ala Lys Asp Gly Lys Gln Val Lys Gly Gln
        1280            1285            1290
Thr Val Ser Ala Gly Asn Gly Arg Ile Ser Tyr Tyr Tyr Gly Asp
        1295            1300            1305
```

```
Ser Gly Lys Arg Ala Val Ser Thr Trp Ile Glu Ile Gln Pro Gly
    1310                1315                1320

Val Tyr Val Tyr Phe Asp Lys Asn Gly Ile Ala Tyr Pro Pro Arg
    1325                1330                1335

Val Leu Asn
    1340

<210> SEQ ID NO 13
<211> LENGTH: 2718
<212> TYPE: DNA
<213> ORGANISM: Streptococcus salivarius

<400> SEQUENCE: 13
atgggtttct caataaataa ccgtgcctac gattcatctg aagctagctt tgaattgatt      60
gatggttatt tgactgcaga tagctggtac cgtccagctt ctatcatcaa agatggtgta     120
acttggcaag catcaactgc agaagatttc cgtccacttt tgatggcttg gtggccaaat     180
gtagatacac aagttaacta cttgaactac atgtctaaag tatttaactt ggatgctaaa     240
tattcaagta cagataagca agaaactttg aaagttgctg ctaaggacat tcaaatcaag     300
attgagcaaa gattcaggc tgaaaaatca acacaatggt tgcgtgaaac tatctctgcc     360
tttgttaaga cacaaccaca atggaacaaa gaaactgaaa actactctaa aggtggcggc     420
gaagatcacc ttcaaggtgg tgcccttctt tatgtgaatg attcacgtac accatgggcg     480
aattctgact atcgtcgttt gaaccgtaca gcaactaacc agactggtac aattgataaa     540
tcaattcttg atgagcaatc agatccaaac cacatgggtg tttcgactt cttgctagct     600
aatgacgtag atttgtcaaa cccagttgtt caagcggaac aattgaacca atccactac     660
cttatgaact ggggttcaat cgttatgggt gacaaggat ctaacttcga tggtatccgt     720
gtcgacgcgg tagataatgt cgatgcagac atgcttcaac tctacacaaa ctacttccgt     780
gagtactatg tgttaacaa atctgaagca aacgctcttg ctcacatctc agtccttgaa     840
gcatggagcc ttaatgacaa ccactacaat gacaagacag atggcgctgc gcttgctatg     900
gaaaacaaac aacgtttggc tctcctcttc tcattggcta aaccaatcaa gaacgtaca     960
ccagctgtaa gtccttgta taacaatact ttcaacacga cacaacgtga tgaaaagact    1020
gattggatta caaagatgg aagcaaggcc tataacgaag acggaacagt taacagtct    1080
acaatcggta aatataacga gaaatacgga gatgcgtcag gaaattacgt ctttatccgt    1140
gcccatgata caacgttca agatattatt gctgaaatca tcaagaaaga aatcaatcca    1200
aaatcagatg gtttcacgat tactgatgct gaaatgaagc aagcctttga gatttacaac    1260
aaagacatgc tcagcagcga caaaaaatat acgcttaaca catcccagc ggcttacgcg    1320
gttatgttgc aaaacatgga aactatcact cgtgtctact atggagacct ttatacagat    1380
gatggtcact acatggaaac taagtctcca tattacgata ccattgttaa cttgatgaag    1440
agtcgtatca gtatgtatc tggtgggcaa gcacaacgtt catactggtt gccaactgat    1500
ggtaagatgg acaattcaga tgttgaactt taccgcacaa atgaagtcta cacttcagta    1560
cgttatggta aagacattat gacagctaat gatacagaag ttctaaata cagccgtact    1620
tctggtcagg taacacttgt agctaacaat ccaaaattga atttggatca atcagctaaa    1680
cttaatgttg aaatgggtaa atccatgcc aaccaaaaat accgtgcttt gattgttggt    1740
acagctgatg gtatcaagaa ctttacatct gatgcagatg caatcgcagc aggttacgtt    1800
aaagaaacag acagcaacgg tgtcttgact ttcggtgcta atgacatcaa gggttatgaa    1860
```

```
acatttgata tgtctggttt cgtagcagtt tgggttccag ttggagcttc agataatcaa   1920
gatatccgag tagcgccttc aacagaagct aaaaaagagg gtgaattgac tcttaaagcg   1980
actgaagctt atgattcaca attaatctac gaaggcttct ctaactttca aactattcca   2040
gatggttcag atccttcagt ctatactaac cgtaagattg ctgaaaatgt tgatttgttc   2100
aaatcatggg gtgtaacatc atttgaaatg cacctcaat ttgtatctgc tgacgatggt   2160
accttccttg actcagttat ccaaaatggt tatgcctttg cagaccgtta cgatcttgcc   2220
atgagtaaga caataaata cggttctaaa gaagatctac gtgatgctct taaagcactt   2280
cataaggctg gtattcaagc aatcgctgac tgggttccag accaaattta ccaattgcca   2340
ggtaaagaag ttgtaacagc gactcgtact gatggtgctg gtcgtaagat tgcggacgct   2400
atcattgacc actcacttta tgtggctaac tctaagtcat caggcaaaga ttaccaagct   2460
aaatacggtg gtgaattctt ggctgaactt aaagctaagt accctgaaat gttcaaggta   2520
aacatgattt caactggtaa accaattgat gattctgtta aattgaaaca atggaaggct   2580
gaatacttca acggaacaaa cgttcttgaa cgtggtgttg ctatgtact agcgatgaa    2640 gcaactggta gtatttcac tgtcactaaa gaaggtaact tcattcctct tcaattgaca   2700
ggtaaagaaa aggtttaa                                                 2718

<210> SEQ ID NO 14
<211> LENGTH: 905
<212> TYPE: PRT
<213> ORGANISM: Streptococcus salivarius

<400> SEQUENCE: 14

Met Gly Phe Ser Ile Asn Asn Arg Ala Tyr Asp Ser Ser Glu Ala Ser
1               5                   10                  15

Phe Glu Leu Ile Asp Gly Tyr Leu Thr Ala Asp Ser Trp Tyr Arg Pro
                20                  25                  30

Ala Ser Ile Ile Lys Asp Gly Val Thr Trp Gln Ala Ser Thr Ala Glu
            35                  40                  45

Asp Phe Arg Pro Leu Leu Met Ala Trp Trp Pro Asn Val Asp Thr Gln
        50                  55                  60

Val Asn Tyr Leu Asn Tyr Met Ser Lys Val Phe Asn Leu Asp Ala Lys
65                  70                  75                  80

Tyr Ser Ser Thr Asp Lys Gln Glu Thr Leu Lys Val Ala Ala Lys Asp
                85                  90                  95

Ile Gln Ile Lys Ile Glu Gln Lys Ile Gln Ala Glu Lys Ser Thr Gln
            100                 105                 110

Trp Leu Arg Glu Thr Ile Ser Ala Phe Val Lys Thr Gln Pro Gln Trp
        115                 120                 125

Asn Lys Glu Thr Glu Asn Tyr Ser Lys Gly Gly Glu Asp His Leu
    130                 135                 140

Gln Gly Gly Ala Leu Leu Tyr Val Asn Asp Ser Arg Thr Pro Trp Ala
145                 150                 155                 160

Asn Ser Asp Tyr Arg Arg Leu Asn Arg Thr Ala Thr Asn Gln Thr Gly
                165                 170                 175

Thr Ile Asp Lys Ser Ile Leu Asp Glu Gln Ser Asp Pro Asn His Met
            180                 185                 190

Gly Gly Phe Asp Phe Leu Leu Ala Asn Asp Val Asp Leu Ser Asn Pro
        195                 200                 205

Val Val Gln Ala Glu Gln Leu Asn Gln Ile His Tyr Leu Met Asn Trp
```

```
              210                 215                 220
Gly Ser Ile Val Met Gly Asp Lys Asp Ala Asn Phe Asp Gly Ile Arg
225                 230                 235                 240

Val Asp Ala Val Asp Asn Val Asp Ala Asp Met Leu Gln Leu Tyr Thr
                    245                 250                 255

Asn Tyr Phe Arg Glu Tyr Tyr Gly Val Asn Lys Ser Glu Ala Asn Ala
                260                 265                 270

Leu Ala His Ile Ser Val Leu Glu Ala Trp Ser Leu Asn Asp Asn His
            275                 280                 285

Tyr Asn Asp Lys Thr Asp Gly Ala Ala Leu Ala Met Glu Asn Lys Gln
        290                 295                 300

Arg Leu Ala Leu Leu Phe Ser Leu Ala Lys Pro Ile Lys Glu Arg Thr
305                 310                 315                 320

Pro Ala Val Ser Pro Leu Tyr Asn Asn Thr Phe Asn Thr Thr Gln Arg
                    325                 330                 335

Asp Glu Lys Thr Asp Trp Ile Asn Lys Asp Gly Ser Lys Ala Tyr Asn
                340                 345                 350

Glu Asp Gly Thr Val Lys Gln Ser Thr Ile Gly Lys Tyr Asn Glu Lys
            355                 360                 365

Tyr Gly Asp Ala Ser Gly Asn Tyr Val Phe Ile Arg Ala His Asp Asn
        370                 375                 380

Asn Val Gln Asp Ile Ile Ala Glu Ile Lys Lys Glu Ile Asn Pro
385                 390                 395                 400

Lys Ser Asp Gly Phe Thr Ile Thr Asp Ala Glu Met Lys Gln Ala Phe
                    405                 410                 415

Glu Ile Tyr Asn Lys Asp Met Leu Ser Ser Asp Lys Lys Tyr Thr Leu
                420                 425                 430

Asn Asn Ile Pro Ala Ala Tyr Ala Val Met Leu Gln Asn Met Glu Thr
            435                 440                 445

Ile Thr Arg Val Tyr Tyr Gly Asp Leu Tyr Thr Asp Asp Gly His Tyr
        450                 455                 460

Met Glu Thr Lys Ser Pro Tyr Tyr Asp Thr Ile Val Asn Leu Met Lys
465                 470                 475                 480

Ser Arg Ile Lys Tyr Val Ser Gly Gly Gln Ala Gln Arg Ser Tyr Trp
                    485                 490                 495

Leu Pro Thr Asp Gly Lys Met Asn Ser Asp Val Glu Leu Tyr Arg
                500                 505                 510

Thr Asn Glu Val Tyr Thr Ser Val Arg Tyr Gly Lys Asp Ile Met Thr
            515                 520                 525

Ala Asn Asp Thr Glu Gly Ser Lys Tyr Ser Arg Thr Ser Gly Gln Val
        530                 535                 540

Thr Leu Val Ala Asn Asn Pro Lys Leu Asn Leu Asp Gln Ser Ala Lys
545                 550                 555                 560

Leu Asn Val Glu Met Gly Lys Ile His Ala Asn Gln Lys Tyr Arg Ala
                    565                 570                 575

Leu Ile Val Gly Thr Ala Asp Gly Ile Lys Asn Phe Thr Ser Asp Ala
                580                 585                 590

Asp Ala Ile Ala Ala Gly Tyr Val Lys Glu Thr Asp Ser Asn Gly Val
            595                 600                 605

Leu Thr Phe Gly Ala Asn Asp Ile Lys Gly Tyr Glu Thr Phe Asp Met
        610                 615                 620

Ser Gly Phe Val Ala Val Trp Val Pro Val Gly Ala Ser Asp Asn Gln
625                 630                 635                 640
```

```
Asp Ile Arg Val Ala Pro Ser Thr Glu Ala Lys Lys Glu Gly Glu Leu
                645                 650                 655

Thr Leu Lys Ala Thr Glu Ala Tyr Asp Ser Gln Leu Ile Tyr Glu Gly
        660                 665                 670

Phe Ser Asn Phe Gln Thr Ile Pro Asp Gly Ser Asp Pro Ser Val Tyr
    675                 680                 685

Thr Asn Arg Lys Ile Ala Glu Asn Val Asp Leu Phe Lys Ser Trp Gly
690                 695                 700

Val Thr Ser Phe Glu Met Ala Pro Gln Phe Val Ser Ala Asp Asp Gly
705                 710                 715                 720

Thr Phe Leu Asp Ser Val Ile Gln Asn Gly Tyr Ala Phe Ala Asp Arg
                725                 730                 735

Tyr Asp Leu Ala Met Ser Lys Asn Asn Lys Tyr Gly Ser Lys Glu Asp
            740                 745                 750

Leu Arg Asp Ala Leu Lys Ala Leu His Lys Ala Gly Ile Gln Ala Ile
        755                 760                 765

Ala Asp Trp Val Pro Asp Gln Ile Tyr Gln Leu Pro Gly Lys Glu Val
    770                 775                 780

Val Thr Ala Thr Arg Thr Asp Gly Ala Gly Arg Lys Ile Ala Asp Ala
785                 790                 795                 800

Ile Ile Asp His Ser Leu Tyr Val Ala Asn Ser Lys Ser Ser Gly Lys
                805                 810                 815

Asp Tyr Gln Ala Lys Tyr Gly Gly Glu Phe Leu Ala Glu Leu Lys Ala
            820                 825                 830

Lys Tyr Pro Glu Met Phe Lys Val Asn Met Ile Ser Thr Gly Lys Pro
        835                 840                 845

Ile Asp Asp Ser Val Lys Leu Lys Gln Trp Lys Ala Glu Tyr Phe Asn
    850                 855                 860

Gly Thr Asn Val Leu Glu Arg Gly Val Gly Tyr Val Leu Ser Asp Glu
865                 870                 875                 880

Ala Thr Gly Lys Tyr Phe Thr Val Thr Lys Glu Gly Asn Phe Ile Pro
                885                 890                 895

Leu Gln Leu Thr Gly Lys Glu Lys Val
            900                 905

<210> SEQ ID NO 15
<211> LENGTH: 2556
<212> TYPE: DNA
<213> ORGANISM: Streptococcus dentirousetti

<400> SEQUENCE: 15
atgacgttcg cagcgaataa ccgtgcgtat agcaccgcag ccgagaactt tgaagcgatt      60
gataactacc tgactgcgga tagctggtat cgtccgaagt ctatcttgaa agatggtacg     120
acgtggaccg aaagcaccaa ggatgatttt cgcccgctgc tgatggcgtg gtggccggat     180
accgaaacca acgtaacta cgtgaactat atgaacaagg tggtcggtat cgacaaaacg     240
tacaccgcgg aaacgtccca agctgacctg acggcggcag ccgaactggt gcaggcgcgt     300
atcgagcaga aaatcactag cgaaaagaat acgaagtggc tgcgtgaggc gatttccgcg     360
ttcgttaaga ctcaaccgca gtggaatggc gagagcgaga accttatga tgaccacctg      420 caaaatggtg cgctgaagtt cgacaatgaa accagcctga ccccggatac gcagagcggc     480
tatcgcatcc tgaaccgtac cccgacgaat caaaccggta gcctggaccc cgcgcttcacc   540 tttaatcaga tgacccgct gggtggttat gagtatttgc tggctaatga tgtcgataac     600
```

```
agcaacccgg tcgttcaggc cgagagcctg aactggctgc attacctgct gaattttggt    660
agcatttacg cgaatgatcc ggaggccaat ttcgacagca tccgtgtgga cgcggtggac    720
aatgttgacg cagacctgct gcaaattagc tcggattacc tgaaatcggc gtacaaaatt    780
gacaagaaca acaaaaatgc gaacgaccac gttagcatcg tcgaggcgtg gagcgacaat    840 gatacccgt acctgaatga tgatggcgac aatctgatga acatggataa caagtttcgt     900
ctgagcatgc tgtggagcct ggcgaagcca accaatgtcc gtagcggctt gaatccgctg    960
atccacaaca gcgtggttga ccgtgaggtg gacgaccgtg aagttgaggc tacccccgaat   1020 tacagctttg cacgcgcaca cgacagcgaa gttcaagatt tgattcgcga catcatcaaa   1080
gctgagatca acccaaacag cttcggttat agctttaccc aagaggaaat cgaccaggcc   1140
ttcaagatct acaatgagga tttgaagaaa accaataaga agtataccca ctacaacgtc   1200
ccgctgagct acaccctgct gctgacgaac aagggcagca ttccacgcat ttactacggt   1260
gacatgttta cggatgacgg tcagtatatg ccaacaaaa ccgttaacta tgacgccatt    1320
gagagcctgc tgaaagcacg tatgaagtat gttagcggtg ccaagcgat gcagaattac    1380 aacatcggca cggcgagat tctgaccagc gtccgttacg gtaagggtgc cctgaaacag    1440
agcgacaaag gcgataagac tactcgtacc agcggtattg gcgttgtgat gggtaaccag   1500
agcaatttca gcctggaggg caaggtggtg gccctgaata tgggtgcaac gcataccaaa   1560
cagaagtatc gtgcattgat ggtgtctacg gaaaccggcg tggcgattta caatagcgat   1620
gaagaagcag aggcagcagg cctgatcaaa cgaccgatg agaatggtta tttgtacttt    1680
ctgaatgacg atctgaaggg cgtggctaac ccgcaggtca gcggcttcct gcaagtgtgg   1740
gttccggttg gtgcaccggc tgaccaggac attcgtgtgg cggcgaccga tgcggcttct   1800
accgacggta agagcctgca tcaggacgca gctctggatt ctcgcgtcat gtttgaaggt   1860
ttcagcaact tccagagctt cgcaaccaag gaagaggaat acaccaacgt tgttattgca   1920
aagaacgtgg ataagttcgt gagctggggt atcaccgact tcgagatggc accgcagtac   1980
gttagctcta ccgatggcac ctttctggat agcgtgattc aaaatggcta tgcctttacg   2040
gaccgttacg acctgggtat gagcaaagca aacaagtatg tgactgctga ccaactggtg   2100
gccgcgatta aagcgctgca tgcgaagggt ctgcgtgtga tggcggattg ggtcccagat   2160
caaatgtaca ctttccctaa gaaggaagtg gttaccgtta cccgtacgga caaatttggc   2220
aatccagtgg caggcagcca aatcaaccac accttgtacg tcactgatac taagggtagc   2280
ggtgacgact accaggcgaa gtacggtggc gcattcctgg atgaactgaa agaaaagtac   2340
ccggagctgt ttaccaagaa gcaaatcagc accggtcagg caatcgaccc gagcgtgaaa   2400
atcaagcagt ggagcgcgaa gtacttcaac ggtagcaata tcttgggtcg cggtgcgaac   2460
tacgtgctgt ccgaccaggc gtctaacaag tactttaacg tggccgaagg taaagtcttt   2520
ctgccagcgg cgatgctggg taaggtcgtc gagtaa                            2556
```

<210> SEQ ID NO 16
<211> LENGTH: 851
<212> TYPE: PRT
<213> ORGANISM: Streptococcus dentirousetti

<400> SEQUENCE: 16

Met Thr Phe Ala Ala Asn Asn Arg Ala Tyr Ser Thr Ala Ala Glu Asn
1               5                   10                  15

Phe Glu Ala Ile Asp Asn Tyr Leu Thr Ala Asp Ser Trp Tyr Arg Pro

```
                20                  25                  30
Lys Ser Ile Leu Lys Asp Gly Thr Thr Trp Thr Glu Ser Thr Lys Asp
            35                  40                  45

Asp Phe Arg Pro Leu Leu Met Ala Trp Trp Pro Asp Thr Glu Thr Lys
        50                  55                  60

Arg Asn Tyr Val Asn Tyr Met Asn Lys Val Val Gly Ile Asp Lys Thr
65                  70                  75                  80

Tyr Thr Ala Glu Thr Ser Gln Ala Asp Leu Thr Ala Ala Glu Leu
            85                  90                  95

Val Gln Ala Arg Ile Glu Gln Lys Ile Thr Ser Glu Lys Asn Thr Lys
            100                 105                 110

Trp Leu Arg Glu Ala Ile Ser Ala Phe Val Lys Thr Gln Pro Gln Trp
            115                 120                 125

Asn Gly Glu Ser Glu Lys Pro Tyr Asp Asp His Leu Gln Asn Gly Ala
        130                 135                 140

Leu Lys Phe Asp Asn Glu Thr Ser Leu Thr Pro Asp Thr Gln Ser Gly
145                 150                 155                 160

Tyr Arg Ile Leu Asn Arg Thr Pro Thr Asn Gln Thr Gly Ser Leu Asp
                165                 170                 175

Pro Arg Phe Thr Phe Asn Gln Asn Asp Pro Leu Gly Gly Tyr Glu Tyr
            180                 185                 190

Leu Leu Ala Asn Asp Val Asp Asn Ser Asn Pro Val Val Gln Ala Glu
            195                 200                 205

Ser Leu Asn Trp Leu His Tyr Leu Leu Asn Phe Gly Ser Ile Tyr Ala
        210                 215                 220

Asn Asp Pro Glu Ala Asn Phe Asp Ser Ile Arg Val Asp Ala Val Asp
225                 230                 235                 240

Asn Val Asp Ala Asp Leu Leu Gln Ile Ser Ser Asp Tyr Leu Lys Ser
                245                 250                 255

Ala Tyr Lys Ile Asp Lys Asn Asn Lys Asn Ala Asn Asp His Val Ser
            260                 265                 270

Ile Val Glu Ala Trp Ser Asp Asn Asp Thr Pro Tyr Leu Asn Asp Asp
            275                 280                 285

Gly Asp Asn Leu Met Asn Met Asp Asn Lys Phe Arg Leu Ser Met Leu
        290                 295                 300

Trp Ser Leu Ala Lys Pro Thr Asn Val Arg Ser Gly Leu Asn Pro Leu
305                 310                 315                 320

Ile His Asn Ser Val Val Asp Arg Glu Val Asp Asp Arg Glu Val Glu
                325                 330                 335

Ala Thr Pro Asn Tyr Ser Phe Ala Arg Ala His Asp Ser Glu Val Gln
            340                 345                 350

Asp Leu Ile Arg Asp Ile Ile Lys Ala Glu Ile Asn Pro Asn Ser Phe
            355                 360                 365

Gly Tyr Ser Phe Thr Gln Glu Glu Ile Asp Gln Ala Phe Lys Ile Tyr
        370                 375                 380

Asn Glu Asp Leu Lys Lys Thr Asn Lys Lys Tyr Thr His Tyr Asn Val
385                 390                 395                 400

Pro Leu Ser Tyr Thr Leu Leu Leu Thr Asn Lys Gly Ser Ile Pro Arg
                405                 410                 415

Ile Tyr Tyr Gly Asp Met Phe Thr Asp Asp Gly Gln Tyr Met Ala Asn
            420                 425                 430

Lys Thr Val Asn Tyr Asp Ala Ile Glu Ser Leu Leu Lys Ala Arg Met
            435                 440                 445
```

```
Lys Tyr Val Ser Gly Gly Gln Ala Met Gln Asn Tyr Asn Ile Gly Asn
    450                 455                 460

Gly Glu Ile Leu Thr Ser Val Arg Tyr Gly Lys Gly Ala Leu Lys Gln
465                 470                 475                 480

Ser Asp Lys Gly Asp Lys Thr Thr Arg Thr Ser Gly Ile Gly Val Val
                485                 490                 495

Met Gly Asn Gln Ser Asn Phe Ser Leu Glu Gly Lys Val Val Ala Leu
                500                 505                 510

Asn Met Gly Ala Thr His Thr Lys Gln Lys Tyr Arg Ala Leu Met Val
            515                 520                 525

Ser Thr Glu Thr Gly Val Ala Ile Tyr Asn Ser Asp Glu Glu Ala Glu
        530                 535                 540

Ala Ala Gly Leu Ile Lys Thr Thr Asp Glu Asn Gly Tyr Leu Tyr Phe
545                 550                 555                 560

Leu Asn Asp Asp Leu Lys Gly Val Ala Asn Pro Gln Val Ser Gly Phe
                565                 570                 575

Leu Gln Val Trp Val Pro Val Gly Ala Pro Ala Asp Gln Asp Ile Arg
                580                 585                 590

Val Ala Ala Thr Asp Ala Ala Ser Thr Asp Gly Lys Ser Leu His Gln
            595                 600                 605

Asp Ala Ala Leu Asp Ser Arg Val Met Phe Glu Gly Phe Ser Asn Phe
        610                 615                 620

Gln Ser Phe Ala Thr Lys Glu Glu Tyr Thr Asn Val Val Ile Ala
625                 630                 635                 640

Lys Asn Val Asp Lys Phe Val Ser Trp Gly Ile Thr Asp Phe Glu Met
                645                 650                 655

Ala Pro Gln Tyr Val Ser Ser Thr Asp Gly Thr Phe Leu Asp Ser Val
            660                 665                 670

Ile Gln Asn Gly Tyr Ala Phe Thr Asp Arg Tyr Asp Leu Gly Met Ser
        675                 680                 685

Lys Ala Asn Lys Tyr Gly Thr Ala Asp Gln Leu Val Ala Ala Ile Lys
690                 695                 700

Ala Leu His Ala Lys Gly Leu Arg Val Met Ala Asp Trp Val Pro Asp
705                 710                 715                 720

Gln Met Tyr Thr Phe Pro Lys Lys Glu Val Val Thr Val Thr Arg Thr
                725                 730                 735

Asp Lys Phe Gly Asn Pro Val Ala Gly Ser Gln Ile Asn His Thr Leu
            740                 745                 750

Tyr Val Thr Asp Thr Lys Gly Ser Gly Asp Asp Tyr Gln Ala Lys Tyr
        755                 760                 765

Gly Gly Ala Phe Leu Asp Glu Leu Lys Glu Lys Tyr Pro Glu Leu Phe
770                 775                 780

Thr Lys Lys Gln Ile Ser Thr Gly Gln Ala Ile Asp Pro Ser Val Lys
785                 790                 795                 800

Ile Lys Gln Trp Ser Ala Lys Tyr Phe Asn Gly Ser Asn Ile Leu Gly
                805                 810                 815

Arg Gly Ala Asn Tyr Val Leu Ser Asp Gln Ala Ser Asn Lys Tyr Phe
            820                 825                 830

Asn Val Ala Glu Gly Lys Val Phe Leu Pro Ala Ala Met Leu Gly Lys
        835                 840                 845

Val Val Glu
    850
```

<210> SEQ ID NO 17
<211> LENGTH: 4557
<212> TYPE: DNA
<213> ORGANISM: Streptococcus salivarius

<400> SEQUENCE: 17

```
atggaaaata agatacacta taagcttcat aaagttaaga agcaatgggt tacaattgca      60
gttgcttctg tagcacttgc tactgtcttg ggaggattgt ctgtaacaac atcttcagtt     120
tcagcggatg aaactcaaga taagacagta actcaatcaa attcaggtac aacagcttct     180
ttagttactt ctcctgaagc aaccaaagaa gccgataaac gtacaaatac aaaagaagca     240
gatgttttaa cacctgctaa agaaacaaat gctgtagaaa cagcgactac aacgaacaca     300
caagcaacag ctgaagcagc tacaacagca acaacagctg atgtagcagt ggcagctgtt     360
ccaaataaag aagcagttgt gacaacagat gcaccagctg ttacaactga aaaagcagaa     420
gaacaaccag caacagtgaa ggctgaagtt gttaatacag aagttaaggc gccagaagct     480
gctttgaaag attcagaagt agaagctgcg ctttccttga aaaacatcaa aaacattgat     540
ggtaaatatt actatgttaa tgaagatggt tcacacaaag aaaactttgc cattactgta     600
aatggtcaat tgctttactt cggtaaagat ggtgctctta caagttcatc aacatactct     660
ttcacaccag gaacaacaaa tattgttgat ggtttctcaa taaataaccg tgcctacgat     720
tcatctgaag ctagctttga attgattgat ggttatttga ctgcagatag ctggtaccgt     780
ccagcttcta tcatcaaaga tggtgtaact tggcaagcat caactgcaga agatttccgt     840
ccacttttga tggcttggtg gccaaatgta gatacacaag ttaactactt gaactacatg     900
tctaaagtat ttaacttgga tgctaaatat tcaagtacag ataagcaaga aactttgaaa     960
gttgctgcta aggacattca atcaagatt gagcaaaaga ttcaggctga aaaatcaaca    1020
caatggttgc gtgaaactat ctctgccttt gttaagacac aaccacaatg gaacaaagaa    1080
actgaaaact actctaaagg tggcggcgaa gatcacttc aaggtggtgc ccttctttat    1140
gtgaatgatt cacgtacacc atgggcgaat tctgactatc gtcgtttgaa ccgtacagca    1200
actaaccaga ctggtacaat tgataaatca attcttgatg agcaatcaga tccaaaccac    1260
atgggtggtt tcgacttctt gctagctaat gacgtagatt tgtcaaaccc agttgttcaa    1320
gcggaacaat tgaaccaaat ccactacctt atgaactggg gttcaatcgt tatgggtgac    1380
aaggatgcta acttcgatgg tatccgtgtc gacgcggtag ataatgtcga tgcagacatg    1440
cttcaactct acacaaacta cttccgtgag tactatggtg ttaacaaatc tgaagcaaac    1500
gctcttgctc acatctcagt ccttgaagca tggagcctta atgacaacca ctacaatgac    1560
aagacagatg gcgctgcgct tgctatggaa aacaaacaac gtttggctct cctcttctca    1620
ttggctaaac caatcaaaga acgtacacca gctgtaagtc ctttgtataa caatactttc    1680
aacacgacac aacgtgatga aaagactgat tggattaaca aagatggaag caaggcctat    1740
aacgaagacg gaacagttaa acagtctaca atcggtaaat ataacgagaa atacggagat    1800
gcgtcaggaa attacgtctt tatccgtgcc catgataaca acgttcaaga tattattgct    1860
gaaatcatca agaaagaaat caatccaaaa tcagatggtt tcacgattac tgatgctgaa    1920
atgaagcaag cctttgagat ttacaacaaa gacatgctca gcagcgacaa aaaatatacg    1980
cttaacaaca tcccagcggc ttacgcggtt atgttcaaa acatggaaac tatcactcgt    2040
gtctactatg gagacctta tacagatgat ggtcactaca tggaaactaa gtctccatat    2100
tacgatacca ttgttaactt gatgaagagt cgtatcaagt atgtatctgg tgggcaagca    2160
```

```
caacgttcat actggttgcc aactgatggt aagatggaca attcagatgt tgaactttac    2220
cgcacaaatg aagtctacac ttcagtacgt tatggtaaag acattatgac agctaatgat    2280
acagaaggtt ctaaatacag ccgtacttct ggtcaggtaa cacttgtagc taacaatcca    2340
aaattgaatt tggatcaatc agctaaactt aatgttgaaa tgggtaaaat ccatgccaac    2400
caaaaatacc gtgctttgat tgttggtaca gctgatggta tcaagaactt tacatctgat    2460
gcagatgcaa tcgcagcagg ttacgttaaa gaaacagaca gcaacggtgt cttgactttc    2520
ggtgctaatg acatcaaggg ttatgaaaca tttgatatgt ctggtttcgt agcagtttgg    2580
gttccagttg gagcttcaga taatcaagat atccgagtag cgccttcaac agaagctaaa    2640
aaagagggtg aattgactct taaagcgact gaagcttatg attcacaatt aatctacgaa    2700
ggcttctcta actttcaaac tattccagat ggttcagatc cttcagtcta tactaaccgt    2760
aagattgctg aaaatgttga tttgttcaaa tcatggggtg taacatcatt tgaaatggca    2820
cctcaatttg tatctgctga cgatggtacc ttccttgact cagttatcca aaatggttat    2880
gcctttgcag accgttacga tcttgccatg agtaagaaca ataaatacgg ttctaaagaa    2940
gatctacgtg atgctcttaa agcacttcat aaggctggta ttcaagcaat cgctgactgg    3000
gttccagacc aaatttacca attgccaggt aaagaagttg taacagcgac tcgtactgat    3060
ggtgctggtc gtaagattgc ggacgctatc attgaccact cacttatgt ggctaactct    3120 aagtcatcag gcaaagatta ccaagctaaa tacggtggtg aattcttggc tgaacttaaa    3180
gctaagtacc ctgaaatgtt caaggtaaac atgatttcaa ctggtaaacc aattgatgat    3240
tctgttaaat tgaaacaatg gaaggctgaa tacttcaacg gaacaaacgt tcttgaacgt    3300
ggtgttggct atgtacttag cgatgaagca actggtaagt atttcactgt cactaaagaa    3360
ggtaacttca ttcctcttca attgacaggt aaagaaaagg ttattactgg attctcaagt    3420
gatggtaaag gaatcactta cttcggtaca agtggtacac aagctaaatc tgcctttgta    3480
accttcaatg gtaacactta ctactttgat gctcgtggtc acatggttac taacagtgaa    3540
tactcaccaa atggtaaaga cgtttatcgt ttcttaccaa atggtatcat gttgagtaat    3600
gccttctaca ttgatgctaa tggtaatacc tacctttata actctaaagg tcaaatgtac    3660
aagggtggtt acactaaatt tgatgttttct gaaactgata agacggtaa agaatctaag    3720 gttgtgaaat tccgttactt cactaatgaa ggtgtcatgg ccaaaggtgt tacgttatt    3780 gatggtttca cacaatattt tggagaagac ggtttccaag ctaaagataa gttagtaacc    3840
tttaaaggta aaacttatta ctttgacgca cacactggta atggtatcaa ggatacttgg    3900
agaaatatca atggtaagtg gtactacttt gatgcaaacg tgttgctgc tacaggtgca    3960 caagtcatca atggtcaaaa actttacttc aatgaagatg gaagccaagt taaaggtggc    4020
gttgttaaga atgcagatgg tacttacagc aagtacaaag aaggttttgg agagctagtg    4080
actaacgaat tcttcacaac tgatggcaat gtttggtact atgcaggcgc taatggtaag    4140
actgttacag gtgcacaagt catcaatggc caacacctat actttaatgc agacggaagc    4200
caagttaagg gtggtgttgt taagaatgca gatggtactt atagtaagta taatgcttca    4260
acaggtgaac gcttgactaa tgagttttc acaacaggcg acaacaactg gtactacatt    4320
ggtgctaatg gtaagtcagt gactggtgaa gttaaaattg gtgacgatac ttatttcttc    4380
gctaaggatg gtaaacaagt aaaaggtcaa acagtaagtg ctggcaatgg tcgaattagc    4440
tattactatg gtgatagtgg taagagagct gttagcacat ggatagaaat tcaaccagga    4500
```

```
gtttacgttt actttgataa gaatggtctt gcttatccac ctagagtgct aaactaa        4557
```

<210> SEQ ID NO 18
<211> LENGTH: 1518
<212> TYPE: PRT
<213> ORGANISM: Streptococcus salivarius

<400> SEQUENCE: 18

| Met | Glu | Asn | Lys | Ile | His | Tyr | Lys | Leu | His | Lys | Val | Lys | Lys | Gln | Trp |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

Val Thr Ile Ala Val Ala Ser Val Ala Leu Ala Thr Val Leu Gly Gly
            20                  25                  30

Leu Ser Val Thr Ser Ser Val Ser Ala Asp Glu Thr Gln Asp Lys
        35                  40                  45

Thr Val Thr Gln Ser Asn Ser Gly Thr Thr Ala Ser Leu Val Thr Ser
    50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Thr Ala Thr Thr
            100                 105                 110

Ala Asp Val Ala Val Ala Val Pro Asn Lys Glu Ala Val Val Thr
        115                 120                 125

Thr Asp Ala Pro Ala Val Thr Thr Glu Lys Ala Glu Glu Gln Pro Ala
    130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Val Asn Glu Asp Gly Ser His
            180                 185                 190

Lys Glu Asn Phe Ala Ile Thr Val Asn Gly Gln Leu Leu Tyr Phe Gly
        195                 200                 205

Lys Asp Gly Ala Leu Thr Ser Ser Thr Tyr Ser Phe Thr Pro Gly
    210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
            260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
    290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
        355                 360                 365

-continued

```
Gly Glu Asp His Leu Gln Gly Gly Ala Leu Leu Tyr Val Asn Asp Ser
    370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
            420                 425                 430

Asp Leu Ser Asn Pro Val Val Gln Ala Glu Gln Leu Asn Gln Ile His
        435                 440                 445

Tyr Leu Met Asn Trp Gly Ser Ile Val Met Gly Asp Lys Asp Ala Asn
450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
            500                 505                 510

Leu Asn Asp Asn His Tyr Asn Asp Lys Thr Asp Gly Ala Ala Leu Ala
        515                 520                 525

Met Glu Asn Lys Gln Arg Leu Ala Leu Leu Phe Ser Leu Ala Lys Pro
530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
        595                 600                 605

Arg Ala His Asp Asn Asn Val Gln Asp Ile Ile Ala Glu Ile Ile Lys
610                 615                 620

Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
            660                 665                 670

Gln Asn Met Glu Thr Ile Thr Arg Val Tyr Tyr Gly Asp Leu Tyr Thr
        675                 680                 685

Asp Asp Gly His Tyr Met Glu Thr Lys Ser Pro Tyr Tyr Asp Thr Ile
690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asn Ser Asp
                725                 730                 735

Val Glu Leu Tyr Arg Thr Asn Glu Val Tyr Thr Ser Val Arg Tyr Gly
            740                 745                 750

Lys Asp Ile Met Thr Ala Asn Asp Thr Glu Gly Ser Lys Tyr Ser Arg
        755                 760                 765

Thr Ser Gly Gln Val Thr Leu Val Ala Asn Asn Pro Lys Leu Asn Leu
770                 775                 780

Asp Gln Ser Ala Lys Leu Asn Val Glu Met Gly Lys Ile His Ala Asn
```

-continued

```
              785                 790                 795                 800
Gln Lys Tyr Arg Ala Leu Ile Val Gly Thr Ala Asp Gly Ile Lys Asn
                805                 810                 815
Phe Thr Ser Asp Ala Asp Ala Ile Ala Ala Gly Tyr Val Lys Glu Thr
                820                 825                 830
Asp Ser Asn Gly Val Leu Thr Phe Gly Ala Asn Asp Ile Lys Gly Tyr
                835                 840                 845
Glu Thr Phe Asp Met Ser Gly Phe Val Ala Val Trp Val Pro Val Gly
    850                 855                 860
Ala Ser Asp Asn Gln Asp Ile Arg Val Ala Pro Ser Thr Glu Ala Lys
865                 870                 875                 880
Lys Glu Gly Glu Leu Thr Leu Lys Ala Thr Glu Ala Tyr Asp Ser Gln
                885                 890                 895
Leu Ile Tyr Glu Gly Phe Ser Asn Phe Gln Thr Ile Pro Asp Gly Ser
                900                 905                 910
Asp Pro Ser Val Tyr Thr Asn Arg Lys Ile Ala Glu Asn Val Asp Leu
                915                 920                 925
Phe Lys Ser Trp Gly Val Thr Ser Phe Glu Met Ala Pro Gln Phe Val
    930                 935                 940
Ser Ala Asp Asp Gly Thr Phe Leu Asp Ser Val Ile Gln Asn Gly Tyr
945                 950                 955                 960
Ala Phe Ala Asp Arg Tyr Asp Leu Ala Met Ser Lys Asn Asn Lys Tyr
                965                 970                 975
Gly Ser Lys Glu Asp Leu Arg Asp Ala Leu Lys Ala Leu His Lys Ala
                980                 985                 990
Gly Ile Gln Ala Ile Ala Asp Trp Val Pro Asp Gln Ile Tyr Gln Leu
                995                 1000                1005
Pro Gly Lys Glu Val Val Thr Ala Thr Arg Thr Asp Gly Ala Gly
    1010                1015                1020
Arg Lys Ile Ala Asp Ala Ile Ile Asp His Ser Leu Tyr Val Ala
    1025                1030                1035
Asn Ser Lys Ser Ser Gly Lys Asp Tyr Gln Ala Lys Tyr Gly Gly
    1040                1045                1050
Glu Phe Leu Ala Glu Leu Lys Ala Lys Tyr Pro Glu Met Phe Lys
    1055                1060                1065
Val Asn Met Ile Ser Thr Gly Lys Pro Ile Asp Asp Ser Val Lys
    1070                1075                1080
Leu Lys Gln Trp Lys Ala Glu Tyr Phe Asn Gly Thr Asn Val Leu
    1085                1090                1095
Glu Arg Gly Val Gly Tyr Val Leu Ser Asp Glu Ala Thr Gly Lys
    1100                1105                1110
Tyr Phe Thr Val Thr Lys Glu Gly Asn Phe Ile Pro Leu Gln Leu
    1115                1120                1125
Thr Gly Lys Glu Lys Val Ile Thr Gly Phe Ser Ser Asp Gly Lys
    1130                1135                1140
Gly Ile Thr Tyr Phe Gly Thr Ser Gly Thr Gln Ala Lys Ser Ala
    1145                1150                1155
Phe Val Thr Phe Asn Gly Asn Thr Tyr Tyr Phe Asp Ala Arg Gly
    1160                1165                1170
His Met Val Thr Asn Ser Glu Tyr Ser Pro Asn Gly Lys Asp Val
    1175                1180                1185
Tyr Arg Phe Leu Pro Asn Gly Ile Met Leu Ser Asn Ala Phe Tyr
    1190                1195                1200
```

Ile Asp Ala Asn Gly Asn Thr Tyr Leu Tyr Asn Ser Lys Gly Gln
1205                1210                1215

Met Tyr Lys Gly Gly Tyr Thr Lys Phe Asp Val Ser Glu Thr Asp
1220                1225                1230

Lys Asp Gly Lys Glu Ser Lys Val Val Lys Phe Arg Tyr Phe Thr
1235                1240                1245

Asn Glu Gly Val Met Ala Lys Gly Val Thr Val Ile Asp Gly Phe
1250                1255                1260

Thr Gln Tyr Phe Gly Glu Asp Gly Phe Gln Ala Lys Asp Lys Leu
1265                1270                1275

Val Thr Phe Lys Gly Lys Thr Tyr Tyr Phe Asp Ala His Thr Gly
1280                1285                1290

Asn Gly Ile Lys Asp Thr Trp Arg Asn Ile Asn Gly Lys Trp Tyr
1295                1300                1305

Tyr Phe Asp Ala Asn Gly Val Ala Ala Thr Gly Ala Gln Val Ile
1310                1315                1320

Asn Gly Gln Lys Leu Tyr Phe Asn Glu Asp Gly Ser Gln Val Lys
1325                1330                1335

Gly Gly Val Val Lys Asn Ala Asp Gly Thr Tyr Ser Lys Tyr Lys
1340                1345                1350

Glu Gly Phe Gly Glu Leu Val Thr Asn Glu Phe Phe Thr Thr Asp
1355                1360                1365

Gly Asn Val Trp Tyr Tyr Ala Gly Ala Asn Gly Lys Thr Val Thr
1370                1375                1380

Gly Ala Gln Val Ile Asn Gly Gln His Leu Tyr Phe Asn Ala Asp
1385                1390                1395

Gly Ser Gln Val Lys Gly Gly Val Val Lys Asn Ala Asp Gly Thr
1400                1405                1410

Tyr Ser Lys Tyr Asn Ala Ser Thr Gly Glu Arg Leu Thr Asn Glu
1415                1420                1425

Phe Phe Thr Thr Gly Asp Asn Asn Trp Tyr Tyr Ile Gly Ala Asn
1430                1435                1440

Gly Lys Ser Val Thr Gly Glu Val Lys Ile Gly Asp Asp Thr Tyr
1445                1450                1455

Phe Phe Ala Lys Asp Gly Lys Gln Val Lys Gly Gln Thr Val Ser
1460                1465                1470

Ala Gly Asn Gly Arg Ile Ser Tyr Tyr Tyr Gly Asp Ser Gly Lys
1475                1480                1485

Arg Ala Val Ser Thr Trp Ile Glu Ile Gln Pro Gly Val Tyr Val
1490                1495                1500

Tyr Phe Asp Lys Asn Gly Leu Ala Tyr Pro Pro Arg Val Leu Asn
1505                1510                1515

<210> SEQ ID NO 19
<211> LENGTH: 3744
<212> TYPE: DNA
<213> ORGANISM: Streptococcus salivarius

<400> SEQUENCE: 19
atgccaagcc acattaagac catcaacggc aaacaatact acgtggagga tgacggtacg    60
attcgcaaga attacgtcct ggagcgtatc ggtggcagcc aatactttaa tgcagaaacc   120
ggtgaactgt ctaatcagaa agagtatcgt ttcgacaaaa atggtggtac tggtagcagc   180
gcggacagca cgaacaccaa cgtgactgtg aacggtgaca aaaacgcatt ttacggtacc   240

```
acggacaaag acattgagct ggtcgacggc tatttcaccg cgaacacctg gtatcgcccg    300
aaagaaatcc tgaaagacgg caaagaatgg accgccagca cggagaacga taaacgcccg    360
ctgctgaccg tctggtggcc tagcaaagca atccaggcgt cttatctgaa ctacatgaaa    420
gagcaaggcc tgggtaccaa ccaaacgtac acgagcttct ccagccaaac ccaaatggat    480
caagcagccc tggaagtgca aaagcgtatt gaagagcgca tcgcacgcga gggcaatacc    540
gactggctgc gcacgaccat caagaacttc gtgaaaaccc aaccgggttg aacagcacc     600 tctgaaaatc tggacaataa tgatcatctg caaggtggcg ccctgctgta caataacgac    660
tcccgcacga gccacgcgaa cagcgactat cgcctgctga atcgtacgcc gaccagccag    720
accggcaaac acaatccgaa ataccaccaaa gataccagca atggtggttt cgaatttctg    780
ctggcgaacg acatcgataa ctctaatccg gcggttcaag cagagcaact gaactggctg    840
cattacatta tgaacatcgg taccatcacg ggcggttctg aggatgaaaa cttcgacggc    900
gttcgtgttg acgctgtgga taatgtgaat gcggatctgc tgcaaatcgc gagcgactat    960
ttcaaagcaa aatacggtgc tgatcaaagc caagatcagg cgatcaaaca cttgagcatc   1020
ctggaagcgt ggtcccataa cgacgcctac tataacgaag ataccaaagg cgcgcagttg   1080
ccgatggatg atccgatgca cctggctctg gtctactcgc tgctgcgtcc gatcggcaat   1140
cgcagcggtg tggaaccgct gatttccaac agcctgaatg accgtagcga gtccggtaag   1200
aacagcaaac gtatggcgaa ctacgcgttc gtacgcgcgc atgatagcga ggtgcaatcg   1260
attattggcc agatcatcaa aaacgagatc aatccgcaaa gcaccggtaa tacgttcacc   1320
ctggatgaga tgaagaaagc gtttgagatt tacaacaagg atatgcgtag cgcgaataag   1380
cagtatacgc agtacaacat cccgagcgcg tatgcgttga tgctgaccca caaggatacc   1440
gttccgcgtg tgtattacgg tgatatgtat acggacgacg gtcagtacat ggcgcaaaag   1500
agcccatact atgatgcgat cgaaacgctg ctgaaaggtc gcatccgcta tgccgcaggt   1560
ggtcaggaca tgaaggtcaa ctatattggt tacggtaaca ctaacggctg ggatgctgcg   1620
ggcgtgctga ccagcgtacg ttatggcacg ggcgcaaata cgccagcga tacgggtacc    1680 gccgaaacgc gtaatcaagg tatggcagtg attgttagca accaaccggc gctgcgtctg   1740
actagcaatt tgaccattaa catgggtgcc gcacaccgta atcaggctta ccgtccgctg   1800
ctgctgacga ccaacgatgg cgtcgcgacc tatttgaacg atagcgatgc gaatggtatc   1860
gttaagtaca ccgacggtaa tggtaatctg accttctccg caaacgagat tcgtggcatc   1920
cgtaacccgc aagttgatgg ctatctggcc gtctgggttc cggtaggtgc gtcggagaat   1980
caggatgttc gtgtggcgcc gagcaaagag aagaacagct ccggtctggt ttacgagagc   2040
aatgctgccc tggatagcca agttatctac gaaggcttca gcaacttcca ggacttcgtt   2100
cagaatccga gccagtatac caacaaaaag attgcagaga atgcaaattt gttcaaatcc   2160
tggggtatta ccagctttga atttgcgccg cagtacgtga gctcggatga tggtagcttc   2220
ctggacagcg ttattcagaa cggttatgcg tttacggacc gctacgacat tggtatgagc   2280
aaagacaaca aatatggttc gctggcggat ttgaaggcag cactgaagag cttgcatgcc   2340
gttggtatta gcgcaatcgc ggattgggtt cctgatcaga tctacaatct gccaggcgac   2400
gaggtcgtca ccgcaacccg cgttaacaac tacggcgaaa ccaaagatgg tgcaatcatt   2460
gatcactctt tgtacgcggc caaaacccgt acttttggta acgactacca gggtaagtat   2520
ggtggtgcgt tcctggacga gctgaaacgt ctgtatccgc agatctttga ccgcgttcag   2580
```

-continued

```
atttctaccg gtaagcgcat gaccacggac gagaagatca cccaatggtc tgcaaagtat    2640
atgaacggta cgaacatctt ggaccgtggc tctgaatacg ttttgaagaa tggtctgaat    2700
ggttactatg gcaccaatgg tggcaaagtt cgctgccga aagttgtggg tagcaatcaa    2760
agcacgaatg gcgacaatca aaacggcgac ggtagcggca gtttgaaaa gcgtctgttc    2820 agcgtgcgtt accgttataa caatggccag tacgcgaaaa atgcctttat caaagataac    2880
gacggcaatg tttactattt cgacaatagc ggtcgtatgg ctgtcggtga aaaacgatt    2940 gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg tgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaaccct cgctattacg acgttaacag cggtgagctg    3480
taccgtaatc gtttccacga aatcgacggc agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                          3744
```

<210> SEQ ID NO 20
<211> LENGTH: 1247
<212> TYPE: PRT
<213> ORGANISM: Streptococcus salivarius

<400> SEQUENCE: 20

```
Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly
                20                  25                  30

Ser Gln Tyr Phe Asn Ala Glu Thr Gly Glu Leu Ser Asn Gln Lys Glu
            35                  40                  45

Tyr Arg Phe Asp Lys Asn Gly Thr Gly Ser Ser Ala Asp Ser Thr
        50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
                85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
        115                 120                 125

Lys Ala Ile Gln Ala Ser Tyr Leu Asn Tyr Met Lys Glu Gln Gly Leu
    130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
```

-continued

```
                165                 170                 175
Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
            195                 200                 205

His Leu Gln Gly Gly Ala Leu Leu Tyr Asn Asn Asp Ser Arg Thr Ser
        210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
                245                 250                 255

Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
        275                 280                 285

Ile Thr Gly Gly Ser Glu Asp Glu Asn Phe Asp Gly Val Arg Val Asp
    290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
                325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
        355                 360                 365

Ala Leu Val Tyr Ser Leu Leu Arg Pro Ile Gly Asn Arg Ser Gly Val
    370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
                405                 410                 415

Glu Val Gln Ser Ile Ile Gly Gln Ile Ile Lys Asn Glu Ile Asn Pro
            420                 425                 430

Gln Ser Thr Gly Asn Thr Phe Thr Leu Asp Glu Met Lys Lys Ala Phe
        435                 440                 445

Glu Ile Tyr Asn Lys Asp Met Arg Ser Ala Asn Lys Gln Tyr Thr Gln
    450                 455                 460

Tyr Asn Ile Pro Ser Ala Tyr Ala Leu Met Leu Thr His Lys Asp Thr
465                 470                 475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
            500                 505                 510

Gly Arg Ile Arg Tyr Ala Ala Gly Gly Gln Asp Met Lys Val Asn Tyr
        515                 520                 525

Ile Gly Tyr Gly Asn Thr Asn Gly Trp Asp Ala Ala Gly Val Leu Thr
    530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
            580                 585                 590
```

```
Arg Asn Gln Ala Tyr Arg Pro Leu Leu Leu Thr Thr Asn Asp Gly Val
        595                 600                 605

Ala Thr Tyr Leu Asn Asp Ser Asp Ala Asn Gly Ile Val Lys Tyr Thr
    610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
            660                 665                 670

Ser Ser Gly Leu Val Tyr Glu Ser Asn Ala Ala Leu Asp Ser Gln Val
        675                 680                 685

Ile Tyr Glu Gly Phe Ser Asn Phe Gln Asp Phe Val Gln Asn Pro Ser
    690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
            740                 745                 750

Asp Arg Tyr Asp Ile Gly Met Ser Lys Asp Asn Lys Tyr Gly Ser Leu
        755                 760                 765

Ala Asp Leu Lys Ala Ala Leu Lys Ser Leu His Ala Val Gly Ile Ser
    770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                805                 810                 815

Gly Ala Ile Ile Asp His Ser Leu Tyr Ala Ala Lys Thr Arg Thr Phe
            820                 825                 830

Gly Asn Asp Tyr Gln Gly Lys Tyr Gly Gly Ala Phe Leu Asp Glu Leu
        835                 840                 845

Lys Arg Leu Tyr Pro Gln Ile Phe Asp Arg Val Gln Ile Ser Thr Gly
    850                 855                 860

Lys Arg Met Thr Thr Asp Glu Lys Ile Thr Gln Trp Ser Ala Lys Tyr
865                 870                 875                 880

Met Asn Gly Thr Asn Ile Leu Asp Arg Gly Ser Glu Tyr Val Leu Lys
                885                 890                 895

Asn Gly Leu Asn Gly Tyr Tyr Gly Thr Asn Gly Gly Lys Val Ser Leu
            900                 905                 910

Pro Lys Val Val Gly Ser Asn Gln Ser Thr Asn Gly Asp Asn Gln Asn
        915                 920                 925

Gly Asp Gly Ser Gly Lys Phe Glu Lys Arg Leu Phe Ser Val Arg Tyr
    930                 935                 940

Arg Tyr Asn Asn Gly Gln Tyr Ala Lys Asn Ala Phe Ile Lys Asp Asn
945                 950                 955                 960

Asp Gly Asn Val Tyr Tyr Phe Asp Asn Ser Gly Arg Met Ala Val Gly
                965                 970                 975

Glu Lys Thr Ile Asp Gly Lys Gln Tyr Phe Phe Leu Ala Asn Gly Val
            980                 985                 990

Gln Leu Arg Asp Gly Tyr Arg Gln  Asn Arg Arg Gly Gln  Val Phe Tyr
        995                 1000                1005
```

Tyr Asp Gln Asn Gly Val Leu Asn Ala Asn Gly Lys Gln Asp Pro
1010                1015                1020

Lys Pro Asp Asn Asn Asn Ala Ser Gly Arg Asn Gln Phe Val
1025                1030                1035

Gln Ile Gly Asn Asn Val Trp Ala Tyr Tyr Asp Gly Asn Gly Lys
1040                1045                1050

Arg Val Thr Gly His Gln Asn Ile Asn Gly Gln Glu Leu Phe Phe
1055                1060                1065

Asp Asn Asn Gly Val Gln Val Lys Gly Arg Thr Val Asn Glu Asn
1070                1075                1080

Gly Ala Ile Arg Tyr Tyr Asp Ala Asn Ser Gly Glu Met Ala Arg
1085                1090                1095

Asn Arg Phe Ala Glu Ile Glu Pro Gly Val Trp Ala Tyr Phe Asn
1100                1105                1110

Asn Asp Gly Thr Ala Val Lys Gly Ser Gln Asn Ile Asn Gly Gln
1115                1120                1125

Asp Leu Tyr Phe Asp Gln Asn Gly Arg Gln Val Lys Gly Ala Leu
1130                1135                1140

Ala Asn Val Asp Gly Asn Leu Arg Tyr Tyr Asp Val Asn Ser Gly
1145                1150                1155

Glu Leu Tyr Arg Asn Arg Phe His Glu Ile Asp Gly Ser Trp Tyr
1160                1165                1170

Tyr Phe Asp Gly Asn Gly Asn Ala Val Lys Gly Met Val Asn Ile
1175                1180                1185

Asn Gly Gln Asn Leu Leu Phe Asp Asn Asn Gly Lys Gln Ile Lys
1190                1195                1200

Gly His Leu Val Arg Val Asn Gly Val Val Arg Tyr Phe Asp Pro
1205                1210                1215

Asn Ser Gly Glu Met Ala Val Asn Arg Trp Val Glu Val Ser Pro
1220                1225                1230

Gly Trp Trp Val Tyr Phe Asp Gly Glu Gly Arg Gly Gln Ile
1235                1240                1245

<210> SEQ ID NO 21
<211> LENGTH: 4311
<212> TYPE: DNA
<213> ORGANISM: Streptococcus downei

<400> SEQUENCE: 21

```
atggttgacg gcaaatacta ctactacgat caggacggca acgtaaagaa aaacttcgcg     60
gttagcgtgg gcgagaaaat ctattacttt gacgaaactg gcgcctacaa agacaccagc    120
aaagttgagg cggacaaaag cggcagcgac attagcaagg aagagactac cttcgcggca    180
aacaaccgcg cctacagcac cagcgcggag aattttgagg cgatcgacaa ttatctgacc    240
gcggactcct ggtatcgtcc taaatccatc ctgaaggatg caaaacgtg acgaaagc      300
agcaaagatg actttcgtcc gctgctgatg cgtggtggc cggataccga aacgaagcgc    360
aattacgtga actacatgaa caaagttgtt ggcatcgaca agacctatac cgcggaaacc    420
agccaggccg acttgaccgc tgcggcggaa ctggtgcaag cacgcattga gcagaagatc    480
acgaccgaac agaacacgaa atggctgcgt gaggcaatct cggcatttgt aaaacgcaa     540
ccgcagtgga acggtgaaag cgagaagccg tacgacgatc acctgcaaaa cggtgctctg    600
aaatttgata tcagagcga cctgaccccg gatacgcaaa gcaactaccg tctgttgaac    660
cgtaccccga ctaatcagac gggtagcctg gacagccgct tcacttataa cgcgaacgac    720
```

```
cctttgggcg gttatgagct gctgctggca aatgacgtcg ataacagcaa tccgatcgtg    780
caggcggagc agctgaactg gctgcattac ctgctgaatt ttggtacgat ctacgccaaa    840
gatgccgacg ctaacttcga tagcattcgt gtggacgcgg ttgataacgt cgatgcggat    900
ctgctgcaaa ttagcagcga ttacctgaaa gcagcctacg gcattgataa gaataacaaa    960
aacgcgaaca accacgtgag cattgtcgaa gcctggagcg ataatgatac cccgtacctg   1020
catgacgatg tgacaaccct gatgaatatg gataacaaat ttcgcctgtc catgctgtgg   1080
tcgctggcca aaccgctgga caagcgtagc ggtctgaacc cgctgattca taacagcttg   1140
gtggatcgtg aagttgatga ccgcgaggtt gaaacggttc cgagctattc ttttgcacgt   1200
gcgcatgata gcgaggtcca ggacttgatc cgtgacatca tcaaggcaga gatcaatccg   1260
aacgcattcg gttatagctt tacccaagac gagattgacc aggcctttaa gatttacaat   1320
gaggatctga agaaaacgga taagaaatac acccactata atgtgccgtt gagctacacc   1380
ctgctgctga cgaataaggg tagcatccca cgtgtctact atggtgatat gtttaccgac   1440
gatggtcagt atatggcgaa caaaaccgtc aactatgacg ccattgaatc tctgctgaaa   1500
gcgcgtatga agtatgtcgc tggcggtcaa gcaatgcaga actaccaaat cggtaatggt   1560
gagatcctga ccagcgttcg ttatggtaag ggtgccctga acagagcga caaaggtgat   1620
gcgaccacgc gcaccagcgg tgtcggtgtc gttatgggca atcagccaaa ctttagcttg   1680
gacggcaaag tggtggctct gaacatgggc gcagctcatg cgaatcagga gtatcgtgcg   1740
ctgatggtta gcacgaaaga cggtgttgcc acgtatgcga ccgatgcaga tgcgagcaaa   1800
gccggtctgg tcaaacgtac cgacgaaaac ggctacctgt atttcctgaa tgacgacctg   1860
aagggtgtgg ccaatcctca ggtgagcggt tcttgcagg tgtgggttcc ggtgggtgcc   1920
gcggatgatc aagatatccg tgttgcagct agcgataccg catccaccga tggcaagagc   1980
ctgcaccaag acgccgcgat ggatagccgt gttatgtttg aaggcttctc taactttcag   2040
tcctttgcca cgaaagaaga ggaatatacc aacgtcgtta tcgccaacaa tgtggataag   2100
ttcgttagct ggggtatcac ggatttcgag atggccccac aatatgtttc cagcaccgac   2160
ggtcaattcc tggactctgt cattcagaac ggttatgctt ttacgaccg ttatgacttg   2220
ggcatgtcta aggcaaacaa atacggcacg gccgatcaac tggttaaggc cattaaggcc   2280
ctgcacgcga agggcctgaa ggttatggca gattgggtgc cggatcagat gtataccttc   2340
ccgaaacagg aagtcgtgac cgttacccgt accgacaaat ttggcaaacc gatcgcaggt   2400
tcccaaatca atcatagcct gtatgttacc gataccaagt ccagcggcga tgactatcag   2460
gccaaatatg gtggtgcgtt tctggacgag ctgaaggaga aatatccgga gctgttcacg   2520
aagaaacaaa tcagcacggg tcaagctatt gacccgagcg tgaaaatcaa acagtggtct   2580
gctaagtatt tcaatggctc caacatcctg ggtcgcggtg cggactacgt actgtcggat   2640
caggcgagca caaataccct gaacgtgtct gacgataaac tgttcctgcc gaaaaccttg   2700
ctgggccaag ttgtcgagag cggtatccgc tttgacggca ctggttatgt gtacaactct   2760
agcactacgg gtgaaaaagt taccgattcc ttcattacgg aggcaggtaa tctgtactac   2820
ttcggtcaag acggctatat ggtgaccggc gcacagaaca ttaagggcag caactattac   2880
ttcctggcca atggtgcggc cctgcgtaac accgtttaca ccgatgcgca aggtcagaat   2940
cactattacg gcaacgacgg caagcgttat gagaatggtt accaacagtt cggcaacgat   3000
tcttggcgtt acttcaaaaa tggcgtgatg gcgctgggtc tgactacggt ggatggtcac   3060
```

-continued

```
gtgcagtatt tcgataaaga tggtgtccag gccaaggata agatcattgt cacccgcgat   3120
ggcaaagtcc gctatttcga ccagcacaac ggtaatgcgg ttactaacac gttcgttgcg   3180
gacaagacgg gtcactggta ctatctgggc aaagacggcg tcgcggttac cggtgcgcag   3240
actgtgggta acagcatttt gtactttgaa gcgaacggtc aacaagtcaa gggtgacttc   3300
gtgacggcta agacggtaa actgtacttc tatgatgtgg acagcggcga catgtggacc   3360
aataccttta tcgaggataa agcgggtaat tggttctacc tgggtaagga cggtgcggcc   3420
gtcaccggtg cacagacgat caaaggccag aaattgtatt tcaaagccaa cggtcagcaa   3480
gttaaaggtg acattgtcaa ggacgcggac ggtaagatcc gttattacga cgctcagacc   3540
ggtgaacagg tctttaacaa gtccgttagc gtcaacggta agacctacta tttcggtagc   3600
gacggcaccg cgcaaaccca ggcgaatccg aaaggccaaa cctttaagga tggtagcggc   3660
gttctgcgtt tctacaattt ggagggccag tatgtctcgg gcagcggctg gtacgaaacg   3720
gccgagcacg agtgggtata tgtgaaatcc ggtaaagttc tgaccggtgc ccagacgatt   3780
ggtaatcaac gtgtttactt caaggacaat ggtcaccagt gaaaggcca gctggtcacg   3840 ggtaatgacg gtaaattgcg ttactacgac gcgaacagcg gtgatcaagc attcaacaaa   3900
tccgtcacgg ttaacggtaa aacctactac tttggcagca tggtacggc gcagacgcag   3960 gctaatccta agggtcagac cttcaaagat ggtagcggcg tgctgcgttt ttacaacttg   4020
gaaggccaat acgtgtctgg cagcggttgg tacaagaatg cgcagggcca gtggctgtac   4080
gtgaaagatg caaggtcct gaccggtctg caaacggtcg gcaatcagaa ggtctacttc   4140
gacaaaaatg gcatccaagc aaagggtaag gccgttcgca cgtccgatgg taaagtgcgc   4200
tactttgatg agaatagcgg tagcatgatt acgaaccaat ggaagttcgt ttacggtcaa   4260
tactattact tcggttctga cggcgcagcg gtttaccgtg gttggaacta a           4311
```

<210> SEQ ID NO 22
<211> LENGTH: 1436
<212> TYPE: PRT
<213> ORGANISM: Streptococcus downei

<400> SEQUENCE: 22

```
Met Val Asp Gly Lys Tyr Tyr Tyr Asp Gln Asp Gly Asn Val Lys
 1               5                  10                  15

Lys Asn Phe Ala Val Ser Val Gly Glu Lys Ile Tyr Tyr Phe Asp Glu
                20                  25                  30

Thr Gly Ala Tyr Lys Asp Thr Ser Lys Val Glu Ala Asp Lys Ser Gly
            35                  40                  45

Ser Asp Ile Ser Lys Glu Glu Thr Thr Phe Ala Ala Asn Asn Arg Ala
        50                  55                  60

Tyr Ser Thr Ser Ala Glu Asn Phe Glu Ala Ile Asp Asn Tyr Leu Thr
    65                  70                  75                  80

Ala Asp Ser Trp Tyr Arg Pro Lys Ser Ile Leu Lys Asp Gly Lys Thr
                85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160
```

```
Thr Thr Glu Gln Asn Thr Lys Trp Leu Arg Glu Ala Ile Ser Ala Phe
            165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
            195                 200                 205

Thr Pro Asp Thr Gln Ser Asn Tyr Arg Leu Leu Asn Arg Thr Pro Thr
            210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Leu Ala Asn Asp Val Asp Asn Ser
            245                 250                 255

Asn Pro Ile Val Gln Ala Glu Gln Leu Asn Trp Leu His Tyr Leu Leu
            260                 265                 270

Asn Phe Gly Thr Ile Tyr Ala Lys Asp Ala Asp Ala Asn Phe Asp Ser
            275                 280                 285

Ile Arg Val Asp Ala Val Asp Asn Val Asp Ala Asp Leu Leu Gln Ile
            290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ala Phe Gly Tyr Ser Phe Thr Gln Asp Glu Ile
            420                 425                 430

Asp Gln Ala Phe Lys Ile Tyr Asn Glu Asp Leu Lys Lys Thr Asp Lys
            435                 440                 445

Lys Tyr Thr His Tyr Asn Val Pro Leu Ser Tyr Thr Leu Leu Leu Thr
450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
            485                 490                 495

Ser Leu Leu Lys Ala Arg Met Lys Tyr Val Ala Gly Gln Ala Met
            500                 505                 510

Gln Asn Tyr Gln Ile Gly Asn Gly Glu Ile Leu Thr Ser Val Arg Tyr
            515                 520                 525

Gly Lys Gly Ala Leu Lys Gln Ser Asp Lys Gly Asp Ala Thr Thr Arg
530                 535                 540

Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575
```

```
Glu Tyr Arg Ala Leu Met Val Ser Thr Lys Asp Gly Val Ala Thr Tyr
                580                 585                 590
Ala Thr Asp Ala Asp Ala Ser Lys Ala Gly Leu Val Lys Arg Thr Asp
            595                 600                 605
Glu Asn Gly Tyr Leu Tyr Phe Leu Asn Asp Asp Leu Lys Gly Val Ala
        610                 615                 620
Asn Pro Gln Val Ser Gly Phe Leu Gln Val Trp Val Pro Val Gly Ala
625                 630                 635                 640
Ala Asp Asp Gln Asp Ile Arg Val Ala Ala Ser Asp Thr Ala Ser Thr
                645                 650                 655
Asp Gly Lys Ser Leu His Gln Asp Ala Ala Met Asp Ser Arg Val Met
            660                 665                 670
Phe Glu Gly Phe Ser Asn Phe Gln Ser Phe Ala Thr Lys Glu Glu Glu
        675                 680                 685
Tyr Thr Asn Val Val Ile Ala Asn Asn Val Asp Lys Phe Val Ser Trp
    690                 695                 700
Gly Ile Thr Asp Phe Glu Met Ala Pro Gln Tyr Val Ser Ser Thr Asp
705                 710                 715                 720
Gly Gln Phe Leu Asp Ser Val Ile Gln Asn Gly Tyr Ala Phe Thr Asp
                725                 730                 735
Arg Tyr Asp Leu Gly Met Ser Lys Ala Asn Lys Tyr Gly Thr Ala Asp
            740                 745                 750
Gln Leu Val Lys Ala Ile Lys Ala Leu His Ala Lys Gly Leu Lys Val
        755                 760                 765
Met Ala Asp Trp Val Pro Asp Gln Met Tyr Thr Phe Pro Lys Gln Glu
    770                 775                 780
Val Val Thr Val Thr Arg Thr Asp Lys Phe Gly Lys Pro Ile Ala Gly
785                 790                 795                 800
Ser Gln Ile Asn His Ser Leu Tyr Val Thr Asp Thr Lys Ser Ser Gly
                805                 810                 815
Asp Asp Tyr Gln Ala Lys Tyr Gly Gly Ala Phe Leu Asp Glu Leu Lys
            820                 825                 830
Glu Lys Tyr Pro Glu Leu Phe Thr Lys Lys Gln Ile Ser Thr Gly Gln
        835                 840                 845
Ala Ile Asp Pro Ser Val Lys Ile Lys Gln Trp Ser Ala Lys Tyr Phe
    850                 855                 860
Asn Gly Ser Asn Ile Leu Gly Arg Gly Ala Asp Tyr Val Leu Ser Asp
865                 870                 875                 880
Gln Ala Ser Asn Lys Tyr Leu Asn Val Ser Asp Asp Lys Leu Phe Leu
                885                 890                 895
Pro Lys Thr Leu Leu Gly Gln Val Val Glu Ser Gly Ile Arg Phe Asp
            900                 905                 910
Gly Thr Gly Tyr Val Tyr Asn Ser Ser Thr Thr Gly Glu Lys Val Thr
        915                 920                 925
Asp Ser Phe Ile Thr Glu Ala Gly Asn Leu Tyr Phe Gly Gln Asp
    930                 935                 940
Gly Tyr Met Val Thr Gly Ala Gln Asn Ile Lys Gly Ser Asn Tyr Tyr
945                 950                 955                 960
Phe Leu Ala Asn Gly Ala Ala Leu Arg Asn Thr Val Tyr Thr Asp Ala
                965                 970                 975
Gln Gly Gln Asn His Tyr Tyr Gly Asn Asp Gly Lys Arg Tyr Glu Asn
            980                 985                 990
Gly Tyr Gln Gln Phe Gly Asn Asp  Ser Trp Arg Tyr Phe Lys Asn Gly
```

```
          995               1000                1005
Val Met Ala Leu Gly Leu Thr Thr Val Asp Gly His Val Gln Tyr
    1010                1015                1020

Phe Asp Lys Asp Gly Val Gln Ala Lys Asp Lys Ile Ile Val Thr
    1025                1030                1035

Arg Asp Gly Lys Val Arg Tyr Phe Asp Gln His Asn Gly Asn Ala
    1040                1045                1050

Val Thr Asn Thr Phe Val Ala Asp Lys Thr Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Tyr Asp Val
    1100                1105                1110

Asp Ser Gly Asp Met Trp Thr Asn Thr Phe Ile Glu Asp Lys Ala
    1115                1120                1125

Gly Asn Trp Phe Tyr Leu Gly Lys Asp Gly Ala Ala Val Thr Gly
    1130                1135                1140

Ala Gln Thr Ile Lys Gly Gln Lys Leu Tyr Phe Lys Ala Asn Gly
    1145                1150                1155

Gln Gln Val Lys Gly Asp Ile Val Lys Asp Ala Asp Gly Lys Ile
    1160                1165                1170

Arg Tyr Tyr Asp Ala Gln Thr Gly Glu Gln Val Phe Asn Lys Ser
    1175                1180                1185

Val Ser Val Asn Gly Lys Thr Tyr Tyr Phe Gly Ser Asp Gly Thr
    1190                1195                1200

Ala Gln Thr Gln Ala Asn Pro Lys Gly Gln Thr Phe Lys Asp Gly
    1205                1210                1215

Ser Gly Val Leu Arg Phe Tyr Asn Leu Glu Gly Gln Tyr Val Ser
    1220                1225                1230

Gly Ser Gly Trp Tyr Glu Thr Ala Glu His Glu Trp Val Tyr Val
    1235                1240                1245

Lys Ser Gly Lys Val Leu Thr Gly Ala Gln Thr Ile Gly Asn Gln
    1250                1255                1260

Arg Val Tyr Phe Lys Asp Asn Gly His Gln Val Lys Gly Gln Leu
    1265                1270                1275

Val Thr Gly Asn Asp Gly Lys Leu Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Ser Asp Gly Thr Ala Gln Thr Gln Ala Asn Pro
    1310                1315                1320

Lys Gly Gln Thr Phe Lys Asp Gly Ser Gly Val Leu Arg Phe Tyr
    1325                1330                1335

Asn Leu Glu Gly Gln Tyr Val Ser Gly Ser Gly Trp Tyr Lys Asn
    1340                1345                1350

Ala Gln Gly Gln Trp Leu Tyr Val Lys Asp Gly Lys Val Leu Thr
    1355                1360                1365

Gly Leu Gln Thr Val Gly Asn Gln Lys Val Tyr Phe Asp Lys Asn
    1370                1375                1380

Gly Ile Gln Ala Lys Gly Lys Ala Val Arg Thr Ser Asp Gly Lys
    1385                1390                1395
```

```
Val Arg Tyr Phe Asp Glu Asn Ser Gly Ser Met Ile Thr Asn Gln
    1400            1405                1410

Trp Lys Phe Val Tyr Gly Gln Tyr Tyr Tyr Phe Gly Ser Asp Gly
    1415            1420                1425

Ala Ala Val Tyr Arg Gly Trp Asn
    1430            1435

<210> SEQ ID NO 23
<211> LENGTH: 3942
<212> TYPE: DNA
<213> ORGANISM: Streptococcus mutans

<400> SEQUENCE: 23
atgattgacg gcaaatacta ctactatgac aacaacggca aagtacgcac caatttcacg      60
ttgatcgcgg acggtaaaat cctgcatttt gatgaaactg gcgcgtacac cgacactagc     120
attgataccg tgaacaagga tattgtcacg acgcgtagca acctgtataa gaaatacaat     180
caagtgtatg atcgcagcgc gcagagcttc gagcatgttg atcactacct gacggcggaa     240
tcttggtacc gtccgaaata cattctgaaa gatggcaaga cctggaccca gagcaccgag     300
aaggacttcc gtcctctgct gatgacctgg tggccgagcc aggaaacgca cgccagtat      360
gtcaacttca tgaacgccca gttgggtatc aacaaaacgt acgacgacac cagcaatcag     420
ctgcaattga acatcgctgc tgcaacgatc aagcaaaga tcgaagccaa atcacgacg       480
ctgaagaaca ccgattggct gcgtcaaacg atcagcgcgt tcgtcaaaac ccaaagcgct     540
tggaatagcg acagcgaaaa gccgtttgat gaccatctgc aaaacggtgc ggttctgtat     600
gataacgaag gtaaattgac gccgtatgcc aatagcaact atcgtattct gaaccgcacg     660
ccgaccaacc agaccggtaa gaaggacccg cgttataccg ccgacaacac gatcggcggc     720
tacgagtttc tgctggccaa cgacgtggat aatagcaacc cggtggttca ggccgagcag     780
ctgaactggc tgcacttcct gatgaacttt ggtaatatct acgcaaacga ccctgacgct     840
aacttcgact ccatccgcgt tgacgctgtc gataatgtgg acgccgatct gttacagatc     900
gcgggtgact atctgaaagc ggcaaagggc atccataaga tgacaaagc ggcgaacgac      960
cacctgtcca ttctggaagc gtggagcgac aatgacactc cgtatctgca tgatgatggc    1020
gacaacatga ttaacatgga taacaaactg cgcctgagcc tgctgttctc cctggcgaaa    1080
ccgctgaatc agcgtagcgg tatgaacccg ttgattacga acagcctggt caaccgtact    1140
gatgataatg ccgaaacggc ggcagtgcca agctactctt ttatccgtgc ccacgatagc    1200
gaggtccagg atttgattcg tgatatcatt aaggctgaga ttaacccgaa cgtcgtcggt    1260
tacagcttca cgatggaaga gattaagaag gcatttgaga tctacaataa ggacctgttg    1320
gccacggaga agaagtatac ccactataac accgcattga gctacgcgtt gctgctgacg    1380
aacaagagca gcgtgccgcg tgtctactat ggtgatatgt ttacggacga tggtcaatac    1440
atggcccaca gaccattaa ctacgaggca atcgaaaccc tgctgaaagc acgtatcaag     1500
tacgtgtccg gtggtcaggc tatgcgcaac cagcaagtgg gtaattcgga gatcatcacc    1560
agcgtgcgtt acggtaaagg tgcgctgaag gcgatggata cgggtgaccg cactacccgt    1620
acctctggtg tggcggtcat tgagggcaac aacccgagct tgcgcctgaa ggcttctgat    1680
cgtgtggttg tgaatatggg tgcggcccac aaaaatcaag cctatcgccc gctgctgttg    1740
acgaccgata cggcattaa ggcctatcac agcgaccaag aagcggcagg cctggtgcgt     1800
tacaccaacg accgtggcga actgatcttt accgcagccg acattaaggg ctacgcaaat    1860
```

```
ccgcaagtta gcggctacct gggcgtctgg gtccctgttg gcgcagcagc tgatcaggac    1920
gttcgtgttg cggcgagcac cgcgccaagc acggacggca agagcgttca ccagaacgcg    1980
gctctggaca gccgtgtgat gttcgagggt ttctcgaact tccaggcatt tgctaccaag    2040
aaagaagagt ataccaatgt ggtcatcgct aagaatgtgg ataagttcgc ggagtggggt    2100
gtcaccgatt tcgagatggc tccgcaatac gtttctagca ccgacggtag cttttttggat   2160 agcgtgattc aaaacggtta tgcttttacc gaccgttacg acctgggcat cagcaagccg    2220
aacaaatatg gcaccgcgga cgatctggtt aaagcgatta aggcattgca cagcaaaggc    2280
atcaaagtta tggcggattg ggttccggac cagatgtatg ccctgccgga aaaagaggtt    2340
gtgacggcaa cccgtgttga caaatacggt acgccggtag ctggcagcca gatcaaaaac    2400
acgctgtacg tggtcgatgg taaatctagc ggtaaggacc agcaggcgaa gtacggtggt    2460
gccttcctgg aagagctgca agcgaagtat ccggaactgt tcgcgcgcaa acagattagc    2520
accggtgttc cgatggaccc gagcgtcaag attaagcaat ggagcgcaaa atacttcaac    2580
ggcacgaata tcctgggtcg tggtgctggt tacgtgctga agatcaggc aaccaacacc     2640 tactttaaca tcagcgacaa taaagagatc aatttcctgc caaagacgtt gctgaaccag    2700
gattctcaag ttggctttag ctacgacggt aagggctatg tgtactacag cacctcgggc    2760
taccaggcta aaaacacgtt catcagcgag ggtgacaagt ggtattactt cgacaataac    2820
ggttatatgg ttaccggcgc acagagcatt aatggtgtga actattactt cctgccgaat    2880
ggtttacagc tgcgtgatgc gattctgaaa aatgaggacg gtacgtacgc gtattatggc    2940
aatgatggtc gccgctacga gaatggctat tatcagtttta tgagcggtgt ttggcgccat    3000
ttcaataatg gcgagatgtc cgttggtctg accgtcattg acggtcaagt tcaatacttt    3060
gacgagatgg gttaccaggc gaaaggcaaa ttcgttacca ccgcggatgg taagatccgt    3120
tacttcgata gcagagcgg caatatgtat cgtaatcgtt tcattgagaa cgaagagggc     3180
aaatggctgt acctgggtga ggacggcgcg gcagtcaccg gtagccagac gatcaatggt    3240
cagcacctgt atttgcgtgc taacggcgtt caggttaagg gtgagttcgt gaccgatcgt    3300
catggccgca tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acggccagca cctgtatttc cgcgcgaacg tgttcaggt aaaaggtgag     3480 tttgttacgg accgccacgg ccgcattagc tattatgatg gtaatagcgg tgaccaaatt    3540
cgcaatcgtt tcgtgcgtaa tgcacagggt cagtggttct acttcgacaa taatggttat    3600
gcagtcacgg gtgcacgtac cattaacggc caacacctgt actttcgcgc caatggtgtg    3660
caagtgaaag gcgaatttgt tactgatcgt tatggtcgta tcagctacta tgatggcaat    3720
tctggcgacc aaattcgcaa tcgctttgtt cgtaacgccc aaggtcaatg gttctatttc    3780
gacaacaacg gttacgcggt gaccggtgcc cgcacgatta tggtcaaca cttgtacttc     3840 cgtgccaacg tgtccaggt gaagggtgaa tttgtgaccg accgctatgg tcgcatttct     3900
tactacgacg caaattccgg tgaacgcgtc cgtatcaatt aa                       3942
```

<210> SEQ ID NO 24
<211> LENGTH: 1313
<212> TYPE: PRT
<213> ORGANISM: Streptococcus mutans

<400> SEQUENCE: 24

Met Ile Asp Gly Lys Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
            35                  40                  45

Val Thr Thr Arg Ser Asn Leu Tyr Lys Lys Tyr Asn Gln Val Tyr Asp
50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
                85                  90                  95

Gln Ser Thr Glu Lys Asp Phe Arg Pro Leu Leu Met Thr Trp Trp Pro
            100                 105                 110

Ser Gln Glu Thr Gln Arg Gln Tyr Val Asn Phe Met Asn Ala Gln Leu
            115                 120                 125

Gly Ile Asn Lys Thr Tyr Asp Asp Thr Ser Asn Gln Leu Gln Leu Asn
    130                 135                 140

Ile Ala Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
                165                 170                 175

Thr Gln Ser Ala Trp Asn Ser Asp Ser Glu Lys Pro Phe Asp Asp His
            180                 185                 190

Leu Gln Asn Gly Ala Val Leu Tyr Asp Asn Glu Gly Lys Leu Thr Pro
    195                 200                 205

Tyr Ala Asn Ser Asn Tyr Arg Ile Leu Asn Arg Thr Pro Thr Asn Gln
210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
                245                 250                 255

Gln Ala Glu Gln Leu Asn Trp Leu His Phe Leu Met Asn Phe Gly Asn
            260                 265                 270

Ile Tyr Ala Asn Asp Pro Asp Ala Asn Phe Asp Ser Ile Arg Val Asp
    275                 280                 285

Ala Val Asp Asn Val Asp Ala Asp Leu Leu Gln Ile Ala Gly Asp Tyr
290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
                325                 330                 335

His Asp Asp Gly Asp Asn Met Ile Asn Met Asp Asn Lys Leu Arg Leu
            340                 345                 350

Ser Leu Leu Phe Ser Leu Ala Lys Pro Leu Asn Gln Arg Ser Gly Met
    355                 360                 365

Asn Pro Leu Ile Thr Asn Ser Leu Val Asn Arg Thr Asp Asp Asn Ala
    370                 375                 380

Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
                405                 410                 415

Asn Val Val Gly Tyr Ser Phe Thr Met Glu Glu Ile Lys Lys Ala Phe

-continued

```
            420                 425                 430
Glu Ile Tyr Asn Lys Asp Leu Leu Ala Thr Glu Lys Lys Tyr Thr His
            435                 440                 445
Tyr Asn Thr Ala Leu Ser Tyr Ala Leu Leu Thr Asn Lys Ser Ser
            450                 455                 460
Val Pro Arg Val Tyr Tyr Gly Asp Met Phe Thr Asp Asp Gly Gln Tyr
465                 470                 475                 480
Met Ala His Lys Thr Ile Asn Tyr Glu Ala Ile Glu Thr Leu Leu Lys
                    485                 490                 495
Ala Arg Ile Lys Tyr Val Ser Gly Gly Gln Ala Met Arg Asn Gln Gln
                500                 505                 510
Val Gly Asn Ser Glu Ile Ile Thr Ser Val Arg Tyr Gly Lys Gly Ala
            515                 520                 525
Leu Lys Ala Met Asp Thr Gly Asp Arg Thr Thr Arg Thr Ser Gly Val
            530                 535                 540
Ala Val Ile Glu Gly Asn Asn Pro Ser Leu Arg Leu Lys Ala Ser Asp
545                 550                 555                 560
Arg Val Val Asn Met Gly Ala Ala His Lys Asn Gln Ala Tyr Arg
                565                 570                 575
Pro Leu Leu Leu Thr Thr Asp Asn Gly Ile Lys Ala Tyr His Ser Asp
                580                 585                 590
Gln Glu Ala Ala Gly Leu Val Arg Tyr Thr Asn Asp Arg Gly Glu Leu
            595                 600                 605
Ile Phe Thr Ala Ala Asp Ile Lys Gly Tyr Ala Asn Pro Gln Val Ser
            610                 615                 620
Gly Tyr Leu Gly Val Trp Val Pro Val Gly Ala Ala Asp Gln Asp
625                 630                 635                 640
Val Arg Val Ala Ala Ser Thr Ala Pro Ser Thr Asp Gly Lys Ser Val
                645                 650                 655
His Gln Asn Ala Ala Leu Asp Ser Arg Val Met Phe Glu Gly Phe Ser
                660                 665                 670
Asn Phe Gln Ala Phe Ala Thr Lys Lys Glu Glu Tyr Thr Asn Val Val
            675                 680                 685
Ile Ala Lys Asn Val Asp Lys Phe Ala Glu Trp Gly Val Thr Asp Phe
            690                 695                 700
Glu Met Ala Pro Gln Tyr Val Ser Ser Thr Asp Gly Ser Phe Leu Asp
705                 710                 715                 720
Ser Val Ile Gln Asn Gly Tyr Ala Phe Thr Asp Arg Tyr Asp Leu Gly
                725                 730                 735
Ile Ser Lys Pro Asn Lys Tyr Gly Thr Ala Asp Asp Leu Val Lys Ala
                740                 745                 750
Ile Lys Ala Leu His Ser Lys Gly Ile Lys Val Met Ala Asp Trp Val
            755                 760                 765
Pro Asp Gln Met Tyr Ala Leu Pro Glu Lys Glu Val Val Thr Ala Thr
            770                 775                 780
Arg Val Asp Lys Tyr Gly Thr Pro Val Ala Gly Ser Gln Ile Lys Asn
785                 790                 795                 800
Thr Leu Tyr Val Val Asp Gly Lys Ser Ser Gly Lys Asp Gln Gln Ala
                805                 810                 815
Lys Tyr Gly Gly Ala Phe Leu Glu Glu Leu Gln Ala Lys Tyr Pro Glu
                820                 825                 830
Leu Phe Ala Arg Lys Gln Ile Ser Thr Gly Val Pro Met Asp Pro Ser
            835                 840                 845
```

-continued

```
Val Lys Ile Lys Gln Trp Ser Ala Lys Tyr Phe Asn Gly Thr Asn Ile
    850                 855                 860
Leu Gly Arg Gly Ala Gly Tyr Val Leu Lys Asp Gln Ala Thr Asn Thr
    865                 870                 875                 880
Tyr Phe Asn Ile Ser Asp Asn Lys Glu Ile Asn Phe Leu Pro Lys Thr
                    885                 890                 895
Leu Leu Asn Gln Asp Ser Gln Val Gly Phe Ser Tyr Asp Gly Lys Gly
                900                 905                 910
Tyr Val Tyr Tyr Ser Thr Ser Gly Tyr Gln Ala Lys Asn Thr Phe Ile
            915                 920                 925
Ser Glu Gly Asp Lys Trp Tyr Tyr Phe Asp Asn Asn Gly Tyr Met Val
    930                 935                 940
Thr Gly Ala Gln Ser Ile Asn Gly Val Asn Tyr Tyr Phe Leu Pro Asn
945                 950                 955                 960
Gly Leu Gln Leu Arg Asp Ala Ile Leu Lys Asn Glu Asp Gly Thr Tyr
                965                 970                 975
Ala Tyr Tyr Gly Asn Asp Gly Arg Arg Tyr Glu Asn Gly Tyr Tyr Gln
                980                 985                 990
Phe Met Ser Gly Val Trp Arg His Phe Asn Asn Gly Glu Met Ser Val
                995                 1000                1005
Gly Leu Thr Val Ile Asp Gly Gln Val Gln Tyr Phe Asp Glu Met
    1010                1015                1020
Gly Tyr Gln Ala Lys Gly Lys Phe Val Thr Thr Ala Asp Gly Lys
    1025                1030                1035
Ile Arg Tyr Phe Asp Lys Gln Ser Gly Asn Met Tyr Arg Asn Arg
    1040                1045                1050
Phe Ile Glu Asn Glu Glu Gly Lys Trp Leu Tyr Leu Gly Glu Asp
    1055                1060                1065
Gly Ala Ala Val Thr Gly Ser Gln Thr Ile Asn Gly Gln His Leu
    1070                1075                1080
Tyr Phe Arg Ala Asn Gly Val Gln Val Lys Gly Glu Phe Val Thr
    1085                1090                1095
Asp Arg His Gly Arg Ile Ser Tyr Tyr Asp Gly Asn Ser Gly Asp
    1100                1105                1110
Gln Ile Arg Asn Arg Phe Val Arg Asn Ala Gln Gly Gln Trp Phe
    1115                1120                1125
Tyr Phe Asp Asn Asn Gly Tyr Ala Val Thr Gly Ala Arg Thr Ile
    1130                1135                1140
Asn Gly Gln His Leu Tyr Phe Arg Ala Asn Gly Val Gln Val Lys
    1145                1150                1155
Gly Glu Phe Val Thr Asp Arg His Gly Arg Ile Ser Tyr Tyr Asp
    1160                1165                1170
Gly Asn Ser Gly Asp Gln Ile Arg Asn Arg Phe Val Arg Asn Ala
    1175                1180                1185
Gln Gly Gln Trp Phe Tyr Phe Asp Asn Asn Gly Tyr Ala Val Thr
    1190                1195                1200
Gly Ala Arg Thr Ile Asn Gly Gln His Leu Tyr Phe Arg Ala Asn
    1205                1210                1215
Gly Val Gln Val Lys Gly Glu Phe Val Thr Asp Arg Tyr Gly Arg
    1220                1225                1230
Ile Ser Tyr Tyr Asp Gly Asn Ser Gly Asp Gln Ile Arg Asn Arg
    1235                1240                1245
```

Phe Val Arg Asn Ala Gln Gly Gln Trp Phe Tyr Phe Asp Asn Asn
    1250                1255                1260

Gly Tyr Ala Val Thr Gly Ala Arg Thr Ile Asn Gly Gln His Leu
    1265                1270                1275

Tyr Phe Arg Ala Asn Gly Val Gln Val Lys Gly Glu Phe Val Thr
    1280                1285                1290

Asp Arg Tyr Gly Arg Ile Ser Tyr Tyr Asp Ala Asn Ser Gly Glu
    1295                1300                1305

Arg Val Arg Ile Asn
    1310

```
<210> SEQ ID NO 25
<211> LENGTH: 4047
<212> TYPE: DNA
<213> ORGANISM: Streptococcus oralis

<400> SEQUENCE: 25
```

| | | | | | |
|---|---|---|---|---|---|
| atgatcgacg | gcaaaaacta | ctacgtacag | gatgatggca | cggtaaagaa | gaatttcgcg | 60 |
| gtagaactga | atggtcgtat | cctgtatttt | gatgcagaaa | ccggcgctct | ggttgatagc | 120 |
| aacgagtatc | agttccaaca | gggtacgagc | agcctgaaca | tgaattttc | tcagaagaac | 180 |
| gcattctatg | gtacgaccga | taaggatatt | gagactgtgg | atggctacct | gaccgcagat | 240 |
| agctggtatc | gcccgaaatt | catcctgaag | gatggcaaga | cgtggaccgc | gagcacggaa | 300 |
| acggatctgc | gtccgctgtt | gatggcatgg | tggccggaca | gcgtaccca | aatcaactat | 360 |
| ctgaactaca | tgaaccagca | gggtctgggt | gcgggtgcgt | ttgagaacaa | agtggagcag | 420 |
| gccctgctga | cgggtgcaag | ccaacaggta | aacgcaaga | tcgaagagaa | gattggtaaa | 480 |
| gagggtgata | ccaagtggct | gcgcaccctg | atgggtgcgt | tcgtgaaaac | gcaaccaaac | 540 |
| tggaatatca | aaccgagtc | tgaaacgacc | ggcacgaaaa | aggaccatct | gcaaggcggt | 600 |
| gcactgctgt | atacgaacaa | cgagaaatcc | ccgcacgcgg | acagcaaatt | tcgtctgctg | 660 |
| aatcgtaccc | cgaccagcca | aaccggcacg | ccgaagtatt | tcatcgacaa | gtctaacggt | 720 |
| ggctacgaat | ttctgctggc | gaacgatttt | gacaatagca | atcctgcggt | acaagctgag | 780 |
| cagctgaatt | ggctgcacta | catgatgaac | tttggcagca | ttgttgcgaa | tgatccgacc | 840 |
| gcgaatttcg | acggcgttcg | tgtggatgct | gttgataacg | tcaatgcgga | cttgttgcaa | 900 |
| attgcaagcg | attactttaa | gagccgttac | aaagtcggtg | agagcgaaga | gaagcgatc | 960 |
| aagcacctgt | ccatcctgga | agcatggagc | gataacgacc | cggactacaa | caaagatacc | 1020 |
| aagggtgcac | agttggcgat | tgataacaaa | ctgcgcctga | gcctgctgta | ctctttcatg | 1080 |
| cgtaatctga | gcatccgtag | cggtgttgaa | ccgacgatta | ccaatagcct | gaatgaccgt | 1140 |
| tccagcgaaa | agaagaacgg | cgagcgtatg | gcaaattaca | tcttcgtgcg | tgcccacgat | 1200 |
| agcgaggtcc | aaacggtgat | cgccgacatc | attcgcgaaa | acatcaatcc | gaacaccgac | 1260 |
| ggcctgacgt | ttacgatgga | cgagctgaag | caggcattca | agatttacaa | cgaggacatg | 1320 |
| cgcaaggcgg | acaaaaagta | tacccagttt | aacattccta | ccgcacacgc | gctgatgctg | 1380 |
| tctaataagg | attctattac | ccgcgtgtac | tatggtgatc | tgtatactga | cgatggtcag | 1440 |
| tacatggaga | agaaaagccc | gtatcacgat | gcgattgacg | ctctgctgcg | tgcacgtatt | 1500 |
| aaatacgtcg | cgggtggcca | ggatatgaaa | gtgacctata | tgggcgtgcc | gcgtgaagcg | 1560 |
| gataagtgga | gctataacgg | cattctgacc | agcgtgcgct | atggcacggg | cgctaacgaa | 1620 |
| gccacggatg | agggcactgc | ggaaacgcgc | acgcaaggta | tggcagtgat | tgcgagcaat | 1680 |

```
aatccaaatc tgaaactgaa tgaatgggac aagttgcaag tcaacatggg tgcggcgcat    1740
aagaatcaat attaccgtcc ggttctgctg accactaagg acggtatcag ccgttatctg    1800
accgatgaag aagtgcctca gagcctgtgg aaaaagacgg acgcaaacgg tattctgacc    1860
ttcgacatga atgatattgc tggctacagc aacgtgcaag ttagcggtta cctggccgtc    1920
tgggtcccgg tcggtgcgaa ggcggatcaa gatgcgcgca cgaccgcatc caagaagaaa    1980
aatgcgtcgg gtcaggtgta cgaaagcagc gcggctctgg atagccagct gatttacgaa    2040
ggtttcagca actttcaaga ctttgccact cgcgatgatc agtacacgaa caaggtcatt    2100
gcgaaaaacg tgaatctgtt caaagaatgg ggtgtgacca gcttcgagct gccgccgcag    2160
tacgtgagca gccaagatgg cacctttctg gacagcatta tccaaaacgg ctatgcattt    2220
gaagaccgtt acgatatggc gatgagcaag aataacaagt atggtagcct gaaagacctg    2280
ttgaacgcgc tgcgcgcact gcacagcgtc aacattcaag caatcgccga ttgggtgccg    2340
gaccaaattt acaacttgcc gggcaaagag gtggtgaccg caactcgtgt caacaactac    2400
ggcacctacc gtgagggtgc tgaaatcaaa gaaaagctgt atgtcgccaa tagcaagacc    2460
aacgaaaccg atttccaagg taaatacggt ggtgcgttcc tggatgagct gaaggcgaag    2520
tacccggaga ttttcgagcg tgtccaaatc agcaacggcc aaaagatgac taccgatgaa    2580
aagatcacca atggagcgc gaaatacttt aatggcacca atattctggg tcgtggcgcg    2640
tactatgtcc tgaaagattg ggccagcaat gattacctga cgaaccgtaa cggcgagatt    2700
gttttgccga agcaactggt taacaagaat agctataccg ctttgtcag cgacgcgaac    2760 ggcacgaagt tctattctac ctctggctac caggcgaaga acagcttcat tcaagacgaa    2820
aacggtaatt ggtattactt tgacaaacgt ggttatctgg ttacgggcgc acacgagatt    2880
gatggcaagc atgtctactt cctgaaaaac ggtatccaac tgcgtgacag catccgtgag    2940
gatgagaacg gtaatcaata ctattacgac cagaccggcg cacaagtgct gaaccgttac    3000
tacacgacgc acggtcagaa ttggcgctat ttcgatgcga aggtgtttat ggcacgcggc    3060
ctggtaaaga ttggtgacgg ccaacagttt ttcgatgaaa acggttacca ggtcaagggc    3120
aagattgtta gcgcaaaaga cggcaagctg cgctactttg ataaagactc tggcaatgct    3180
gtcattaatc gtttcgcgca gggtgacaat ccgagcgact ggtactattt cggtgtggaa    3240
tttgctaaac tgacgggttt gcaaaagatc ggccagcaga cgctgtattt tgaccaagac    3300
ggtaagcaag tcaaaggtaa gatcgtaact ctgtcggaca aaagcattcg ttacttcgat    3360
gccaacagcg gtgaaatggc ggttggcaag ttcgcggaag gtgcaaagaa tgagtggtat    3420
tatttcgata aaaccggcaa agcggttact ggtttgcaga aaattggtaa gcagaccctg    3480
tactttgacc aggacggtaa acaggttaaa ggcaaggttg tcacgctggc tgataaaagc    3540
atccgctact tcgacgcaga ctccggcgag atggcggtcg gtaagtttgc agagggtgcg    3600
aagaacgagt ggtactattt tgatcagact ggcaaggccg tgactggttt gcaaaagatt    3660
gacaagcaaa ccttgtactt cgaccaggac ggtaaacaag tcaagggtaa gattgtgacg    3720
ttgagcgaca agtcgatccg ttactttgat gctaatagcg gtgagatggc tactaacaaa    3780
ttcgtcgagg gctcgcagaa tgaatggtac tacttcgatc aagcgggtaa ggctgttacg    3840
ggcttgcaac aggtcggtca gcaaactctg tacttcaccc aggatggtaa gcaagtgaag    3900
ggtaaggtcg tggacgtgaa cggtgttctc cgttatttcg acgcaaactc cggtgacatg    3960
gctcgttcta atggattca actggaagat ggcagctgga tgtatttcga ccgtgacggt    4020
cgtggccaga attttggccg taactaa                                       4047
```

<210> SEQ ID NO 26
<211> LENGTH: 1348
<212> TYPE: PRT
<213> ORGANISM: Streptococcus oralis

<400> SEQUENCE: 26

```
Met Ile Asp Gly Lys Asn Tyr Tyr Val Gln Asp Asp Gly Thr Val Lys
1               5                   10                  15

Lys Asn Phe Ala Val Glu Leu Asn Gly Arg Ile Leu Tyr Phe Asp Ala
            20                  25                  30

Glu Thr Gly Ala Leu Val Asp Ser Asn Glu Tyr Gln Phe Gln Gln Gly
        35                  40                  45

Thr Ser Ser Leu Asn Asn Glu Phe Ser Gln Lys Asn Ala Phe Tyr Gly
    50                  55                  60

Thr Thr Asp Lys Asp Ile Glu Thr Val Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
        115                 120                 125

Leu Gly Ala Gly Ala Phe Glu Asn Lys Val Glu Gln Ala Leu Leu Thr
    130                 135                 140

Gly Ala Ser Gln Gln Val Gln Arg Lys Ile Glu Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Lys Lys Asp His Leu Gln Gly Gly Ala Leu Leu Tyr Thr Asn Asn Glu
        195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Ser Asn Pro Ala
                245                 250                 255

Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300

Tyr Phe Lys Ser Arg Tyr Lys Val Gly Glu Ser Glu Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Ala Ile Asp Asn Lys Leu Arg
            340                 345                 350

Leu Ser Leu Leu Tyr Ser Phe Met Arg Asn Leu Ser Ile Arg Ser Gly
        355                 360                 365

Val Glu Pro Thr Ile Thr Asn Ser Leu Asn Asp Arg Ser Ser Glu Lys
```

```
              370                 375                 380
Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                    405                 410                 415

Pro Asn Thr Asp Gly Leu Thr Phe Thr Met Asp Glu Leu Lys Gln Ala
                420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
                500                 505                 510

Tyr Met Gly Val Pro Arg Glu Ala Asp Lys Trp Ser Tyr Asn Gly Ile
                515                 520                 525

Leu Thr Ser Val Arg Tyr Gly Thr Gly Ala Asn Glu Ala Thr Asp Glu
            530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Val Pro Gln Ser
            595                 600                 605

Leu Trp Lys Lys Thr Asp Ala Asn Gly Ile Leu Thr Phe Asp Met Asn
610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
                645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
            675                 680                 685

Ala Thr Arg Asp Asp Gln Tyr Thr Asn Lys Val Ile Ala Lys Asn Val
690                 695                 700

Asn Leu Phe Lys Glu Trp Gly Val Thr Ser Phe Glu Leu Pro Pro Gln
705                 710                 715                 720

Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
                740                 745                 750

Lys Tyr Gly Ser Leu Lys Asp Leu Leu Asn Ala Leu Arg Ala Leu His
            755                 760                 765

Ser Val Asn Ile Gln Ala Ile Ala Asp Trp Val Pro Asp Gln Ile Tyr
770                 775                 780

Asn Leu Pro Gly Lys Glu Val Val Thr Ala Thr Arg Val Asn Asn Tyr
785                 790                 795                 800
```

```
Gly Thr Tyr Arg Glu Gly Ala Glu Ile Lys Glu Lys Leu Tyr Val Ala
            805                 810                 815

Asn Ser Lys Thr Asn Glu Thr Asp Phe Gln Gly Lys Tyr Gly Gly Ala
            820                 825                 830

Phe Leu Asp Glu Leu Lys Ala Lys Tyr Pro Glu Ile Phe Glu Arg Val
            835                 840                 845

Gln Ile Ser Asn Gly Gln Lys Met Thr Thr Asp Glu Lys Ile Thr Lys
            850                 855                 860

Trp Ser Ala Lys Tyr Phe Asn Gly Thr Asn Ile Leu Gly Arg Gly Ala
865                 870                 875                 880

Tyr Tyr Val Leu Lys Asp Trp Ala Ser Asn Asp Tyr Leu Thr Asn Arg
            885                 890                 895

Asn Gly Glu Ile Val Leu Pro Lys Gln Leu Val Asn Lys Asn Ser Tyr
            900                 905                 910

Thr Gly Phe Val Ser Asp Ala Asn Gly Thr Lys Phe Tyr Ser Thr Ser
            915                 920                 925

Gly Tyr Gln Ala Lys Asn Ser Phe Ile Gln Asp Glu Asn Gly Asn Trp
            930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
            965                 970                 975

Ser Ile Arg Glu Asp Glu Asn Gly Asn Gln Tyr Tyr Tyr Asp Gln Thr
            980                 985                 990

Gly Ala Gln Val Leu Asn Arg Tyr Tyr Thr Thr Asp Gly Gln Asn Trp
            995                 1000                1005

Arg Tyr Phe Asp Ala Lys Gly Val Met Ala Arg Gly Leu Val Lys
            1010                1015                1020

Ile Gly Asp Gly Gln Gln Phe Phe Asp Glu Asn Gly Tyr Gln Val
            1025                1030                1035

Lys Gly Lys Ile Val Ser Ala Lys Asp Gly Lys Leu Arg Tyr Phe
            1040                1045                1050

Asp Lys Asp Ser Gly Asn Ala Val Ile Asn Arg Phe Ala Gln Gly
            1055                1060                1065

Asp Asn Pro Ser Asp Trp Tyr Tyr Phe Gly Val Glu Phe Ala Lys
            1070                1075                1080

Leu Thr Gly Leu Gln Lys Ile Gly Gln Gln Thr Leu Tyr Phe Asp
            1085                1090                1095

Gln Asp Gly Lys Gln Val Lys Gly Lys Ile Val Thr Leu Ser Asp
            1100                1105                1110

Lys Ser Ile Arg Tyr Phe Asp Ala Asn Ser Gly Glu Met Ala Val
            1115                1120                1125

Gly Lys Phe Ala Glu Gly Ala Lys Asn Glu Trp Tyr Tyr Phe Asp
            1130                1135                1140

Lys Thr Gly Lys Ala Val Thr Gly Leu Gln Lys Ile Gly Lys Gln
            1145                1150                1155

Thr Leu Tyr Phe Asp Gln Asp Gly Lys Gln Val Lys Gly Lys Val
            1160                1165                1170

Val Thr Leu Ala Asp Lys Ser Ile Arg Tyr Phe Asp Ala Asp Ser
            1175                1180                1185

Gly Glu Met Ala Val Gly Lys Phe Ala Glu Gly Ala Lys Asn Glu
            1190                1195                1200
```

```
Trp Tyr Tyr Phe Asp Gln Thr Gly Lys Ala Val Thr Gly Leu Gln
    1205                1210                1215

Lys Ile Asp Lys Gln Thr Leu Tyr Phe Asp Gln Asp Gly Lys Gln
    1220                1225                1230

Val Lys Gly Lys Ile Val Thr Leu Ser Asp Lys Ser Ile Arg Tyr
    1235                1240                1245

Phe Asp Ala Asn Ser Gly Glu Met Ala Thr Asn Lys Phe Val Glu
    1250                1255                1260

Gly Ser Gln Asn Glu Trp Tyr Tyr Phe Asp Gln Ala Gly Lys Ala
    1265                1270                1275

Val Thr Gly Leu Gln Gln Val Gly Gln Gln Thr Leu Tyr Phe Thr
    1280                1285                1290

Gln Asp Gly Lys Gln Val Lys Gly Lys Val Val Asp Val Asn Gly
    1295                1300                1305

Val Ser Arg Tyr Phe Asp Ala Asn Ser Gly Asp Met Ala Arg Ser
    1310                1315                1320

Lys Trp Ile Gln Leu Glu Asp Gly Ser Trp Met Tyr Phe Asp Arg
    1325                1330                1335

Asp Gly Arg Gly Gln Asn Phe Gly Arg Asn
    1340                1345

<210> SEQ ID NO 27
<211> LENGTH: 4047
<212> TYPE: DNA
<213> ORGANISM: Streptococcus sanguinis

<400> SEQUENCE: 27
atgattgatg gtaaaaagta ttacgtacag gacgacggca cggttaagaa gaatttcgcg      60
gttgagctga atggcaagat cctgtacttc gatgcagaga ctggtgcgtt gattgacagc     120
gcggagtatc aattccaaca aggcaccagc agcctgaata atgagttcac tcaaaagaac     180
gccttttacg gtacgaccga taaggatgtg aaaccattg atggttactt gaccgccgat     240
tcctggtatc gtccgaagtt cattctgaaa gatggcaaaa cctggacggc gagcacggaa     300
attgacttgc gtccgttgtt gatggcgtgg tggccggaca acagaccca ggttagctac     360
ctgaattaca tgaaccagca aggcttgggt gcaggcgcct tcgaaaacaa agtagagcag     420
gcaattctga ccggtgcgtc ccaacaggta aacgtaaaa tcgaagaacg catcggtaaa     480
gagggtgata ccaagtggct gcgtaccctg atgggtgcat ttgtaaagac ccagccgaac     540
tggaacatta agaccgagtc cgaaaccact ggcacgaata agatcatct gcaaggtggc     600
gcactgctgt atagcaattc cgacaagacg agccatgcca actctaagta ccgtatcctg     660
aaccgcaccc cgaccaacca aacgggcacg ccgaaatact tattgacaa gagcaatggt     720
ggttatgaat ttctgctggc gaatgacttt gacaatagca atccggcagt gcaagcggaa     780
cagctgaact ggttgcactt tatgatgaat tttggctcca tcgttgcaaa tgatccgacg     840
gccaacttcg acggcgtccg cgttgacgct gtggataacg tgaatgcgga tctgttgcaa     900
attgcgagcg actatttcaa gagccgctat aaagtcggcg aaagcgaaga agaggccatt     960
aagcacctgt ccatcctgga agcgtggagc gacaacgacc cggactacaa caaggatact    1020
aaaggtgccc aactgccgat cgacaacaaa ctgcgtctga gcctgctgta ctccttcatg    1080
cgtaagctga gcatccgtag cggcgtcgag ccgaccatca ccaactctct gaatgatcgc    1140
agcacgagga agaagaatgg tgagcgtatg caaactata tcttcgttcg tgcacatgat    1200
agcgaggtgc aaacggtcat cgccgacatt atccgtgaga acatcaatcc gaataccgac    1260
```

```
ggcctgacgt tcacgatgga tgaactgaag caggccttta aaatttacaa tgaggatatg   1320
cgtaaagccg acaaaaagta cacgcagttc aatatcccga ccgcgcacgc gctgatgctg   1380
agcaacaaag attctatcac ccgcgtttac tacggtgacc tgtatacgga tgacggtcag   1440
tatatggaaa agaaaagccc gtatcacgac gccattgacg ctctgctgcg tgcgcgtatc   1500
aaatatgttg cgggtggtca ggacatgaag gtgacctata tgggcgtgcc gcgtgaggca   1560
gataaatgga gctataacgg catcctgacc agcgttcgtt atggtacggg tgccaacgag   1620
gcaaccgacg agggtacggc agaaacccgt acccagggca tggccgtcat tgccagcaac   1680
aatccgaacc tgaaactgaa cgagtgggac aagttgcagg tcaacatggg tgcagctcac   1740
aaaaaccaat actatcgtcc ggtgctgctg accaccaagg acggcatctc gcgctacctg   1800
accgacgaag aagtcccgca gagcctgtgg aaaaagaccg atgcgaacgg catcttgacg   1860
tttgacatga atgatattgc gggttacagc aacgtccaag tgagcggtta tctggccgtc   1920
tgggttcctg tgggtgcgaa ggcggaccag gacgctcgtg ttacggcatc taagaagaaa   1980
aatgcctctg ccaagtttta cgaaagcagc gcagccctgg actcccagct gatctatgag   2040
ggcttcagca ttttcagga ctttgccacc cgtgacgacc agtacactaa caaggttatc   2100
gcgaaaaacg tcaatctgtt taaagagtgg ggcgtcacca gcttcgaatt gccgccacag   2160
tatgtgagca gccaagacgg tacgttcctg gatagcatca tccagaatgg ttatgcattc   2220
gaagatcgct atgatatggc gatgagcaaa aacaataagt acggtagctt gaacgacctg   2280
ttgaacgcct gcgtgcact gcatagcgtg aatatccaag cgattgcgga ttgggtgccg   2340
gaccagattt acaatctgcc gggtaaagaa gttgtcactg caacccgtgt taacaattat   2400
ggcacgtatc gtgagggtag cgagattaaa gagaacctgt acgttgctaa caccaaaacc   2460
aatggtacgg actaccaagg taagtatggt ggtgcgttct tggacgagct gaaagccaaa   2520
taccctgaga tttttgagcg cgtccaaatc agcaacggcc agaagatgac cacccgacgag   2580 aagattacga aatggtccgc caaacacttt aacggcacga cattctgggt cgtggtgcg   2640 tattatgtgc tgaaagactg ggcgagcaac gagtacctga ataacaaaaa tggcgagatg   2700
gttctgccga agcagctggt taataaaaat gcatataccg gcttcgtcag cgacgcgagc   2760
ggcaccaaat actattctac cagcggctat caggctcgta atagctttat tcaagatgaa   2820
aatggtaatt ggtactactt caataaccgt ggttatttgg tgacgggtgc acaggaaatc   2880
gacggtaagc aactgtattt cctgaaaaac ggcattcagc tgcgtgattc tctgcgtgag   2940
gacgaaaacg gcaaccagta ttactatgat aagacgggtg cgcaagttct gaatcgttat   3000
tacactacgg acggccaaaa ttggcgctac ttcgacgtta aaggcgtcat ggcccgtggt   3060
ctggtcacga tgggtggtaa ccaacaattc tttgaccaaa acggttacca ggttaaaggc   3120
aaaattgcgc gtgcaaaaga cggtaaactg cgttacttcg ataaagacag cggtaatgcg   3180
gcagctaacc gttcgcccca aggcgataac cctagcgact ggtactattt cggtgcagat   3240
ggtgttgcgg ttacgggcct gcaaaaggtt ggtcagcaaa ctctgtactt tgatcaggac   3300
ggcaagcagg tgaaaggtaa agttgttacc ttggcggaca aaagcattcg ttatttcgat   3360
gcaaacagcg cgagatggc ggtgaacaag tttgtggaag gtgctaagaa cgtgtggtac   3420
tacttcgatc aagcaggcaa agcggtgacc ggcctgcaaa ccatcaataa acaagtgctg   3480
tatttcgacc aggatggtaa acaagtcaaa ggtaaggtgg tcacgctggc tgataagtct   3540
atccgctact tcgacgcgaa cagcggtgag atggcagtgg gcaaattcgc cgaaggcgca   3600
```

-continued

```
aagaatgagt ggtattactt tgaccaggcg ggcaaggctg ttaccggtct gcaaaagatc    3660
ggccaacaga cgctgtattt cgaccagaac ggtaaacagg ttaagggtaa agtggtcacc    3720
ctggcggata agagcatccg ctatttcgac gctaactctg gcgaaatggc aagcaataag    3780
ttcgttgagg gtgccaaaaa tgaatggtac tatttcgatc aggctggcaa ggcagtgacg    3840
ggtctgcaac aaattggcca gcagaccctg tattttgacc agaatggcaa acaggtgaag    3900
ggtaagattg tgtatgttaa tggtgcgaat cgctactttg atgccaatag cggtgaaatg    3960
gcgcgtaaca agtggattca gctggaagat ggcagctgga tgtattttga ccgcaatggt    4020
cgtggtcgtc gtttcggttg gaactaa                                       4047
```

<210> SEQ ID NO 28
<211> LENGTH: 1348
<212> TYPE: PRT
<213> ORGANISM: Streptococcus sanguinis

<400> SEQUENCE: 28

```
Met Ile Asp Gly Lys Lys Tyr Tyr Val Gln Asp Gly Thr Val Lys
1               5                  10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
        195                 200                 205

Lys Thr Ser His Ala Asn Ser Lys Tyr Arg Ile Leu Asn Arg Thr Pro
    210                 215                 220

Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asn Ser Asn Pro Ala
                245                 250                 255

Val Gln Ala Glu Gln Leu Asn Trp Leu His Phe Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
```

```
           290                 295                 300
Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
                340                 345                 350

Leu Ser Leu Leu Tyr Ser Phe Met Arg Lys Leu Ser Ile Arg Ser Gly
                355                 360                 365

Val Glu Pro Thr Ile Thr Asn Ser Leu Asn Asp Arg Ser Thr Glu Lys
                370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
                420                 425                 430

Phe Lys Ile Tyr Asn Glu Asp Met Arg Lys Ala Asp Lys Lys Tyr Thr
                435                 440                 445

Gln Phe Asn Ile Pro Thr Ala His Ala Leu Met Leu Ser Asn Lys Asp
                450                 455                 460

Ser Ile Thr Arg Val Tyr Tyr Gly Asp Leu Tyr Thr Asp Asp Gly Gln
465                 470                 475                 480

Tyr Met Glu Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
                500                 505                 510

Tyr Met Gly Val Pro Arg Glu Ala Asp Lys Trp Ser Tyr Asn Gly Ile
                515                 520                 525

Leu Thr Ser Val Arg Tyr Gly Thr Gly Ala Asn Glu Ala Thr Asp Glu
                530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
                580                 585                 590

Lys Asp Gly Ile Ser Arg Tyr Leu Thr Asp Glu Glu Val Pro Gln Ser
                595                 600                 605

Leu Trp Lys Lys Thr Asp Ala Asn Gly Ile Leu Thr Phe Asp Met Asn
610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Val Thr Ala
                645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
                675                 680                 685

Ala Thr Arg Asp Asp Gln Tyr Thr Asn Lys Val Ile Ala Lys Asn Val
                690                 695                 700

Asn Leu Phe Lys Glu Trp Gly Val Thr Ser Phe Glu Leu Pro Pro Gln
705                 710                 715                 720
```

```
Tyr Val Ser Ser Gln Asp Gly Thr Phe Leu Asp Ser Ile Ile Gln Asn
                725                 730                 735

Gly Tyr Ala Phe Glu Asp Arg Tyr Asp Met Ala Met Ser Lys Asn Asn
                740                 745                 750

Lys Tyr Gly Ser Leu Asn Asp Leu Leu Asn Ala Leu Arg Ala Leu His
                755                 760                 765

Ser Val Asn Ile Gln Ala Ile Ala Asp Trp Val Pro Asp Gln Ile Tyr
770                 775                 780

Asn Leu Pro Gly Lys Glu Val Val Thr Ala Thr Arg Val Asn Asn Tyr
785                 790                 795                 800

Gly Thr Tyr Arg Glu Gly Ser Glu Ile Lys Asn Leu Tyr Val Ala
                805                 810                 815

Asn Thr Lys Thr Asn Gly Thr Asp Tyr Gln Gly Lys Tyr Gly Gly Ala
                820                 825                 830

Phe Leu Asp Glu Leu Lys Ala Lys Tyr Pro Glu Ile Phe Glu Arg Val
                835                 840                 845

Gln Ile Ser Asn Gly Gln Lys Met Thr Thr Asp Glu Lys Ile Thr Lys
                850                 855                 860

Trp Ser Ala Lys His Phe Asn Gly Thr Asn Ile Leu Gly Arg Gly Ala
865                 870                 875                 880

Tyr Tyr Val Leu Lys Asp Trp Ala Ser Asn Glu Tyr Leu Asn Asn Lys
                885                 890                 895

Asn Gly Glu Met Val Leu Pro Lys Gln Leu Val Asn Lys Asn Ala Tyr
                900                 905                 910

Thr Gly Phe Val Ser Asp Ala Ser Gly Thr Lys Tyr Tyr Ser Thr Ser
                915                 920                 925

Gly Tyr Gln Ala Arg Asn Ser Phe Ile Gln Asp Glu Asn Gly Asn Trp
                930                 935                 940

Tyr Tyr Phe Asn Asn Arg Gly Tyr Leu Val Thr Gly Ala Gln Glu Ile
945                 950                 955                 960

Asp Gly Lys Gln Leu Tyr Phe Leu Lys Asn Gly Ile Gln Leu Arg Asp
                965                 970                 975

Ser Leu Arg Glu Asp Glu Asn Gly Asn Gln Tyr Tyr Asp Lys Thr
                980                 985                 990

Gly Ala Gln Val Leu Asn Arg Tyr Tyr Thr Thr Asp Gly Gln Asn Trp
                995                 1000                1005

Arg Tyr Phe Asp Val Lys Gly Val Met Ala Arg Gly Leu Val Thr
        1010                1015                1020

Met Gly Gly Asn Gln Gln Phe Phe Asp Gln Asn Gly Tyr Gln Val
        1025                1030                1035

Lys Gly Lys Ile Ala Arg Ala Lys Asp Gly Lys Leu Arg Tyr Phe
        1040                1045                1050

Asp Lys Asp Ser Gly Asn Ala Ala Ala Asn Arg Phe Ala Gln Gly
        1055                1060                1065

Asp Asn Pro Ser Asp Trp Tyr Tyr Phe Gly Ala Asp Gly Val Ala
        1070                1075                1080

Val Thr Gly Leu Gln Lys Val Gly Gln Gln Thr Leu Tyr Phe Asp
        1085                1090                1095

Gln Asp Gly Lys Gln Val Lys Gly Lys Val Val Thr Leu Ala Asp
        1100                1105                1110

Lys Ser Ile Arg Tyr Phe Asp Ala Asn Ser Gly Glu Met Ala Val
        1115                1120                1125
```

```
Asn Lys Phe Val Glu Gly Ala Lys Asn Val Trp Tyr Tyr Phe Asp
    1130                1135                1140

Gln Ala Gly Lys Ala Val Thr Gly Leu Gln Thr Ile Asn Lys Gln
    1145                1150                1155

Val Leu Tyr Phe Asp Gln Asp Gly Lys Gln Val Lys Gly Lys Val
    1160                1165                1170

Val Thr Leu Ala Asp Lys Ser Ile Arg Tyr Phe Asp Ala Asn Ser
    1175                1180                1185

Gly Glu Met Ala Val Gly Lys Phe Ala Glu Gly Ala Lys Asn Glu
    1190                1195                1200

Trp Tyr Tyr Phe Asp Gln Ala Gly Lys Ala Val Thr Gly Leu Gln
    1205                1210                1215

Lys Ile Gly Gln Gln Thr Leu Tyr Phe Asp Gln Asn Gly Lys Gln
    1220                1225                1230

Val Lys Gly Lys Val Val Thr Leu Ala Asp Lys Ser Ile Arg Tyr
    1235                1240                1245

Phe Asp Ala Asn Ser Gly Glu Met Ala Ser Asn Lys Phe Val Glu
    1250                1255                1260

Gly Ala Lys Asn Glu Trp Tyr Tyr Phe Asp Gln Ala Gly Lys Ala
    1265                1270                1275

Val Thr Gly Leu Gln Gln Ile Gly Gln Gln Thr Leu Tyr Phe Asp
    1280                1285                1290

Gln Asn Gly Lys Gln Val Lys Gly Lys Ile Val Tyr Val Asn Gly
    1295                1300                1305

Ala Asn Arg Tyr Phe Asp Ala Asn Ser Gly Glu Met Ala Arg Asn
    1310                1315                1320

Lys Trp Ile Gln Leu Glu Asp Gly Ser Trp Met Tyr Phe Asp Arg
    1325                1330                1335

Asn Gly Arg Gly Arg Arg Phe Gly Trp Asn
    1340                1345

<210> SEQ ID NO 29
<211> LENGTH: 4023
<212> TYPE: DNA
<213> ORGANISM: unknown
<220> FEATURE:
<223> OTHER INFORMATION: unknown Streptococcus sp. C150

<400> SEQUENCE: 29
atgatcgacg gcaaatacta ctacgtaaac gaggacggca gccacaaaga gaatttcgcg     60
atcacggtta atggtcaact gctgtatttt ggtaaggatg gcgcgctgac cagcagcagc    120
acgtacagct tcacccaagg cactaccaat attgtggacg gttttagcat taacaaccgt    180
gcgtatgact ccagcgaggc ctctttcgag ctgattgacg ttatctgac tgcggactct    240 tggtaccgtc cggcgagcat tatcaaagac ggtgtgacgt ggcaagcatc caccgccgag    300
gacttccgcc cgttgctgat ggcgtggtgg ccgaacgttg atactcaggt gaactacctg    360
aactacatgt ccaaagtctt taatctggat gctaaataca gctcgactga taaacaggaa    420
accctgaagg tggcggcgaa agatatccag atcaaaattg aacaaaagat tcaggcggaa    480
aagtccacgc aatggctgcg tgaaacgatc agcgcctttg taaaacccca gccgcaatgg    540
aacaaagaga ctgagaacta cagcaagggc ggtggtgagg accatctgca aggtggtgcc    600
ctgctgtatg ttaatgactc tcgtacccg tgggcgaaca gcaactatcg tttgctgaac    660
cgcacggcga ccaaccagac cggtacgatc gacaagagca tcctggacga gcagagcgat    720
```

```
ccgaatcaca tgggtggttt tgatttcttg ctggctaatg acgttgactt gagcaatccg    780
gtcgtccagg cggaacaact gaatcagatc cactacctga tgaattgggg ttctattgtc    840
atgggtgata agacgcgaa ttttgacggt attcgtgtag acgcggtgga taatgttgat    900
gcggacatgc tgcaattgta caccaactat ttccgcgaat actatggtgt caacaaaagc    960
gaggcaaacg cgctggcgca cattagcgtc ctggaagcct ggagcctgaa tgacaaccat   1020
tacaatgata agactgatgt tgcggcgctg gcaatggaga ataagcagcg cttggcactg   1080
ttgtttagcc tggcgaaacc gattaaagaa cgcacgcctg ccgtgtctcc gctgtacaac   1140
aatacgttta acaccactca gcgtgatgaa aagacggact ggatcaataa agatggttcg   1200
aaagcctaca atgaggatgg cactgtcaag aaaagcacca tcggcaagta taacgagaag   1260
tatggtgatg ctagcggcaa ctacgttttc atccgcgctc acgacaataa cgtgcaagac   1320
atcatcgcgg agatcattaa gaaagagatt aacgagaaat ctgacggttt taccattacg   1380
gattcggaga tgaagcgtgc atttgagatc tataacaaag acatgctgtc taatgacaaa   1440
aagtacacgc tgaataacat cccggcggcg tacgcggtta tgctgcaaaa catggaaacg   1500
attacccgcg tgtattacgg cgatctgtac acggacgacg gtaattacat ggaagcgaaa   1560
agcccgtact acgatacgat tgttaacttg atgaagtctc gcatcaaata cgtgagcggt   1620
ggccaggcgc agcgcagcta ctggctgccg accgatggta agatggataa gtcggatgtt   1680
gagctgtacc gtacgaacga agtgtacacg agcgtccgtt acggcaaaga cattatgacc   1740
gccgatgaca cgcaaggtag caaatacagc cgtaccagcg gtcaggtgac cctggtcgtc   1800
aacaacccaa aactgacctt ggaccaaagc gcaaagctga acgtggttat gggcaagatt   1860
catgctaatc agaagtaccg cgcactgatt gtcggtaccc cgaacggtat taagaatttc   1920
accagcgacg cagaggctat tgccgcaggc tatgtcaaag aaaccgatgg caatggcgtg   1980
ctgaccttcg gtgcaaacga catcaagggt tatgaaactt tcgatatgag cggcttcgtc   2040
gctgtttggg ttccggtcgg tgcgagcgac gaccaagata ttcgtgtggc ggcgtctacg   2100
gcagcaaaga aagagggtga gctgacgctg aaagcgaccg aagcctatga ctcccaactg   2160
atctatgaag ctttagcaa tttccagacc atcccagatg gcagcgatcc ttctgtttat   2220
accaatcgta agatcgcgga aaatgttgat tgttcaagaa gctggggtgt cacgagcttc   2280
gaaatggctc cgcagttcgt ttctgcggac gatggcacgt ttctggacag cgtcattcaa   2340
aacggctatg cgttcgcaga ccgttatgat ctggccatga gcaaaaacaa taagtacggt   2400
agcaaagaag atctgcgtaa cgcgctgaag gcactgcaca aagcaggcat tcaggcgatt   2460
gcagattggg tgccagacca aatctaccag ctgcctggca agaagttgt tactgccacc   2520 cgcacggacg tgctggtcg caaaatcagc gatgcaatca tcgatcattc cctgtacgtt   2580
gcgaactcca agagctccgg taaggactac caagcgaagt acggtggcga gttcttggcg   2640
gaactgaagg cgaaataccc ggaaatgttc aaagtgaaca tgattagcac cggcaaaccg   2700
attgatgata gcgtgaaact gaagcagtgg aaagcagaat acttcaacgg caccaatgtg   2760
ctggatcgcg gtgtcggtta tgttctgagc gatgaggcaa ccggtaagta tttcaccgtt   2820
accaaagagg gtaactttat cccgttgcag ctgaagggta acaagaaggt gattaccggc   2880
ttttccagcg acggtaaggg cattacctat ttcggtacta gcggtaacca agctaaatcc   2940
gcgttcgtca cttttaacgg taacacgtac tacttcgacg cacgtggcca catggttacc   3000
aacggtgagt actcgccgaa tggtaaagat gtgtatcgtt ttctgccgaa cggcattatg   3060
ctgagcaacg cgttctatgt tgacggcaat ggcaacacct acctgtacaa ctccaaaggc   3120
```

```
caaatgtata aaggtggcta tagcaaattt gacgtcacgg aaacgaagga cggtaaagag    3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caaatggtac cattttgatg ctaacggtgt cgcggctact    3420
ggcgcacagg ttatcaacgg tcagcacctg tacttcaatg aagatggctc tcaagtaaaa    3480
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgg ttactggtgc acaggtgatt aatggccagc acttgttctt caaagaggat    3660
ggcagccagg tcaagggcga ctttgtgaag aatagcgacg gcacctactc caagtatgac    3720
gctgcgagcg gcgaacgtct gaccaacgag ttcttcacta cgggcgacaa tcattggtac    3780
tatattggcg ccaacggtaa gaccgttacc ggtgaagtta agattggtga cgacacgtat    3840
ttcttcgcaa aagacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt tgttttctt cgacaaaaac ggcctggctt acccaccgga gaatatgaac    4020
tga                                                                  4023
```

<210> SEQ ID NO 30
<211> LENGTH: 1340
<212> TYPE: PRT
<213> ORGANISM: unknown
<220> FEATURE:
<223> OTHER INFORMATION: unknown Streptococcus sp. C150

<400> SEQUENCE: 30

```
Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Ser Ser Thr Asp Lys Gln Glu Thr Leu Lys Val
    130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190
```

```
Glu Asp His Leu Gln Gly Gly Ala Leu Leu Tyr Val Asn Asp Ser Arg
            195                 200                 205

Thr Pro Trp Ala Asn Ser Asn Tyr Arg Leu Leu Asn Arg Thr Ala Thr
210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
        275                 280                 285

Asp Gly Ile Arg Val Asp Ala Val Asp Asn Val Asp Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Val Ala Ala Leu Ala Met
            340                 345                 350

Glu Asn Lys Gln Arg Leu Ala Leu Leu Phe Ser Leu Ala Lys Pro Ile
        355                 360                 365

Lys Glu Arg Thr Pro Ala Val Ser Pro Leu Tyr Asn Asn Thr Phe Asn
    370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Lys Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
        435                 440                 445

Glu Ile Asn Glu Lys Ser Asp Gly Phe Thr Ile Thr Asp Ser Glu Met
    450                 455                 460

Lys Arg Ala Phe Glu Ile Tyr Asn Lys Asp Met Leu Ser Asn Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly Asn Tyr Met Glu Ala Lys Ser Pro Tyr Tyr Asp Thr Ile Val
        515                 520                 525

Asn Leu Met Lys Ser Arg Ile Lys Tyr Val Ser Gly Gly Gln Ala Gln
    530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
            580                 585                 590

Ser Gly Gln Val Thr Leu Val Val Asn Asn Pro Lys Leu Thr Leu Asp
        595                 600                 605

Gln Ser Ala Lys Leu Asn Val Val Met Gly Lys Ile His Ala Asn Gln
```

```
            610                 615                 620
Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
                675                 680                 685

Ser Asp Asp Gln Asp Ile Arg Val Ala Ser Thr Ala Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
                755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
                820                 825                 830

Gly Lys Glu Val Val Thr Ala Thr Arg Thr Asp Gly Ala Gly Arg Lys
                835                 840                 845

Ile Ser Asp Ala Ile Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Asp Arg Gly Val Gly Tyr Val
                915                 920                 925

Leu Ser Asp Glu Ala Thr Gly Lys Tyr Phe Thr Val Thr Lys Glu Gly
930                 935                 940

Asn Phe Ile Pro Leu Gln Leu Lys Gly Asn Lys Val Ile Thr Gly
945                 950                 955                 960

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
                980                 985                 990

Asp Ala Arg Gly His Met Val Thr Asn Gly Glu Tyr Ser Pro Asn Gly
                995                 1000                1005

Lys Asp Val Tyr Arg Phe Leu Pro Asn Gly Ile Met Leu Ser Asn
    1010                1015                1020

Ala Phe Tyr Val Asp Gly Asn Gly Asn Thr Tyr Leu Tyr Asn Ser
    1025                1030                1035
```

-continued

Lys Gly Gln Met Tyr Lys Gly Gly Tyr Ser Lys Phe Asp Val Thr
1040            1045                1050

Glu Thr Lys Asp Gly Lys Glu Ser Lys Val Val Lys Phe Arg Tyr
1055            1060                1065

Phe Thr Asn Glu Gly Val Met Ala Lys Gly Val Thr Val Val Asp
1070            1075                1080

Gly Phe Thr Gln Tyr Phe Asn Glu Asp Gly Ile Gln Ser Lys Asp
1085            1090                1095

Glu Leu Val Thr Tyr Asn Gly Lys Thr Tyr Tyr Phe Glu Ala His
1100            1105                1110

Thr Gly Asn Ala Ile Lys Asn Thr Trp Arg Asn Ile Lys Gly Lys
1115            1120                1125

Trp Tyr His Phe Asp Ala Asn Gly Val Ala Ala Thr Gly Ala Gln
1130            1135                1140

Val Ile Asn Gly Gln His Leu Tyr Phe Asn Glu Asp Gly Ser Gln
1145            1150                1155

Val Lys Gly Ser Ile Val Lys Asn Ala Asp Gly Thr Phe Ser Lys
1160            1165                1170

Tyr Lys Asp Ser Ser Gly Asp Leu Val Val Asn Glu Phe Phe Thr
1175            1180                1185

Thr Gly Asp Asn Val Trp Tyr Tyr Ala Gly Ala Asn Gly Lys Thr
1190            1195                1200

Val Thr Gly Ala Gln Val Ile Asn Gly Gln His Leu Phe Phe Lys
1205            1210                1215

Glu Asp Gly Ser Gln Val Lys Gly Asp Phe Val Lys Asn Ser Asp
1220            1225                1230

Gly Thr Tyr Ser Lys Tyr Asp Ala Ala Ser Gly Glu Arg Leu Thr
1235            1240                1245

Asn Glu Phe Phe Thr Thr Gly Asp Asn His Trp Tyr Tyr Ile Gly
1250            1255                1260

Ala Asn Gly Lys Thr Val Thr Gly Glu Val Lys Ile Gly Asp Asp
1265            1270                1275

Thr Tyr Phe Phe Ala Lys Asp Gly Lys Gln Leu Lys Gly Gln Ile
1280            1285                1290

Val Thr Thr Arg Ser Gly Arg Ile Ser Tyr Tyr Phe Gly Asp Ser
1295            1300                1305

Gly Lys Lys Ala Ile Ser Thr Trp Val Glu Ile Gln Pro Gly Val
1310            1315                1320

Phe Val Phe Phe Asp Lys Asn Gly Leu Ala Tyr Pro Pro Glu Asn
1325            1330                1335

Met Asn
1340

<210> SEQ ID NO 31
<211> LENGTH: 4029
<212> TYPE: DNA
<213> ORGANISM: Streptococcus salivarius

<400> SEQUENCE: 31
atgaacattg atggtaaata ttactatgtt aatgaagatg gttcacacaa agaaaacttt    60
gccattactg taaatggtca attgctttac ttcggtaaag atggtgctct tacaagttca   120
tcaacatact ctttcacacc aggaacaaca aatattgttg atggtttctc aataaataac   180
cgtgcctacg attcatctga agctagcttt gaattgattg atggttattt gactgcagat   240

```
agctggtacc gtccagcttc tatcatcaaa gatggtgtaa cttggcaagc atcaactgca    300
gaagatttcc gtccactttt gatggcttgg tggccaaatg tagatacaca agttaactac    360
ttgaactaca tgtctaaagt atttaacttg gatgctaaat attcaagtac agataagcaa    420
gaaactttga aagttgctgc taaggacatt caaatcaaga ttgagcaaaa gattcaggct    480
gaaaaatcaa cacaatggtt gcgtgaaact atctctgcct tgttaagac acaaccacaa     540 tggaacaaag aaactgaaaa ctactctaaa ggtggcggcg aagatcacct tcaaggtggt    600
gcccttcttt atgtgaatga ttcacgtaca ccatgggcga attctgacta cgtcgtttg     660 aaccgtacag caactaacca gactggtaca attgataaat caattcttga tgagcaatca    720
gatccaaacc acatgggtgg tttcgacttc ttgctagcta atgacgtaga tttgtcaaac    780
ccagttgttc aagcggaaca attgaaccaa atccactacc ttatgaactg gggttcaatc    840
gttatgggtg acaaggatgc taacttcgat ggtatccgtg tcgacgcggt agataatgtc    900
gatgcagaca tgcttcaact ctacacaaac tacttccgtg agtactatgg tgttaacaaa    960
tctgaagcaa acgctcttgc tcacatctca gtccttgaag catggagcct taatgacaac   1020
cactacaatg acaagacaga tggcgctgcg cttgctatgg aaaacaaaca acgtttggct   1080
ctcctcttct cattggctaa accaatcaaa gaacgtacac cagctgtaag tcctttgtat   1140
aacaatactt tcaacacgac acaacgtgat gaaaagactg attggattaa caaagatgga   1200
agcaaggcct ataacgaaga cggaacagtt aaacagtcta caatcggtaa atataacgag   1260
aaatacggag atgcgtcagg aaattacgtc tttatccgtg cccatgataa caacgttcaa   1320
gatattattg ctgaaatcat caagaaagaa atcaatccaa aatcagatgg tttcacgatt   1380
actgatgctg aaatgaagca agcctttgag atttacaaca aagacatgct cagcagcgac   1440
aaaaaatata cgcttaacaa catcccagcg gcttacgcgg ttatgttgca aaacatggaa   1500
actatcactc gtgtctacta tggagacctt tatacagatg atggtcacta catggaaact   1560
aagtctccat attcgatac cattgttaac ttgatgaaga gtcgtatcaa gtatgtatct     1620
ggtgggcaag cacaacgttc atactggttt ccaactgatg gtaagatgga caattcagat   1680
gttgaacttt accgcacaaa tgaagtctac acttcagtac gttatggtaa agacattatg   1740
acagctaatg atacagaagg ttctaaatac agccgtactt ctggtcaggt aacacttgta   1800
gctaacaatc caaaattgaa tttggatcaa tcagctaaac ttaatgttga atgggtaaa    1860 atccatgcca accaaaaata ccgtgctttg attgttggta cagctgatgg tatcaagaac   1920
tttacatctg atgcagatgc aatcgcagca ggttacgtta agaaacaga cagcaacggt    1980 gtcttgactt tcggtgctaa tgacatcaag ggttatgaaa catttgatat gtctggtttc   2040
gtagcagttt gggttccagt tggagcttca gataatcaag atatccgagt agcgccttca   2100
acagaagcta aaaagaggg tgaattgact cttaaagcga ctgaagctta tgattcacaa     2160
ttaatctacg aaggcttctc taactttcaa actattccag atggttcaga tccttcagtc   2220
tatactaacc gtaagattgc tgaaaatgtt gatttgttca aatcatgggg tgtaacatca   2280
tttgaaatgg cacctcaatt tgtatctgct gacgatggta ccttccttga ctcagttatc   2340
caaaatggtt atgcctttgc agaccgttac gatcttgcca tgagtaagaa caataaatac   2400
ggttctaaag aagatctacg tgatgctctt aaagcacttc ataaggctgg tattcaagca   2460
atcgctgact gggttccaga ccaaatttac caattgccag gtaaagaagt tgtaacagcg   2520
actcgtactg atggtgctgg tcgtaagatt gcggacgcta tcattgacca ctcactttat   2580
```

```
gtggctaact ctaagtcatc aggcaaagat taccaagcta aatacggtgg tgaattcttg      2640
gctgaactta aagctaagta ccctgaaatg ttcaaggtaa acatgatttc aactggtaaa      2700
ccaattgatg attctgttaa attgaaacaa tggaaggctg aatacttcaa cggaacaaac      2760
gttcttgaac gtggtgttgg ctatgtactt agcgatgaag caactggtaa gtatttcact      2820
gtcactaaag aaggtaactt cattcctctt caattgacag gtaaagaaaa ggttattact      2880
ggattctcaa gtgatggtaa aggaatcact tacttcggta caagtggtac acaagctaaa      2940
tctgcctttg taaccttcaa tggtaacact tactactttg atgctcgtgg tcacatggtt      3000
actaacagtg aatactcacc aaatggtaaa gacgtttatc gtttcttacc aaatggtatc      3060
atgttgagta atgccttcta cattgatgct aatggtaata cctacctttta taactctaaa      3120 ggtcaaatgt acaagggtgg ttacactaaa tttgatgttt ctgaaactga taaagacggt      3180
aaagaatcta aggttgtgaa attccgttac ttcactaatg aaggtgtcat ggccaaaggt      3240
gttacggtta ttgatggttt cacacaatat tttggagaag acggtttcca agctaaagat      3300
aagttagtaa cctttaaagg taaaacttat tactttgacg cacacactgg taatggtatc      3360
aaggatactt ggagaaatat caatggtaag tggtactact ttgatgcaaa cggtgttgct      3420
gctacaggtg cacaagtcat caatggtcaa aaacttact tcaatgaaga tggaagccaa      3480
gttaaaggtg gcgttgttaa gaatgcagat ggtacttaca gcaagtacaa agaaggtttt      3540
ggagagctag tgactaacga attcttcaca actgatggca atgtttggta ctatgcaggc      3600
gctaatggta agactgttac aggtgcacaa gtcatcaatg ccaacaccct atactttaat      3660
gcagacggaa gccaagttaa gggtggtgtt gttaagaatg cagatggtac ttatagtaag      3720
tataatgctt caacaggtga acgcttgact aatgagtttt tcacaacagg cgacaacaac      3780
tggtactaca ttggtgctaa tggtaagtca gtgactggtg aagttaaaat tggtgacgat      3840
acttatttct tcgctaagga tggtaaacaa gtaaaaggtc aaacagtaag tgctggcaat      3900
ggtcgaatta gctattacta tggtgatagt ggtaagagag ctgttagcac atggatagaa      3960
attcaaccag gagtttacgt ttactttgat aagaatggtc ttgcttatcc acctagagtg      4020
ctaaactaa                                                              4029
```

<210> SEQ ID NO 32
<211> LENGTH: 1342
<212> TYPE: PRT
<213> ORGANISM: Streptococcus salivarius

<400> SEQUENCE: 32

```
Met Asn Ile Asp Gly Lys Tyr Tyr Tyr Val Asn Glu Asp Gly Ser His
1               5                   10                  15

Lys Glu Asn Phe Ala Ile Thr Val Asn Gly Gln Leu Leu Tyr Phe Gly
            20                  25                  30

Lys Asp Gly Ala Leu Thr Ser Ser Thr Tyr Ser Phe Thr Pro Gly
        35                  40                  45

Thr Thr Asn Ile Val Asp Gly Phe Ser Ile Asn Asn Arg Ala Tyr Asp
    50                  55                  60

Ser Ser Glu Ala Ser Phe Glu Leu Ile Asp Gly Tyr Leu Thr Ala Asp
65                  70                  75                  80

Ser Trp Tyr Arg Pro Ala Ser Ile Ile Lys Asp Gly Val Thr Trp Gln
                85                  90                  95

Ala Ser Thr Ala Glu Asp Phe Arg Pro Leu Leu Met Ala Trp Trp Pro
            100                 105                 110
```

```
Asn Val Asp Thr Gln Val Asn Tyr Leu Asn Tyr Met Ser Lys Val Phe
            115                 120                 125
Asn Leu Asp Ala Lys Tyr Ser Ser Thr Asp Lys Gln Glu Thr Leu Lys
        130                 135                 140
Val Ala Ala Lys Asp Ile Gln Ile Lys Ile Glu Gln Lys Ile Gln Ala
145                 150                 155                 160
Glu Lys Ser Thr Gln Trp Leu Arg Glu Thr Ile Ser Ala Phe Val Lys
                165                 170                 175
Thr Gln Pro Gln Trp Asn Lys Glu Thr Glu Asn Tyr Ser Lys Gly Gly
            180                 185                 190
Gly Glu Asp His Leu Gln Gly Gly Ala Leu Leu Tyr Val Asn Asp Ser
        195                 200                 205
Arg Thr Pro Trp Ala Asn Ser Asp Tyr Arg Arg Leu Asn Arg Thr Ala
210                 215                 220
Thr Asn Gln Thr Gly Thr Ile Asp Lys Ser Ile Leu Asp Glu Gln Ser
225                 230                 235                 240
Asp Pro Asn His Met Gly Gly Phe Asp Phe Leu Leu Ala Asn Asp Val
                245                 250                 255
Asp Leu Ser Asn Pro Val Val Gln Ala Glu Gln Leu Asn Gln Ile His
            260                 265                 270
Tyr Leu Met Asn Trp Gly Ser Ile Val Met Gly Asp Lys Asp Ala Asn
        275                 280                 285
Phe Asp Gly Ile Arg Val Asp Ala Val Asp Asn Val Asp Ala Asp Met
290                 295                 300
Leu Gln Leu Tyr Thr Asn Tyr Phe Arg Glu Tyr Tyr Gly Val Asn Lys
305                 310                 315                 320
Ser Glu Ala Asn Ala Leu Ala His Ile Ser Val Leu Glu Ala Trp Ser
                325                 330                 335
Leu Asn Asp Asn His Tyr Asn Asp Lys Thr Asp Gly Ala Ala Leu Ala
            340                 345                 350
Met Glu Asn Lys Gln Arg Leu Ala Leu Leu Phe Ser Leu Ala Lys Pro
        355                 360                 365
Ile Lys Glu Arg Thr Pro Ala Val Ser Pro Leu Tyr Asn Asn Thr Phe
370                 375                 380
Asn Thr Thr Gln Arg Asp Glu Lys Thr Asp Trp Ile Asn Lys Asp Gly
385                 390                 395                 400
Ser Lys Ala Tyr Asn Glu Asp Gly Thr Val Lys Gln Ser Thr Ile Gly
                405                 410                 415
Lys Tyr Asn Glu Lys Tyr Gly Asp Ala Ser Gly Asn Tyr Val Phe Ile
            420                 425                 430
Arg Ala His Asp Asn Asn Val Gln Asp Ile Ile Ala Glu Ile Ile Lys
        435                 440                 445
Lys Glu Ile Asn Pro Lys Ser Asp Gly Phe Thr Ile Thr Asp Ala Glu
450                 455                 460
Met Lys Gln Ala Phe Glu Ile Tyr Asn Lys Asp Met Leu Ser Ser Asp
465                 470                 475                 480
Lys Lys Tyr Thr Leu Asn Asn Ile Pro Ala Ala Tyr Ala Val Met Leu
                485                 490                 495
Gln Asn Met Glu Thr Ile Thr Arg Val Tyr Tyr Gly Asp Leu Tyr Thr
            500                 505                 510
Asp Asp Gly His Tyr Met Glu Thr Lys Ser Pro Tyr Tyr Asp Thr Ile
        515                 520                 525
Val Asn Leu Met Lys Ser Arg Ile Lys Tyr Val Ser Gly Gly Gln Ala
```

```
                530             535             540
    Gln Arg Ser Tyr Trp Leu Pro Thr Asp Gly Lys Met Asp Asn Ser Asp
    545                 550                 555                 560

Val Glu Leu Tyr Arg Thr Asn Glu Val Tyr Thr Ser Val Arg Tyr Gly
                        565                 570                 575

Lys Asp Ile Met Thr Ala Asn Asp Thr Glu Gly Ser Lys Tyr Ser Arg
                    580                 585                 590

Thr Ser Gly Gln Val Thr Leu Val Ala Asn Asn Pro Lys Leu Asn Leu
                595                 600                 605

Asp Gln Ser Ala Lys Leu Asn Val Glu Met Gly Lys Ile His Ala Asn
        610                 615                 620

Gln Lys Tyr Arg Ala Leu Ile Val Gly Thr Ala Asp Gly Ile Lys Asn
    625                 630                 635                 640

Phe Thr Ser Asp Ala Asp Ala Ile Ala Ala Gly Tyr Val Lys Glu Thr
                        645                 650                 655

Asp Ser Asn Gly Val Leu Thr Phe Gly Ala Asn Asp Ile Lys Gly Tyr
                    660                 665                 670

Glu Thr Phe Asp Met Ser Gly Phe Val Ala Val Trp Val Pro Val Gly
                675                 680                 685

Ala Ser Asp Asn Gln Asp Ile Arg Val Ala Pro Ser Thr Glu Ala Lys
        690                 695                 700

Lys Glu Gly Glu Leu Thr Leu Lys Ala Thr Glu Ala Tyr Asp Ser Gln
    705                 710                 715                 720

Leu Ile Tyr Glu Gly Phe Ser Asn Phe Gln Thr Ile Pro Asp Gly Ser
                        725                 730                 735

Asp Pro Ser Val Tyr Thr Asn Arg Lys Ile Ala Glu Asn Val Asp Leu
                    740                 745                 750

Phe Lys Ser Trp Gly Val Thr Ser Phe Glu Met Ala Pro Gln Phe Val
                755                 760                 765

Ser Ala Asp Asp Gly Thr Phe Leu Asp Ser Val Ile Gln Asn Gly Tyr
        770                 775                 780

Ala Phe Ala Asp Arg Tyr Asp Leu Ala Met Ser Lys Asn Asn Lys Tyr
    785                 790                 795                 800

Gly Ser Lys Glu Asp Leu Arg Asp Ala Leu Lys Ala Leu His Lys Ala
                        805                 810                 815

Gly Ile Gln Ala Ile Ala Asp Trp Val Pro Asp Gln Ile Tyr Gln Leu
                    820                 825                 830

Pro Gly Lys Glu Val Val Thr Ala Thr Arg Thr Asp Gly Ala Gly Arg
                835                 840                 845

Lys Ile Ala Asp Ala Ile Ile Asp His Ser Leu Tyr Val Ala Asn Ser
        850                 855                 860

Lys Ser Ser Gly Lys Asp Tyr Gln Ala Lys Tyr Gly Gly Glu Phe Leu
    865                 870                 875                 880

Ala Glu Leu Lys Ala Lys Tyr Pro Glu Met Phe Lys Val Asn Met Ile
                        885                 890                 895

Ser Thr Gly Lys Pro Ile Asp Asp Ser Val Lys Leu Lys Gln Trp Lys
                    900                 905                 910

Ala Glu Tyr Phe Asn Gly Thr Asn Val Leu Glu Arg Gly Val Gly Tyr
                915                 920                 925

Val Leu Ser Asp Glu Ala Thr Gly Lys Tyr Phe Thr Val Thr Lys Glu
        930                 935                 940

Gly Asn Phe Ile Pro Leu Gln Leu Thr Gly Lys Glu Lys Val Ile Thr
    945                 950                 955                 960
```

-continued

```
Gly Phe Ser Ser Asp Gly Lys Gly Ile Thr Tyr Phe Gly Thr Ser Gly
                965                 970                 975
Thr Gln Ala Lys Ser Ala Phe Val Thr Phe Asn Gly Asn Thr Tyr Tyr
                980                 985                 990
Phe Asp Ala Arg Gly His Met Val Thr Asn Ser Glu Tyr Ser Pro Asn
                995                1000                1005
Gly Lys Asp Val Tyr Arg Phe Leu Pro Asn Gly Ile Met Leu Ser
           1010                1015                1020
Asn Ala Phe Tyr Ile Asp Ala Asn Gly Asn Thr Tyr Leu Tyr Asn
           1025                1030                1035
Ser Lys Gly Gln Met Tyr Lys Gly Gly Tyr Thr Lys Phe Asp Val
           1040                1045                1050
Ser Glu Thr Asp Lys Asp Gly Lys Glu Ser Lys Val Val Lys Phe
           1055                1060                1065
Arg Tyr Phe Thr Asn Glu Gly Val Met Ala Lys Gly Val Thr Val
           1070                1075                1080
Ile Asp Gly Phe Thr Gln Tyr Phe Gly Glu Asp Gly Phe Gln Ala
           1085                1090                1095
Lys Asp Lys Leu Val Thr Phe Lys Gly Lys Thr Tyr Tyr Phe Asp
           1100                1105                1110
Ala His Thr Gly Asn Gly Ile Lys Asp Thr Trp Arg Asn Ile Asn
           1115                1120                1125
Gly Lys Trp Tyr Tyr Phe Asp Ala Asn Gly Val Ala Ala Thr Gly
           1130                1135                1140
Ala Gln Val Ile Asn Gly Gln Lys Leu Tyr Phe Asn Glu Asp Gly
           1145                1150                1155
Ser Gln Val Lys Gly Gly Val Val Lys Asn Ala Asp Gly Thr Tyr
           1160                1165                1170
Ser Lys Tyr Lys Glu Gly Phe Gly Glu Leu Val Thr Asn Glu Phe
           1175                1180                1185
Phe Thr Thr Asp Gly Asn Val Trp Tyr Tyr Ala Gly Ala Asn Gly
           1190                1195                1200
Lys Thr Val Thr Gly Ala Gln Val Ile Asn Gly Gln His Leu Tyr
           1205                1210                1215
Phe Asn Ala Asp Gly Ser Gln Val Lys Gly Gly Val Val Lys Asn
           1220                1225                1230
Ala Asp Gly Thr Tyr Ser Lys Tyr Asn Ala Ser Thr Gly Glu Arg
           1235                1240                1245
Leu Thr Asn Glu Phe Phe Thr Thr Gly Asp Asn Asn Trp Tyr Tyr
           1250                1255                1260
Ile Gly Ala Asn Gly Lys Ser Val Thr Gly Glu Val Lys Ile Gly
           1265                1270                1275
Asp Asp Thr Tyr Phe Phe Ala Lys Asp Gly Lys Gln Val Lys Gly
           1280                1285                1290
Gln Thr Val Ser Ala Gly Asn Gly Arg Ile Ser Tyr Tyr Tyr Gly
           1295                1300                1305
Asp Ser Gly Lys Arg Ala Val Ser Thr Trp Ile Glu Ile Gln Pro
           1310                1315                1320
Gly Val Tyr Val Tyr Phe Asp Lys Asn Gly Leu Ala Tyr Pro Pro
           1325                1330                1335
Arg Val Leu Asn
           1340
```

PROCESS FOR PRODUCING ALPHA-1,3-GLUCAN POLYMER WITH REDUCED MOLECULAR WEIGHT

This application claims the benefit of U.S. Provisional Application No. 61/873,851, filed Sep. 5, 2013, which is incorporated herein by reference in its entirety.

FIELD OF THE INVENTION

This invention is in the field of enzymatic processes. Specifically, this invention pertains to a process for producing alpha-1,3-glucan polymer in a solution comprising glucosyl transferase, sucrose, and a polar organic solvent.

Reference to Sequence Listing Submitted Electronically

The official copy of the sequence listing is submitted electronically via EFS-Web as an ASCII formatted sequence listing with a file named CL5841 USNP_SequenceListing.txt created on Sep. 3, 2014, and having a size of 259 kilobytes and is filed concurrently with the specification. The sequence listing contained in this ASCII-formatted document is part of the specification and is herein incorporated by reference in its entirety.

BACKGROUND OF THE INVENTION

Cellulose, a polysaccharide consisting of beta-1,4-linked glucose formed by natural processes (Applied Fiber Science, F. Happey, Ed., Chapter 8, E. Atkins, Academic Press, New York, 1979), has become the preeminent fiber for use in manufactured textiles, films and resins.

Cellulose and starch exhibit properties that are determined by the nature of their linkage pattern. Starch or amylose consisting of alpha-1,4 linked glucose are not useful for fiber applications because it is swollen or dissolved by water. Cellulose, on the other hand, has a beta-1,4 linkage which provides the crystalline and hydrophobic qualities making cellulose a good structural material. Thus, cellulose is commonly used for textile applications like cotton fiber.

Cellulosic fibers such as cotton and rayon increasingly present sustainability issues with respect to land use and environmental imprint. This may be a significant factor leading to increased level of research into textiles containing polyester fiber blends with cellulosic materials and more sustainable alternatives for cellulosic-derived materials.

Driven by a desire to find new structural polysaccharides using enzymatic syntheses or genetic engineering of microorganisms or plant hosts, researchers have discovered polysaccharides that are biodegradable, and that can be made economically from renewable resource-based feedstocks. One such polysaccharide is poly alpha-1,3-glucan, a glucan polymer characterized by having alpha-1,3-glycosidic linkages. This polymer has been isolated by contacting an aqueous solution of sucrose with a glucosyltransferase enzyme isolated from *Streptococcus salivarius* (Simpson et al., *Microbiology* 141:1451-1460, 1995). Films prepared from poly alpha-1,3-glucan tolerate temperatures up to 150° C. and provide an advantage over polymers obtained from beta-1,4-linked polysaccharides (Ogawa et al., *Fiber Differentiation Methods* 47:353-362, 1980).

U.S. Pat. No. 7,000,000 disclosed the preparation of a polysaccharide fiber comprising hexose units, wherein at least 50% of the hexose units within the polymer were linked via alpha-1,3-glycosidic linkages using an *S. salivarius* gtfJ enzyme. This enzyme utilizes sucrose as a substrate in a polymerization reaction producing poly alpha-1,3-glucan and fructose as end-products (Simpson et al., 1995).

The production of poly alpha-1,3-glucan for commercial applications using sucrose and gtf enzymes requires a high yield process that produces minimal amounts of by-product such as leucrose as well as the ability to control the polymer length or molecule weight of the resulting poly alpha-1,3-glucan.

Castillo et al. (*Journal of Biotechnology* 114:209-217, 2004) disclosed that the inclusion of 2-methyl-2-propanol (tert-butyl alcohol) in a reaction for producing levan resulted in levan having an increased molecular weight profile compared to the molecular weight profile of levan made without using tert-butyl alcohol.

Masanori et al. (Japanese Pat. Appl. Publ. No. P2000-175694A) disclosed that the inclusion of dimethyl sulfoxide in a reaction for producing mutan resulted in the production of mutan with increased molecular weight compared to the molecular weight observed in reactions lacking dimethyl sulfoxide. Thus, increasing the molecular weight of certain polysaccharide polymers is possible under certain reaction conditions.

Alternatively, decreasing the molecular weight of polysaccharide polymers is another means by which to control the molecular weight. Accordingly, processes for producing poly alpha-1,3-glucan having reduced molecular weight are desirable as another approach to producing a polysaccharide polymer of desired molecular weight.

SUMMARY OF THE INVENTION

In one embodiment, the invention concerns a process for producing poly alpha-1,3-glucan comprising contacting water, sucrose, a polar organic solvent, and a glucosyltransferase enzyme in a solution, wherein the glucosyltransferase enzyme synthesizes poly alpha-1,3-glucan. The poly alpha-1,3-glucan thus produced has a reduced molecular weight compared to the molecular weight of a poly alpha-1,3-glucan that would be produced in the absence of the polar organic solvent. Optionally, the process in this embodiment further comprises the step of isolating the poly alpha-1,3-glucan produced in the contacting step.

In a second embodiment, the polar organic solvent is aprotic. The aprotic polar organic solvent can be acetonitrile, dimethyl sulfoxide, acetone, N,N-dimethylformamide, N,N-dimethylacetamide, tetrahydrofuran, propylene carbonate, or sulfolane, for example.

In a third embodiment, the polar organic solvent is protic. The protic polar organic solvent can be methanol, methyl formamide, ethanol, isopropanol, 1-propanol, tert-butyl alcohol, or formamide, for example.

In a fourth embodiment, the concentration of the polar organic solvent in the solution is about 2% to about 20% by volume. In a fifth embodiment, the concentration of the polar organic solvent in the solution is about 10% by volume.

In a sixth embodiment, the solution has a temperature between about 5° C. to about 50° C.

In a seventh embodiment, the initial concentration of the sucrose in the solution is about 20 g/L to about 400 g/L.

In an eighth embodiment, the molecular weight of the poly alpha-1,3-glucan produced in the contacting step is reduced by at least about 15%. In a ninth embodiment, the molecular weight of the poly alpha-1,3-glucan produced in the contacting step is reduced by at least about 50%.

In a tenth embodiment, the molecular weight is measured as weight average degree of polymerization (DPw). In an eleventh embodiment, the DPw of the poly alpha-1,3-glucan produced in the contacting step is between about 40 and 800.

In a twelfth embodiment, the glucosyltransferase enzyme is a bacterial glucosyltransferase enzyme.

In a thirteenth embodiment, the glucosyltransferase enzyme comprises an amino acid sequence that is at least 90% identical to SEQ ID NO:12, SEQ ID NO:2, or SEQ ID NO:32.

BRIEF DESCRIPTION OF THE SEQUENCES

TABLE 1

Summary of Nucleic Acid and Protein SEQ ID Numbers

| Description | Nucleic acid SEQ ID NO. | Protein SEQ ID NO. |
|---|---|---|
| "gtfJ", *Streptococcus salivarius*. DNA codon-optimized for expression in *E. coli*. The first 42 amino acids of the protein are deleted compared to GENBANK Identification No. 47527; a start methionine is included. | 1 | 2 (1477 aa) |
| "0874 gtf", *Streptococcus sobrinus*. DNA codon-optimized for expression in *E. coli*. The first 156 amino acids of the protein are deleted compared to GENBANK Identification No. 450874; a start methionine is included. | 3 | 4 (1435 aa) |
| "2678 gtf", *Streptococcus salivarius* K12. DNA codon-optimized for expression in *E. coli*. The first 188 amino acids of the protein are deleted compared to GENBANK Identification No. 400182678; a start methionine is included. | 5 | 6 (1341 aa) |
| "2919 gtf", *Streptococcus salivarius* PS4. DNA codon-optimized for expression in *E. coli*. The first 92 amino acids of the protein are deleted compared to GENBANK Identification No. 383282919; a start methionine is included. | 7 | 8 (1340 aa) |
| "5926 gtf", *Streptococcus dentirousetti*. DNA codon-optimized for expression in *E. coli*. The first 144 amino acids of the protein are deleted compared to GENBANK Identification No. 167735926; a start methionine is included. | 9 | 10 (1323 aa) |
| "6855 gtf", *Streptococcus salivarius* SK126. DNA codon-optimized for expression in *E. coli*. The first 178 amino acids of the protein are deleted compared to GENBANK Identification No. 228476855; a start methionine is included. | 11 | 12 (1341 aa) |
| "gtfJ-T1", *Streptococcus salivarius*. The first 230 amino acids and the last 384 amino acids of the protein are deleted compared to GENBANK Identification No. 47527; a start methionine is included. | 13 | 14 (905 aa) |
| "5926-T1", *Streptococcus dentirousetti*. The first 199 amino acids and the last 417 amino acids of the protein are deleted compared to GENBANK Identification No. 167735926; a start methionine is included. | 15 | 16 (851 aa) |
| "wild type gtfJ", *Streptococcus salivarius*. GENBANK Identification No. 47527. | 17 | 18 (1518 aa) |
| "2379 gtf", *Streptococcus salivarius*. DNA codon-optimized for expression in *E. coli*. The first 203 amino acids of the protein are deleted compared to GENBANK Identification No. 662379; a start methionine is included. | 19 | 20 (1247 aa) |
| "1724 gtf", *Streptococcus downei*. DNA codon-optimized for expression in *E. coli*. The first 162 amino acids of the protein are deleted compared to GENBANK Identification No. 121724; a start methionine is included. | 21 | 22 (1436 aa) |
| "0544 gtf", *Streptococcus mutans*. DNA codon-optimized for expression in *E. coli*. The first 164 amino acids of the protein are deleted compared to GENBANK Identification No. 290580544; a start methionine is included. | 23 | 24 (1313 aa) |

TABLE 1-continued

Summary of Nucleic Acid and Protein SEQ ID Numbers

| Description | Nucleic acid SEQ ID NO. | Protein SEQ ID NO. |
|---|---|---|
| "4297 gtf", *Streptococcus oralis*. DNA codon-optimized for expression in *E. coli*. The first 228 amino acids of the protein are deleted compared to GENBANK Identification No. 7684297; a start methionine is included. | 25 | 26 (1348 aa) |
| "5618 gtf", *Streptococcus sanguinis*. DNA codon-optimized for expression in *E. coli*. The first 223 amino acids of the protein are deleted compared to GENBANK Identification No. 328945618; a start methionine is included. | 27 | 28 (1348 aa) |
| "2765 gtf", unknown *Streptococcus* sp. C150. DNA codon-optimized for expression in *E. coli*. The first 193 amino acids of the protein are deleted compared to GENBANK Identification No. 322372765; a start methionine is included. | 29 | 30 (1340 aa) |
| *Streptococcus salivarius* gtfJ. The first 177 amino acids of the protein are deleted compared to GENBANK Identification No. 47527; a start methionine is included. | 31 | 32 (1342 aa) |

DETAILED DESCRIPTION OF THE INVENTION

The disclosures of all patent and non-patent literature cited herein are incorporated herein by reference in their entirety.

As used herein, the term "invention" or "disclosed invention" is not meant to be limiting, but applies generally to any of the inventions defined in the claims or described herein. These terms are used interchangeably herein.

The terms "poly alpha-1,3-glucan", "alpha-1,3-glucan polymer" and "glucan polymer" are used interchangeably herein. Poly alpha-1,3-glucan is a polymer comprising glucose monomeric units linked together by glycosidic linkages, wherein at least about 50% of the glycosidic linkages are alpha-1,3-glycosidic linkages. Poly alpha-1,3-glucan is a type of polysaccharide. The structure of poly alpha-1,3-glucan can be illustrated as follows:

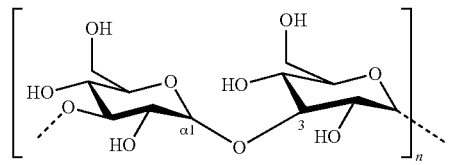

The terms "glycosidic linkage" and "glycosidic bond" are used interchangeably herein and refer to the type of covalent bond that joins a carbohydrate (sugar) molecule to another group such as another carbohydrate. The term "alpha-1,3-glycosidic linkage" as used herein refers to the type of covalent bond that joins alpha-D-glucose molecules to each other through carbons 1 and 3 on adjacent alpha-D-glucose rings. This linkage is illustrated in the poly alpha-1,3-glucan structure provided above. Herein, "alpha-D-glucose" will be referred to as "glucose".

The term "sucrose" herein refers to a non-reducing disaccharide composed of an alpha-D-glucose molecule and a beta-D-fructose molecule linked by an alpha-1,2-glycosidic bond. Sucrose is known commonly as table sugar.

The "molecular weight" of the poly alpha-1,3-glucan herein can be represented by various measures such as grams/ mole, Daltons, DPw ("weight average degree of polymerization") and DPn ("number average degree of polymerization"). Various means are known in the art for calculating these molecular weight measurements.

The terms "glucosyltransferase enzyme that synthesizes poly alpha-1,3-glucan", "glucosyltransferase enzyme", "gtf enzyme", "gtf", and "glucansucrase" are used interchangeably herein. The activity of a gtf enzyme herein catalyzes the reaction of the substrate sucrose to make the products poly alpha-1,3-glucan and fructose. Other products (byproducts) of a gtf reaction can include glucose (where glucose is hydrolyzed from the glucosyl-gtf enzyme intermediate complex), various soluble oligosaccharides (DP2-DP7), and leucrose (where glucose of the glucosyl-gtf enzyme intermediate complex is linked to fructose). Leucrose is a disaccharide composed of glucose and fructose linked by an alpha-1,5 linkage. Wild type forms of glucosyltransferase enzymes generally contain (in the N-terminal to C-terminal direction) a signal peptide, a variable domain, a catalytic domain, and a glucan-binding domain.

The terms "reaction" and "enzymatic reaction" are used interchangeably herein and refer to a reaction that is catalyzed by a glucosyltransferase enzyme. A "reaction solution" as used herein generally refers to a solution comprising at least one active glucosyltransferase enzyme in a buffer solution comprising sucrose, water, and optionally a polar organic solvent. It is in the reaction solution where the step of contacting water, sucrose, a polar organic solvent, and a glucosyltransferase enzyme is performed. The term "under suitable reaction conditions" as used herein, refers to reaction conditions supporting the conversion of sucrose to poly alpha-1,3-glucan using a glucosyltransferase enzyme.

The terms "polar organic solvent" and "water-miscible organic solvent" are used interchangeably herein. A polar organic solvent can be dissolved in water or an aqueous solution. Thus, a polar organic solvent does not separate out into a different phase when added to water or an aqueous solution. A polar organic solvent contains carbon and at least one heteroatom (i.e., non-carbon or—hydrogen atom) such as oxygen, nitrogen, sulfur, or phosphorous. This contrasts with non-polar organic solvents, which generally comprise only carbon and hydrogen atoms. A polar organic solvent typically has a dielectric constant greater than about 4. Polar organic solvents contain dipoles due to polar bonds. In certain embodiments, the polar organic solvent dissolves in water or an aqueous solution at a temperature between about 5° C. to 50° C.

The term "aprotic polar organic solvent" herein refers to a polar organic solvent that does not have suitably labile hydrogen atoms that can form hydrogen bonds. An aprotic polar organic solvent does not contain hydrogen atoms bonded to an atom with electronegative character; e.g., there are no O—H, N—H, or S—H bonds.

The term "protic polar organic solvent" herein refers to a polar organic solvent that has one or more suitably labile hydrogen atoms that can to form hydrogen bonds. A protic polar organic solvent generally contains hydrogen atoms bonded to an atom with electronegative character; e.g., there are O—H, N—H, and/or S—H bonds.

The terms "percent by volume", "volume percent", "vol %" and "v/v %" are used interchangeably herein. The percent by volume of a solute in a solution can be determined using the formula: [(volume of solute)/(volume of solution)]×100%.

The terms "percent by weight", "weight percentage (wt %)" and "weight-weight percentage (% w/w)" are used interchangeably herein. Percent by weight refers to the percentage of a material on a mass basis as it is comprised in a composition, mixture or solution.

The terms "polynucleotide", "polynucleotide sequence", and "nucleic acid sequence" are used interchangeably herein. These terms encompass nucleotide sequences and the like. A polynucleotide may be a polymer of DNA or RNA that is single- or double-stranded, that optionally contains synthetic, non-natural or altered nucleotide bases. A polynucleotide may be comprised of one or more segments of cDNA, genomic DNA, synthetic DNA, or mixtures thereof.

The term "gene" as used herein refers to a polynucleotide sequence that expresses a protein, and which may refer to the coding region alone or may include regulatory sequences upstream and/or downstream to the coding region (e.g., 5' untranslated regions upstream of the transcription start site of the coding region). A gene that is "native" or "endogenous" refers to a gene as found in nature with its own regulatory sequences; this gene is located in its natural location in the genome of an organism. "Chimeric gene" refers to any gene that is not a native gene, comprising regulatory and coding sequences that are not found together in nature. A "foreign" or "heterologous" gene refers to a gene that is introduced into the host organism by gene transfer. Foreign genes can comprise native genes inserted into a non-native organism, native genes introduced into a new location within the native host, or chimeric genes. The polynucleotide sequences in certain embodiments disclosed herein are heterologous. A "transgene" is a gene that has been introduced into the genome by a transformation procedure. A "codon-optimized gene" is a gene having its frequency of codon usage designed to mimic the frequency of preferred codon usage of the host cell.

A native amino acid sequence or polynucleotide sequence is naturally occurring, whereas a non-native amino acid sequence or polynucleotide sequence does not occur in nature.

"Coding sequence" as used herein refers to a DNA sequence that codes for a specific amino acid sequence. "Regulatory sequences" as used herein refer to nucleotide sequences located upstream of the coding sequence's transcription start site, 5' untranslated regions and 3' non-coding regions, and which may influence the transcription, RNA processing or stability, or translation of the associated coding sequence. Regulatory sequences may include promoters, enhancers, silencers, 5' untranslated leader sequence, introns, polyadenylation recognition sequences, RNA processing sites, effector binding sites, stem-loop structures and other elements involved in regulation of gene expression.

The term "recombinant" as used herein refers to an artificial combination of two otherwise separated segments of sequence, e.g., by chemical synthesis or by the manipulation of isolated segments of nucleic acids by genetic engineering techniques. The terms "recombinant", "transgenic", "transformed", "engineered" or "modified for exogenous gene expression" are used interchangeably herein.

The term "transformation" as used in certain embodiments refers to the transfer of a nucleic acid molecule into a host organism. The nucleic acid molecule may be a plasmid that replicates autonomously, or it may integrate into the genome of the host organism. Host organisms containing the transformed nucleic acid fragments are referred to as "transgenic" or "recombinant" or "transformed" organisms or "transformants".

The term "recombinant" or "heterologous" refers to an artificial combination of two otherwise separated segments of sequence, e.g., by chemical synthesis or by the manipulation of isolated segments of nucleic acids by genetic engineering techniques.

The terms "sequence identity" or "identity" as used herein with respect to polynucleotide or polypeptide sequences refer to the nucleic acid bases or amino acid residues in two sequences that are the same when aligned for maximum correspondence over a specified comparison window. Thus, "percentage of sequence identity" or "percent identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity.

The Basic Local Alignment Search Tool (BLAST) algorithm, which is available online at the National Center for Biotechnology Information (NCBI) website, may be used, for example, to measure percent identity between or among two or more of the polynucleotide sequences (BLASTN algorithm) or polypeptide sequences (BLASTP algorithm) disclosed herein. Alternatively, percent identity between sequences may be performed using a Clustal algorithm (e.g., ClustalW or ClustalV). For multiple alignments using a Clustal method of alignment, the default values may correspond to GAP PENALTY=10 and GAP LENGTH PENALTY=10. Default parameters for pairwise alignments and calculation of percent identity of protein sequences using a Clustal method may be KTUPLE=1, GAP PENALTY=3, WINDOW=5 and DIAGONALS SAVED=5. For nucleic acids, these parameters may be KTUPLE=2, GAP PENALTY=5, WINDOW=4 and DIAGONALS SAVED=4.

Various polypeptide amino acid sequences and polynucleotide sequences are disclosed herein as features of certain embodiments of the disclosed invention. Variants of these sequences that are at least about 70-85%, 85-90%, or 90%-95% identical to the sequences disclosed herein may be used in certain embodiments. Alternatively, a variant amino acid sequence or polynucleotide sequence in certain embodiments can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 85%, 86%, 87%, 88%, 89%, 90%, 91%, 92%, 93%, 94%, 95%, 96%, 97%, 98%, or 99% of the function/activity of the disclosed sequence.

The term "isolated" as used in certain embodiments refers to any cellular component that has been completely or partially purified from its native source (e.g., an isolated polynucleotide or polypeptide molecule). In some instances, an isolated polynucleotide or polypeptide molecule is part of a greater composition, buffer system or reagent mix. For example, the isolated polynucleotide or polypeptide molecule can be comprised within a cell or organism in a heterologous manner. Another example is an isolated glucosyltransferase enzyme.

Embodiments of the disclosed invention concern a process for producing poly alpha-1,3-glucan that comprises contacting water, sucrose, a polar organic solvent, and a glucosyltransferase enzyme that synthesizes poly alpha-1,3-glucan in solution, wherein a poly alpha-1,3-glucan is produced that has a reduced molecular weight compared to the molecular weight of a poly alpha-1,3-glucan that would be produced in the absence of the polar organic solvent. The poly alpha-1,3-glucan produced by the reaction solution can optionally be isolated. Significantly, this process avoids the complexities of introducing enzyme and/or temperature modifications in trying to reduce the molecular weight of poly alpha-1,3-glucan produced by reactions catalyzed by glucosyltransferase enzyme.

This process can alternatively be characterized as synthesizing poly alpha-1,3 glucan from a reaction solution comprising water, sucrose, a polar organic solvent, and a glucosyltransferase enzyme, whereby poly alpha-1,3-glucan is produced that has a reduced molecular weight compared to poly alpha-1,3-glucan that would be produced if the polar organic solvent is not present in the reaction solution.

One of ordinary skill in the art would appreciate that a reaction solution in which there is no added polar organic solvent (pure aqueous) can be a control reaction with respect to the process of the invention disclosed herein. The control reaction in certain embodiments can have comparable features except for the presence of a polar organic solvent (i.e., the only variable is the presence of a polar organic solvent).

The molecular weight of poly alpha-1,3-glucan made by the process of the invention is reduced by at least about 15% in certain embodiments. In other embodiments, the molecular weight of the poly alpha-1,3-glucan produced by the process of the invention is reduced by at least about 50%. Alternatively, the molecular weight of the poly alpha-1,3-glucan produced in the process can be reduced by at least about 5%, 10%, 15%, 20%, 25%, 30%, 35%, 40%, 45%, 50%, 55%, 60%, 65%, or 70% (or any integer between 5% and 70%). The reduced molecular weight can be expressed in terms of the DPw of the produced poly alpha-1,3-glucan. The process of the invention does not produce poly alpha-1,3-glucan having an increased molecular weight, when expressed in terms of DPw for example.

The molecular weight of the poly alpha-1,3-glucan produced by the instant process can be measured as DPw (weight average degree of polymerization). Alternatively, the molecular weight of the poly alpha-1,3-glucan produced by the instant process can be measured in terms of Daltons, grams/mole, or as DPn (number average degree of polymerization). The molecular weight of poly alpha-1,3-glucan produced by the instant process can be measured in DPw and is between about 40 and 800, for example. The DPw of the poly alpha-1,3-glucan produced in the process can alternatively be between about 100-200, 100-300, 100-400, 100-500, 100-600, 100-700, 100-800, 200-300, 200-400, 200-500, 200-600, 200-700, 200-800, 300-400, 300-500, 300-600, 300-700, 300-800, 400-500, 400-600, 400-700, 400-800, 500-600, 500-700, 500-800, 600-700, 600-800, or 700-800.

The poly alpha-1,3-glucan produced by the process of the instant invention is preferably linear/unbranched. The percentage of glycosidic linkages between the glucose monomer units of the poly alpha-1,3-glucan that are alpha-1,3 is at least about 50%, 60%, 70%, 80%, 90%, 95%, 96%, 97%, 98%, 99%, or 100%. In such embodiments, accordingly, the poly alpha-1,3-glucan has less than about 50%, 40%, 30%, 20%, 10%, 5%, 4%, 3%, 2%, 1%, or 0% (or any integer between 0% and 50%) of glycosidic linkages that are not alpha-1,3. Examples of such non-alpha-1,3 glycosidic linkages include, but are not limited to, beta linkages (e.g., beta-1,2; beta-1,3; beta-1,4; beta-1,6) and other alpha linkages (e.g., alpha-1,2; alpha-1,4; alpha-1,6).

It is understood that the higher the percentage of alpha-1,3-glycosidic linkages present in the poly alpha-1,3-glucan, the greater the probability that the poly alpha-1,3-glucan is linear, since there are lower occurrences of certain glycosidic linkages forming branch points in the polymer. In certain embodiments, the poly alpha-1,3-glucan has no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

The glycosidic linkage profile of the poly alpha-1,3-glucan can be determined using any method known in the art. For example, the linkage profile can be determined using methods that use nuclear magnetic resonance (NMR) spectroscopy (e.g., $^{13}$C NMR or $^1$H NMR). These and other methods that can be used are disclosed in *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, Fla., 2005), which is incorporated herein by reference.

The poly alpha-1,3-glucan produced in the disclosed process can be either soluble or insoluble in most aqueous systems, where insoluble polymer is preferred. In general, the solubility of a glucan polymer in most aqueous systems is related to its linkage type, molecular weight and/or degree of branching. Poly alpha-1,3-glucan is generally insoluble at a DPw of 8 and above in aqueous (or mostly aqueous) solutions at 20° C.

The molecular weight of the poly alpha-1,3-glucan produced by the process of the present invention can be measured using any of several means known in the art. For example, glucan polymer molecular weight can be measured using high-pressure liquid chromatography (HPLC), size exclusion chromatography (SEC), or gel permeation chromatography (GPC).

The yield of the poly alpha-1,3-glucan produced in the disclosed process can be at least about 5%, 6%, 7%, 8%, 9%, 10%, 11%, 12%, 13%, 14%, 15%, 16%, 17%, 18%, 19%, or 20%, based on the weight of the sucrose used in the process.

The process of the invention comprises contacting a glucosyltransferase enzyme capable of synthesizing poly alpha-1,3-glucan with water, sucrose and a polar organic solvent in a solution. The glucosyltransferase enzyme used herein catalyzes the conversion of sucrose to poly alpha-1,3-glucan. An example of such a glucosyltransferase enzyme is wild type gtfJ expressed by *Streptococcus salivarius* (GENBANK Identification No. 47527, SEQ ID NO:18; Simpson et al., *Microbiology* 141:1451-1460, 1995). U.S. Pat. No. 7,000,000 (incorporated herein by reference) discloses using a particular gtfJ derived from *S. salivarius* to produce a poly alpha-1,3-glucan that is suitable for use as a spinnable fiber.

Any glucosyltransferase enzyme may be used in the process of the invention disclosed herein. Preferably, the enzyme is fungal or bacterial. Such an enzyme may be derived from a *Streptococcus* species, *Leuconostoc* species or *Lactobacillus* species, for example. Examples of *Streptococcus* species from which the glucosyltransferase may be derived include *S. salivarius, S. sobrinus, S. dentirousetti, S. downei, S. mutans, S. oralis* and *S. sanguinis*. Examples of *Leuconostoc* species from which the glucosyltransferase may be derived include *L. mesenteroides, L. amelibiosum, L. argentinum, L. carnosum, L. citreum, L. cremoris, L. dextranicum* and *L. fructosum*. Examples of *Lactobacillus* species from which the glucosyl-transferase may be derived include *L. acidophilus, L. delbrueckii, L. helveticus, L. salivarius, L. casei, L. curvatus, L. plantarum, L. sakei, L. brevis, L. buchneri, L. fermentum* and *L. reuteri*.

The glucosyltransferase enzyme used in certain embodiments of the invention comprises, or consists of, the amino acid sequence provided in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32. Alternatively, the glucosyltransferase enzyme comprises, or consists of, an amino acid that is at least 90%, 91%, 92%, 93%, 94%, 95%, 96%, 97%, 98%, or 99% identical to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, or SEQ ID NO:32, wherein the glucosyltransferase enzyme has activity. The glucosyltransferase enzyme used in certain embodiments comprises an amino acid sequence that is at least 90% identical to the sequence set forth in SEQ ID NO:12, SEQ ID NO:2, or SEQ ID NO:32. In still another aspect, a glucosyltransferase enzyme may be any of the above-identified amino acid sequences and further include 1-300 (or any integer there between) residues on the N-terminus and/or the C-terminus and still retain activity. Such additional residues may be from a corresponding wild type sequence from which the glucosyltransferase enzyme is derived, or may be another sequence such as an epitope tag (at either N- or C-terminus) or a heterologous signal peptide (at N-terminus), for example.

In another aspect a glucosyltransferase enzyme could be a variant enzyme, i.e., one that is non-naturally occurring but retains activity. For example, it could be modified through a truncation or a deletion. Such a variant enzyme may lack a number of amino acids at the N- and/or C-terminus (truncation or internal deletion) compared to the wild type sequence from which the variant enzyme was derived. For example, a glucosyltransferase enzyme used herein may lack amino acids in the signal peptide and/or variable domain that are otherwise present in the corresponding wild type form of the enzyme. This is an example of an enzyme with an N-terminal truncation or internal deletion. As another example, a glucosyltransferase enzyme used in the instant process may lack amino acids in the glucan-binding domain. This is an example of an enzyme with a C-terminal truncation or internal deletion. Other examples of enzymes that can be used are those having both N- and C-terminal truncations or deletions. All the various modified glucosyltransferase enzymes disclosed herein, such as the above-described truncated and internally deleted variants, have glucosyltransferase activity.

The glucosyltransferase enzyme in certain embodiments is encoded by the polynucleotide sequence provided in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31. Alternatively, the glucosyltransferase enzyme is encoded by a polynucleotide sequence that is at least 90%, 91%, 92%, 93%, 94%, 95%, 96%, 97%, 98%, or 99% identical to SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:29, or SEQ ID NO:31.

The glucosyltransferase enzyme in certain embodiments synthesizes poly alpha-1,3-glucan in which at least about 50%, 60%, 70%, 80%, 90%, 95%, 96%, 97%, 98%, 99%, or 100% (or any integer between 50% and 100%) of the constituent glycosidic linkages are alpha-1,3 linkages. In such embodiments, accordingly, the glucosyltransferase enzyme synthesizes poly alpha-1,3-glucan in which there is less than about 50%, 40%, 30%, 20%, 10%, 5%, 4%, 3%, 2%, or 1% of glycosidic linkages that are not alpha-1,3. Examples of such non-alpha-1,3 glycosidic linkages include beta linkages (e.g., beta-1,2; beta-1,3; beta-1,4; beta-1,6) and other alpha linkages (e.g., alpha-1,2; alpha-1,4; alpha-1,6).

In other aspects, the glucosyltransferase enzyme synthesizes poly alpha-1,3-glucan with no branch points or less than about 10%, 9%, 8%, 7%, 6%, 5%, 4%, 3%, 2%, or 1% branch points as a percent of the glycosidic linkages in the polymer. Examples of branch points include alpha-1,6 branch points, such as those that are present in mutan polymer.

One or more different glucosyltransferase enzymes may be used in the solution in which the enzyme is contacted with water, sucrose and a polar organic solvent. The glucosyltransferase enzyme in certain embodiments does not have, or has very little (less than 1%), dextransucrase, reuteransucrase, or alternansucrase activity. The glucosyltransferase enzyme in certain embodiments does not produce, or produces very few (less than 1% or 2%), glycosidic linkages that are not alpha-1,3 glycosidic linkages. Nor is the glucosyltransferase a wild type enzyme derived from *S. mutans* in certain embodiments.

The glucosyltransferase enzyme used in the instant process can be primer-independent or primer-dependent. A primer-dependent glucosyltransferase enzyme requires the presence of an initiating molecule in the reaction solution to act as a primer for the enzyme during glucan polymer synthesis. The term "primer" as used herein refers to any molecule that can act as the initiator for a glucosyltransferase enzyme. Primer-independent glucosyltransferase enzymes do not require the presence of a primer to perform glucan synthesis. Primers that can be used in certain embodiments include dextran and other carbohydrate-based primers, such as hydrolyzed glucan.

The glucosyltransferase enzyme used herein may be produced by any means known in the art (e.g., U.S. Pat. No. 7,000,000, which is incorporated herein by reference). For example, the glucosyltransferase enzyme may be produced recombinantly in any bacterial (e.g., *E. coli* such as TOP10, *Bacillus* sp.) or eukaryotic (e.g., yeasts such as *Pichia* sp. and *Saccharomyces* sp.) heterologous gene expression system. One of the above-listed nucleic acid sequences can be used for this purpose, for example. Alternatively, the glucosyltransferase enzyme may be obtained from a species that naturally produces a glucosyltransferase enzyme.

The glucosyltransferase enzyme used herein may be purified and/or isolated prior to its use, or may be used in the form of a cell lysate, for example. A cell lysate or extract may be prepared from a bacteria (e.g., *E. coli*) used to heterologously express the enzyme. For example, the bacteria may be subjected to disruption using a French pressure cell (French press). The glucosyltransferase enzyme is soluble in these type of preparations. The lysate or extract may be used at about 0.15-0.3% (v/v) in a reaction solution for producing poly alpha-1,3-glucan from sucrose. In certain embodiments, a bacterial cell lysate is first cleared of insoluble material by means such as centrifugation or filtration.

In certain embodiments, the heterologous gene expression system may be one that is designed for protein secretion. The glucosyltransferase enzyme comprises a signal peptide (signal sequence) in such embodiments. The signal peptide may be either its native signal peptide or a heterologous signal peptide.

The activity of the glucosyltransferase enzyme can be determined using any method known in the art. For example, glucosyltransferase enzyme activity can be determined by measuring the production of reducing sugars (fructose and glucose) in a reaction solution containing sucrose (50 mg/mL), dextran T-10 (1 mg/mL) and potassium phosphate buffer (pH 6.5, 50 mM), where the solution is held at 22-25° C. for 24-30 hours. The reducing sugars can be measured by adding 0.01 mL of the reaction solution to a mixture containing 1 N NaOH and 0.1% triphenyltetrazolium chloride and then monitoring the increase in absorbance at $OD_{480\,nm}$ for five minutes.

A polar organic solvent is used in the disclosed process. The polar organic solvent can be aprotic. Examples of aprotic polar organic solvents that can be used include, but are not limited to, acetonitrile, dimethyl sulfoxide, acetone, N,N-dimethylformamide, N,N-dimethylacetamide, tetrahydrofuran, propylene carbonate, and sulfolane. Other non-limiting examples of aprotic polar organic solvents that can be used include hexamethylphosphoramide, dimethylimidazolidinone (1,3-dimethyl-2-imidazolidinone), dioxane, nitromethane, and butanone. In general, ester, ketone and aldehyde solvents having no acidic hydrogen atom are other examples of aprotic polar organic solvents that can be used. Acetonitrile can be used as a preferred polar organic solvent.

The polar organic solvent can be protic. Examples of protic polar organic solvents that can be used include, but are not limited to, methanol, methyl formamide, ethanol, isopropanol, 1-propanol, tert-butyl alcohol, and formamide. Other non-limiting examples of protic polar organic solvents that can be used include n-butanol, ethylene glycol, 2-methoxyethanol, 1-methoxy-2-propanol, glycerol, 1,2-propanediol and 1,3-propanetriol. In general, alcohols are other examples of protic polar organic solvents that can be used.

One or more polar organic solvents, such as any of those listed above, may be used in performing the disclosed process. In certain embodiments, the concentration of the polar organic solvent in the solution is about 2% to about 20% by volume. The concentration of the polar organic solvent in the solution is about 10% by volume in certain embodiments. Alternatively, the concentration of the polar organic solvent in the solution can be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25% by volume. Where two or more polar organic solvents are used, their total concentration may be any of the above volume percent measurements.

The temperature of the reaction solution in which the water, sucrose, polar organic solvent and glucosyltransferase enzyme are contacted can be controlled, if desired. In certain embodiments, the solution has a temperature between about 5° C. to about 50° C. The temperature of the solution in certain other embodiments is between about 20° C. to about 40° C. Alternatively, the temperature of the solution may be about 20, 21, 22, 23, 24, 25, 26, 27, 28, 29, 30, 31, 32, 33, 34, 35, 36, 37, 38, 39, or 40° C.

The temperature of the reaction solution may be maintained using various means known in the art. For example, the temperature of reaction solution can be maintained by placing the vessel containing the reaction solution in an air or water bath incubator set at the desired temperature.

The initial concentration of the sucrose in the solution can be about 20 g/L to about 400 g/L, for example. Alternatively, the initial concentration of the sucrose can be about 75 g/L to about 175 g/L. Alternatively still, the initial concentration of the sucrose can be about 80, 85, 90, 95, 100, 105, 110, 115, 120, 125, 130, 135, 140, 145, 150, 155, or 160 g/L. The "initial concentration of sucrose" refers to the sucrose concentration in the solution after all the reaction solution components have been added (water, sucrose, gtf enzyme).

Sucrose used in the reaction solution can be highly pure (≥99.5%) or be of any other purity or grade. For example, the sucrose can have a purity of at least 99.0%, or be reagent grade sucrose. The sucrose may be derived from any renewable sugar source such as sugar cane, sugar beets, cassava, sweet sorghum, or corn. The sucrose can be provided in any form such as crystalline form or non-crystalline form (e.g., syrup or cane juice).

The pH of the solution in which the water, sucrose, polar organic solvent and glucosyltransferase are contacted can be between about 4.0 to about 8.0 in certain embodiments. Alternatively, the pH can be about 4.0, 4.5, 5.0, 5.5, 6.0, 6.5, 7.0, 7.5, or 8.0. In certain embodiments, the pH of a solution containing the water, sucrose and polar organic solvent may be set before adding the glucosyltransferase enzyme. The pH of the reaction solution can be adjusted or controlled by the addition or incorporation of a suitable buffer, including but not limited to: phosphate, tris, citrate, or a combination thereof. The concentration of the buffer can be from 0 mM to about 100 mM, for example. In certain embodiments, the buffer concentration is about 10, 20, or 50 mM. A suitable amount of DTT (e.g., about 1.0 mM) may also be added to the reaction solution in certain embodiments.

Water, sucrose, a polar organic solvent and a glucosyltransferase enzyme are contacted in a reaction solution. It will be understood that, as the glucosyltransferase enzyme synthesizes poly alpha-1,3-glucan, the reaction solution becomes a reaction mixture given that insoluble poly alpha-1,3-glucan falls out of solution as indicated by clouding of the reaction. The contacting step of the disclosed process can be performed in any number of ways. For example, the desired amounts of sucrose and polar organic solvent can first be dissolved in water (optionally, other components may also be added at this stage of preparation, such as buffer components), followed by the addition of the glucosyltransferase enzyme. The solution may be kept still, or agitated via stirring or orbital shaking, for example. The reaction can be, and typically is, a cell-free.

The glucosyltransferase enzyme can be added to water or an aqueous solution (e.g., sucrose in water; sucrose and polar organic solvent in water) that does not contain salt or buffer when initially preparing the reaction solution. The pH of such a preparation can then be modified as desired, such as to pH 5-6 for example. The reaction can be carried out to completion without any added buffer, if desired.

Completion of the reaction in certain embodiments can be determined visually (no more accumulation of precipitated poly alpha-1,3-glucan) and/or by measuring the amount of sucrose left in the solution (residual sucrose), where a percent sucrose consumption of over about 90% can indicate reaction completion. Typically, a reaction of the disclosed process will take about 12, 24, 36, 48, 60, 72, 84, or 96 hours to complete, depending on certain parameters such as the amount of sucrose and glucosyltransferase enzyme used in the reaction.

The percent sucrose consumption of a reaction in certain embodiments of the disclosed process is at least 90%, 91%, 92%, 93%, 94%, 95%, 96%, 97%, 98%, 99%, or 100%. Alternatively, the percent sucrose consumption may be >90% or >95%.

In certain embodiments of the disclosed process, the polar organic solvent does not significantly reduce the activity of the glucosyltransferase enzyme in terms of the percent sucrose consumed during the reaction. This is the case, for example, in reactions where the percent sucrose consumed at the completion of the reaction is at least 90% or 95%.

The inclusion of a polar organic solvent in the disclosed process results in reducing the molecular weight of the poly alpha-1,3-glucan produced by a glucosyltransferase enzyme. Another way to reduce the molecular weight in certain embodiments is to increase the reaction temperature. In certain embodiments of the disclosed process, the polar organic solvent enhances such temperature-dependent reduction in poly alpha-1,3-glucan molecular weight. Such enhancement can be at least about 5%, 10%, 15%, 20%, 25%, 30%, 35%, or 40% (or any integer between 5% and 40%) more reduction of molecular weight of poly alpha-1,3-glucan produced in the process containing a polar organic solvent compared to that produced in a corresponding or control process lacking the polar organic solvent. Any of the glucosyltransferase enzymes and polar organic solvents disclosed herein may be used in this aspect of the disclosed process. For example, gtfJ (SEQ ID NO:2) and acetonitrile (e.g., 10 vol %) may be used. The increase in temperature can be by about 2, 3, 4, 5, 6, 7, 8, 9, 10, 11, 12, 13, or 14° C. in certain embodiments (e.g., from 25° C. to 37° C.).

The poly alpha-1,3-glucan produced in the disclosed process may optionally be isolated. For example, insoluble poly alpha-1,3-glucan may be separated by centrifugation or filtration. In doing so, the poly alpha-1,3-glucan is separated from the rest of the reaction solution, which may comprise water, fructose and certain byproducts (e.g., leucrose, soluble oligosaccharides DP2-DP7). This solution may also comprise residual sucrose and glucose monomer.

Poly alpha-1,3 glucan is a potentially low cost polymer which can be enzymatically produced from renewable resources containing sucrose using glucosyltransferase enzymes. It has been shown that this polymer can form ordered liquid crystalline solutions when the polymer is dissolved in a solvent under certain conditions (U.S. Pat. No. 7,000,000). Such solutions can be spun into continuous, high strength, cotton-like fibers. The poly alpha-1,3 glucan produced using the instant process has comparable utilities. In addition, the poly alpha-1,3 glucan produced herein can be derivatized as described in U.S. Pat. Appl. Publ. Nos. 2014/0179913 and 2014/0187767, which are both incorporated herein by reference.

EXAMPLES

The disclosed invention is further defined in the following Examples. It should be understood that these Examples, while indicating certain preferred aspects of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

Abbreviations

The meaning of some of the abbreviations used herein is as follows: "g" means gram(s), "h" means hour(s), "mL" means milliliter(s), "psi" means pound(s) per square inch, "wt %" means weight percentage, "µm" means micrometer(s), "%" means percent, "° C." means degrees Celsius, "mg" means milligram(s), "mm" means millimeter(s), "mL/min" means milliliters per minute, "m" means meter(s), "µL" means microliter(s), "mmol" means millimole(s), "min" means minute(s), "mol %" means mole percent, "M" means molar, "mg/g" means milligram per gram, "rpm" means revolutions per minute, "MPa" means megaPascals.

General Methods

All reagents were obtained from Sigma-Aldrich (St. Louis, Mo.) unless stated otherwise. N,N-Dimethylacetamide was obtained from J. T. Baker (Phillipsburg, N.J.). Sucrose was obtained from VWR (Radnor, Pa.).

Preparation of Crude Extracts of Glucosyltransferase (gtf) Enzymes

The *Streptococcus salivarius* gtfJ enzyme (SEQ ID NO:2) used in Examples 1 and 2 was expressed in *E. coli* strain DH10B using an isopropyl beta-D-1-thiogalactopyranoside (IPTG)-induced expression system. SEQ ID NO:2 has an N-terminal 42-residue deletion compared to the *S. salivarius* gtfJ amino acid sequence in GENBANK Identification No. 47527. Briefly, *E. coli* DH10B cells were transformed to express SEQ ID NO:2 from a DNA sequence (SEQ ID NO:1) codon-optimized to express the gtfJ enzyme in *E. coli*. This DNA sequence was contained in the expression vector, pJexpress404® (DNA 2.0, Menlo Park Calif.). The transformed cells were inoculated to an initial optical density (OD at $600_{nm}$) of 0.025 in LB medium (10 g/L Tryptone; 5 g/L yeast extract, 10 g/L NaCl) and allowed to grow at 37° C. in an incubator while shaking at 250 rpm. The cultures were induced by addition of 1 mM IPTG when they reached an $OD_{600}$ of 0.8-1.0. Induced cultures were left on the shaker and harvested 3 hours post induction.

GtfJ enzyme (SEQ ID NO:2) was harvested by centrifuging cultured cells (25° C., 16,000 rpm) in an Eppendorf® centrifuge, re-suspending the cells in 5.0 mM phosphate buffer (pH 7.0) and cooling to 4° C. on ice. The cells were broken using a bead beater with 0.1-mm silica beads, and then centrifuged at 16,000 rpm at 4° C. to pellet the unbroken cells and cell debris. The crude extract (containing soluble gtfJ enzyme, SEQ ID NO:2) was separated from the pellet and analyzed by Bradford protein assay to determine protein concentration (mg/mL).

The gtf enzymes used in Example 3 were prepared as follows. *E. coli* TOP10° cells (Invitrogen, Carlsbad Calif.) were transformed with a pJexpress404®-based construct containing a particular gtf-encoding DNA sequence. Each sequence was codon-optimized to express the gtf enzyme in *E. coli*. Individual *E. coli* strains expressing a particular gtf enzyme were grown in LB medium with ampicillin (100 μg/mL) at 37° C. with shaking to $OD_{600}$=0.4-0.5, at which time IPTG was added to a final concentration of 0.5 mM. The cultures were incubated for 2-4 hours at 37° C. following IPTG induction. Cells were harvested by centrifugation at 5,000×g for 15 minutes and resuspended (20% w/v) in 50 mM phosphate buffer pH 7.0 supplemented with dithiothreitol (DTT, 1.0 mM). Resuspended cells were passed through a French Pressure Cell (SLM Instruments, Rochester, N.Y.) twice to ensure >95% cell lysis. Lysed cells were centrifuged for 30 minutes at 12,000×g at 4° C. The resulting supernatant was analyzed by the BCA protein assay and SDS-PAGE to confirm expression of the gtf enzyme, and the supernatant was stored at −20° C.

Analysis of Reaction Profiles

Periodic samples from reactions were taken and analyzed using an Agilent® 1260 HPLC equipped with a refractive index detector. An Aminex® HP-87C column (BioRad, Hercules, Calif.) having deionized water at a flow rate of 0.6 mL/min and 85° C. was used to quantitate the level of sucrose, glucose, leucrose and fructose in the reaction mixtures. An Aminex® HP-42A column (BioRad) having deionized water at a flow rate of 0.6 mL/min and 85° C. was used to quantitate soluble oligosaccharide byproducts (DP2-DP7).

Analysis of Glucan Molecular Weight

Insoluble glucan polymer isolated from reaction mixtures was treated with N,N-dimethylacetamide (DMAc) with 5% lithium chloride (LiCl) at 100° C. for 16 hours to form a glucan polymer solution. This solution (100 μL) was then injected into an Alliance™ 2695 HPLC (Waters Corporation, Milford, Mass.) equipped with a differential refractometer detector operating at 50° C. The mobile phase (DMAc containing 0.11 wt % LiCl) passed at a flow rate of 0.5 mL/min through four styrene-divinyl benzene columns in series; specifically, one KD-802, one KD-801, and two linear KD-806M columns (Shodex, Japan). The polymer molecular weight distribution of the glucan polymer sample was determined by comparison of retention time to a broad glucan standard.

Example 1

Glucan Polymerization Reactions Using gtfJ Enzyme and Polar Organic Solvents

This Example describes producing alpha-1,3-glucan in gtf-catalyzed reactions containing polar organic solvent. Specifically, this example shows that including a polar organic solvent (10 vol %) in a gtf reaction solution reduces the molecular weight of alpha-1,3-glucan synthesized by the reaction. The gtf in this Example was the *S. salivarius* gtfJ enzyme (SEQ ID NO:2).

The desired amount of sucrose was weighed out and diluted up to 90 mL using deionized water. 10 mL of either a polar organic solvent (see Table 2) or water (control) was then added to bring the total volume to 100 mL. The polar organic solvent used was methanol, methyl formamide, ethanol, DMSO, i-propanol, t-butanol, n-propanol, acetone, formamide, acetonitrile, N,N-dimethylformamide, N,N-dimethylacetamide, tetrahydrofuran, propylene carbonate, or sulfolane. Each solution was next transferred to a 125-mL glass bottle equipped with a polypropylene cap. Fermasure™ was then added (0.5 mL/L reaction, which is 500 ppm), and the pH was adjusted to 5.5 using 5 wt % aqueous sodium hydroxide or 5 wt % aqueous sulfuric acid. The glucan polymerization reaction was initiated by adding 0.3 vol % of crude gtf enzyme (SEQ ID NO:2) extract prepared as described in the General Methods section. This extract contained about 2.9 mg/mL of protein. Agitation to the reaction solution was provided using an Innova® 42 incubator shaker controlled at 25° C. The reaction solution was periodically monitored by HPLC as described in the General Methods section.

After the reaction was determined to be complete by either complete consumption of sucrose or no change in sucrose concentration between measurements, the reaction slurry was filtered. The insoluble alpha-1,3-glucan polymer was then washed with water (200 mL) and acetone (50 mL) and dried at 105° C. using a heated balance (Mettler Toledo® HG63) until no mass change was observed.

The polymer molecular weight was measured according to the General Methods and is presented as the degree of polymerization based on weight (DPw, also referred to as "weight average degree of polymerization"), which can be calculated as the average polymer molecular weight divided by the monomer molecular weight. The results of the polymerization reactions are provided in Table 2. In all cases, a lower polymer molecular weight was observed for reactions in which a polar organic solvent was included, as compared to the molecular weight of the polymer produced by the pure aqueous reaction.

TABLE 2

Molecular Weight of alpha-1,3-Glucan Polymer Produced in Reaction Solutions Containing 10 Vol % Organic Solvent

| Solvent | DPw | Initial sucrose (g/L) | % Sucrose consumption after 24 hr | Final % Sucrose consumption | Reaction time (hr) |
|---|---|---|---|---|---|
| Water only | 714 | 100 | 96 | 96 | 24 |
| Methanol | 594 | 98 | 94 | 94 | 96 |
| Methyl formamide | 519 | 111 | 39 | 40 | 48 |
| Ethanol | 518 | 98 | 93 | 95 | 96 |
| DMSO | 462 | 98 | ND[a] | 95 | 65 |
| i-propanol | 431 | 98 | 82 | 96 | 43 |
| t-butanol | 424 | 109 | 95 | 96 | 96 |
| n-propanol | 374 | 98 | 86 | 95 | 96 |
| Acetone | 358 | 99 | 72 | 96 | 44 |
| Formamide | 329 | 103 | 63 | 97 | 67 |
| Acetonitrile | 321 | 100 | >95 | >95 | 28 |
| N,N-dimethylformamide | 313 | 102 | 82 | 95 | 88 |
| N,N-dimethylacetamide | 304 | 99 | 71 | 92 | 44 |
| Tetrahydrofuran | 286 | 101 | 72 | 96 | 44 |
| Propylene carbonate | 260 | 99 | 57 | 90 | 88 |
| Sulfolane | 236 | 98 | 75 | 95 | 48 |

[a]Not determined.

The data in Table 2 indicate that the inclusion of a polar organic solvent (10 vol %) in the gtf reaction solution reduced the DPw of the alpha-1,3-glucan polymer produced in the reaction. This reduction was as compared to the DPw of the polymer produced in the control reaction in which no polar organic solvent was added (water only). The DPw reductions observed ranged from about 17% (when methanol was used) to about 67% (when sulfolane was used). In almost every case (except where the added polar organic solvent was methyl formamide), over 90% of the sucrose supplied in each reaction was consumed, indicating that the added polar organic solvent generally did not inhibit complete consumption of sucrose. Furthermore, since many of the solvent systems had sucrose conversion after 24 hours similar to the sucrose conversion of the pure aqueous system (Table 2), but lower polymer DPw, differences in polymer DPw cannot necessarily be attributed to enzyme activity.

Table 2 also indicates that both protic and aprotic polar organic solvents were useful in gtf reaction solutions to reduce the DPw of the alpha-1,3-glucan polymer produced in the reaction. The protic polar organic solvents were methanol, methyl formamide, ethanol, i-propanol (isopropanol), n-propanol (1-propanol), t-butanol (tert-butyl alcohol), and formamide, whereas the aprotic polar organic solvents were DMSO (dimethyl sulfoxide), acetone, acetonitrile, N,N-dimethylformamide, N,N-dimethylacetamide, tetrahydrofuran, propylene carbonate, and sulfolane. In general, aprotic polar organic solvents were more effective at reducing polymer DPw when added to the reaction compared to protic polar organic solvents (Table 2). Most of the gtf reactions to which an aprotic polar organic solvent was added produced glucan polymer with a DPw that was reduced by more than 50% compared to the glucan polymer produced in the completely aqueous gtf reaction.

Thus, the addition of a polar organic solvent to a gtf reaction solution reduces the molecular weight of the alpha-1,3-glucan polymer product of the reaction.

Example 2

Glucan Polymerization Reactions Using qtfJ Enzyme and Acetonitrile

This Example describes producing alpha-1,3-glucan in gtf-catalyzed reactions containing the aprotic polar organic solvent, acetonitrile. Specifically, this example shows that increasing levels of acetonitrile lead to greater reductions in polymer molecular weight, and that acetonitrile can reduce the molecular weight of polymer produced in reactions at 37° C.

The procedure described in Example 1 was followed to prepare S. salivarius gtfJ (SEQ ID NO:2) reaction solutions containing acetonitrile. However, the amount of acetonitrile added to the reaction solution was varied from 2-20 mL (for 2, 10, or 20 vol % acetonitrile); the amount of water was adjusted accordingly to maintain a total reaction volume of 100 mL. The results of these reactions are provided in Table 3.

TABLE 3

Molecular Weight of alpha-1,3-Glucan Polymer Produced in Reaction Solutions Containing Various Amounts of Acetonitrile

| Temperature (° C.) | Volume % Acetonitrile | DPw | Initial sucrose (g/L) | % Sucrose consumption |
|---|---|---|---|---|
| 25 | 0 | 714 | 106 | 96 |
| 25 | 2 | 702 | 100 | 96 |
| 25 | 10 | 321 | 100 | >95 |
| 25 | 20 | 186 | 101 | 63 |

As indicated in Table 3, increasing the amount of acetonitrile in the gtf reaction resulted in greater reductions in the alpha-1,3-glucan polymer molecular weight. These results indicate that glucan polymer molecular weight can be controlled by varying the concentration of the added polar organic solvent.

Next, the procedure described in Example 1 was followed to prepare gtf reaction solutions containing acetonitrile, with the exception that the temperature of the reaction was 37° C. (as opposed to 25° C.). The results of these reactions are provided in Table 4.

19

TABLE 4

Molecular Weight of alpha-1,3-Glucan Polymer Produced at 37° C. in Reaction Solutions Containing Acetonitrile

| Temperature (° C.) | Volume % Acetonitrile | DPw | Initial sucrose (g/L) | % Sucrose consumption |
|---|---|---|---|---|
| 37 | 0 | 492 | 96 | 97 |
| 37 | 10 | 187 | 98 | 94 |

As indicated in Table 4, performing the glucan polymerization reaction with acetonitrile at 37° C. led to the production of polymer with reduced molecular weight. As can be seen by comparing the results in Tables 3 and 4 for gtf reaction solutions containing 10 vol % acetonitrile, raising the reaction temperature from 25° C. to 37° C. led to enhanced reduction of the molecular weight of the alpha-1,3-glucan product (from a DPw of 321 at 25° C. to a DPw of 187 at 37° C.). The percent sucrose consumption was over 90% in both the 25° C. and 37° C. reactions.

Table 4 indicates that gtf reaction solutions that were completely aqueous (no polar organic solvent added) also produced polymer with reduced molecular weight, when compared to the same reaction performed at 25° C. Specifically, the DPw of 492 obtained in the 37° C. reaction was lower than the DPw of 714 obtained in the 25° C. reaction (Table 3); this represents a reduction in polymer molecular weight by about 31%. In contrast, the reduction in polymer molecular weight observed between the 25° C. and 37° C. reactions containing 10 vol % acetonitrile was about 42%. The inclusion of a polar organic solvent therefore can enhance the reduction in polymer molecular weight observed when increasing reaction temperature.

Example 3

Glucan Polymerization Reactions Using Various gtf Enzymes

This Example describes producing alpha-1,3-glucan in reactions containing a polar organic solvent and different gtf enzymes. Specifically, this example shows that, in addition to SEQ ID NO:2, other types of gtf enzymes can be used in reactions containing acetonitrile to produce glucan polymer with reduced molecular weight.

The gtf enzymes used in this example were as follows:

The *S. salivarius* gtfJ enzyme was SEQ ID NO:2, encoded by SEQ ID NO:1.

An N-terminally truncated version of a *Streptococcus sobrinus* gtf enzyme identified in GENBANK under GI number 450874 was used (SEQ ID NO:4, encoded by SEQ ID NO:3; herein referred to as "0874").

An N-terminally truncated version of *Streptococcus salivarius* K12 gtf enzyme identified in GENBANK as a dextransucrase under GI number 400182678 was used (SEQ ID NO:6, encoded by SEQ ID NO:5; herein referred to as "2678").

An N-terminally truncated version of *Streptococcus salivarius* PS4 gtf enzyme identified in GENBANK as a putative glucosyltransferase under GI number 383282919 was used (SEQ ID NO:8, encoded by SEQ ID NO:7; herein referred to as "2919").

An N-terminally truncated version of *Streptococcus dentirousetti* gtf enzyme identified in GENBANK under GI number 167735926 was used (SEQ ID NO:10, encoded by SEQ ID NO:9; herein referred to as "5926").

20

An N-terminally truncated version of *Streptococcus salivarius* SK126 gtf enzyme identified in GENBANK under GI number 228476855 was used (SEQ ID NO:12, encoded by SEQ ID NO:11; herein referred to as "6855").

Another version of the *S. salivarius* gtfJ enzyme used in this study was SEQ ID NO:14 (herein referred to as "gtfJ-T1"). SEQ ID NO:14, compared to the amino acid sequence identified in GENBANK under GI number 47527, is truncated by 230 amino acids at the N-terminus and 384 amino acids at the C-terminus. As with the other gtf enzymes disclosed herein, SEQ ID NO:14 was produced using a DNA that was codon-optimized for expression in *E. coli*. SEQ ID NO:13 (Table 1), which is representative of a sequence encoding SEQ ID NO:14, was not used for enzyme expression since it is not codon-optimized.

Another version of the *S. dentirousetti* gtf enzyme used in this study was SEQ ID NO:16 (herein referred to as "5926-T1"). SEQ ID NO:16, compared to the amino acid sequence identified in GENBANK under GI number 167735926, is truncated by 199 amino acids at the N-terminus and 417 amino acids at the C-terminus. As with the other gtf enzymes disclosed herein, SEQ ID NO:16 was produced using a DNA that was codon-optimized for expression in *E. coli*. SEQ ID NO:15 (Table 1), which is representative of a sequence encoding SEQ ID NO:16, was not used for enzyme expression since it is not codon-optimized.

The procedure described in Example 1 was followed to prepare reaction solutions containing a particular gtf (see Table 5) and acetonitrile (10 vol %). The reactions were performed at 25° C. and the alpha-1,3-glucan produced in each reaction was analyzed for DPw. The results are provided in Table 5.

TABLE 5

Molecular Weight of alpha-1,3-Glucan Polymer Produced in Reaction Solutions Containing Various gtf Enzymes

| gtf Enzyme | SEQ ID NO | Solvent[a] | DPw | Initial sucrose (g/L) | % Sucrose consumption |
|---|---|---|---|---|---|
| 0874 | SEQ ID NO: 4 | Acetonitrile | 52 | 149 | 97 |
| | | None | 56 | 143 | 90 |
| 2678 | SEQ ID NO: 6 | Acetonitrile | 283 | 149 | 65 |
| | | None | 657 | 151 | 93 |
| 2919 | SEQ ID NO: 8 | Acetonitrile | 188 | 149 | 94 |
| | | None | 414 | 152 | 91 |
| 5926 | SEQ ID NO: 10 | Acetonitrile | 57 | 149 | 74 |
| | | None | 68 | 149 | 96 |
| 5926-T1 | SEQ ID NO: 16 | Acetonitrile | 70 | 149 | 97 |
| | | None | 108 | 150 | 100 |
| 6855 | SEQ ID NO: 12 | Acetonitrile | 247 | 149 | 96 |
| | | None | 571 | 151 | 96 |
| gtfJ | SEQ ID NO: 2 | Acetonitrile | 305 | 150 | 71 |
| | | None | 577 | 151 | 96 |
| gtfJ-T1 | SEQ ID NO: 14 | Acetonitrile | 252 | 149 | 96 |
| | | None | 495 | 142 | 94 |

[a]Solvent was completely aqueous (None) or contained 10 vol % acetonitrile (Acetonitrile).

As indicated in Table 5, all the different gtf enzymes produced alpha-1,3-glucan polymer having a reduced molecular weight when used in a reaction solution containing a polar organic solvent (10 vol % acetonitrile), compared to when the enzymes were used in purely aqueous control reactions. All but one of the gtf reactions yielded glucan polymer with a DPw that was reduced by at least 15%.

Most of the reactions containing acetonitrile consumed over 90% of the sucrose supplied in the reaction (Table 5), indicating that the added acetonitrile generally did not inhibit gtf enzyme activity. In certain reactions (gtfs 0874, 2919, 6855, gtfJ-T1), the addition of acetonitrile resulted in sucrose consumption that was equal to or greater than the sucrose consumption that occurred in the purely aqueous reaction.

Table 5 also indicates that the addition of acetonitrile in a gtf reaction reduced the molecular weight of the alpha-1,3-glucan polymer produced regardless of the polymer size generally produced by the gtf. For example, even though gtf enzymes 0874 (SEQ ID NO:4) and 6855 (SEQ ID NO:12) produced glucan polymers of 56 and 571 DPw, respectively, in purely aqueous reaction conditions, both enzymes produced polymer with reduced DPw in reactions containing acetonitrile.

Table 5 also indicates that the addition of acetonitrile in a gtf reaction reduced the molecular weight of the alpha-1,3-glucan polymer produced regardless of the size of the gtf. Specifically, both enzymes gtfJ (SEQ ID NO:2) and its shortened counterpart gtfJ-T1 (SEQ ID NO:14) produced glucan polymer with reduced DPw when acetonitrile was included in the reaction. This was similarly the case with gtf enzymes 5926 (SEQ ID NO:10) and 5926-T1 (SEQ ID NO:16).

Thus, various types of gtf enzymes can be used in reactions containing a polar organic solvent to produce alpha-1,3-glucan polymer with reduced molecular weight. Given that all of SEQ ID NOs:2, 4, 6, 8, 10, 12, 14 and 16 produced alpha-1,3-glucan polymer with reduced molecular weight in reaction solutions containing a polar organic solvent, other gtf enzymes such as SEQ ID NOs:18, 20, 22, 24, 26, 28, 30 and 32 could be used in a similar manner to produce alpha-1,3-glucan polymer with reduced molecular weight.

What is claimed is:

1. A process for producing poly alpha-1,3-glucan comprising:
    (a) contacting water, sucrose, a polar organic solvent, and a bacterial glucosyltransferase enzyme in a solution, wherein the glucosyltransferase enzyme synthesizes poly alpha-1,3-glucan, wherein a poly alpha-1,3-glucan is produced having a reduced molecular weight compared to the molecular weight of the poly alpha-1,3-glucan produced in the absence of the polar organic solvent, wherein the glucosyltransferase enzyme comprises an amino acid sequence that is at least 97% identical to SEQ ID NO: 12, SEQ ID NO: 2, SEQ ID NO: 32, SEQ ID NO: 4, SEQ ID NO: 6, SEQ ID NO: 8, SEQ ID NO: 10, SEQ ID NO: 14, SEQ ID NO: 18, SEQ ID NO: 20, SEQ ID NO: 22, SEQ ID NO: 24, SEQ ID NO: 26, SEQ ID NO: 28, or SEQ ID NO:30; and
    (b) optionally, isolating the poly alpha-1,3-glucan produced in step (a); wherein the polar organic solvent is selected from the group consisting of acetonitrile, dimethyl sulfoxide, acetone, N,N-dimethylformamide, N,N-dimethylacetamide, tetrahydrofuran, propylene carbonate, sulfolane, hexamethylphosphoramide, 1,3-dimethyl-2-imidazolidinone, nitromethane, butanone, methanol, methyl formamide, ethanol, isopropanol, 1-propanol, tert-butyl alcohol, formamide, n-butanol, ethylene glycol, 2-methoxyethanol, 1-methoxy-2-propanol, glycerol, 1,2-propanediol, and 1,3-propanetriol.

2. The process of claim 1, wherein the polar organic solvent is selected from the group consisting of acetonitrile, dimethyl sulfoxide, acetone, N,N-dimethylformamide, N,N-dimethylacetamide, tetrahydrofuran, propylene carbonate, sulfolane, methanol, methyl formamide, ethanol, isopropanol, 1-propanol, tert-butyl alcohol, and formamide.

3. The process of claim 1, wherein the concentration of the polar organic solvent in the solution is about 2% to about 20% by volume.

4. The process of claim 3, wherein the concentration of the polar organic solvent in the solution is about 10% by volume.

5. The process of claim 1, wherein the solution has a temperature between about 5° C. to about 50° C.

6. The process of claim 1, wherein the initial concentration of the sucrose in the solution is about 20 g/L to about 400 g/L.

7. The process of claim 1, wherein the molecular weight of the poly alpha-1,3-glucan produced in step (a) is reduced by at least about 15%.

8. The process of claim 1, wherein the molecular weight of the poly alpha-1,3-glucan produced in step (a) is reduced by at least about 50%.

9. The process of claim 1, wherein the molecular weight is measured as weight average degree of polymerization (DPw).

10. The process of claim 9, wherein the DPw of the poly alpha-1,3-glucan produced in step (a) is between about 40 and 800.

11. The process of claim 1, wherein the glucosyltransferase enzyme comprises an amino acid sequence that is at least 98% identical to SEQ ID NO:12, SEQ ID NO:2, SEQ ID NO:32, SEQ ID NO:4, SEQ ID NO:6, SEQ ID NO:8, SEQ ID NO:10, SEQ ID NO:14, SEQ ID NO:18, SEQ ID NO:20, SEQ ID NO:22, SEQ ID NO:24, SEQ ID NO:26, SEQ ID NO:28, or SEQ ID NO:30.

12. The process of claim 2, wherein the glucosyltransferase enzyme comprises an amino acid sequence that is at least 98% identical to SEQ ID NO:12, SEQ ID NO:2, SEQ ID NO:32, SEQ ID NO:4, SEQ ID NO:6, SEQ ID NO:8, SEQ ID NO:10, SEQ ID NO:14, SEQ ID NO:18, SEQ ID NO:20, SEQ ID NO:22, SEQ ID NO:24, SEQ ID NO:26, SEQ ID NO:28, or SEQ ID NO:30.

13. The process of claim 1, wherein the glucosyltransferase enzyme comprises SEQ ID NO:12, SEQ ID NO:2, SEQ ID NO:32, SEQ ID NO:4, SEQ ID NO:6, SEQ ID NO:8, SEQ ID NO:10, SEQ ID NO:14, SEQ ID NO:18, SEQ ID NO:20, SEQ ID NO:22, SEQ ID NO:24, SEQ ID NO:26, SEQ ID NO:28, or SEQ ID NO:30.

14. The process of claim 2, wherein the glucosyltransferase enzyme comprises SEQ ID NO:12, SEQ ID NO:2, SEQ ID NO:32, SEQ ID NO:4, SEQ ID NO:6, SEQ ID NO:8, SEQ ID NO:10, SEQ ID NO:14, SEQ ID NO:18, SEQ ID NO:20, SEQ ID NO:22, SEQ ID NO:24, SEQ ID NO:26, SEQ ID NO:28, or SEQ ID NO:30.

* * * * *